US011939616B2

(12) United States Patent
Sackstein

(10) Patent No.: US 11,939,616 B2
(45) Date of Patent: Mar. 26, 2024

(54) COMPOSITIONS AND METHODS FOR ENFORCING FUCOSYLATION OF LACTOSAMINYL GLYCANS IN HUMAN CELLS WITH ALPHA(1,3)-FUCOSYLTRANSFERASES

(71) Applicant: The Brigham and Women's Hospital, Boston, MA (US)

(72) Inventor: Robert Sackstein, Pinecrest, FL (US)

(73) Assignee: THE BRIGHAM AND WOMEN'S HOSPITAL, INC., Boston, MA (US)

(*) Notice: Subject to any disclaimer, the term of this patent is extended or adjusted under 35 U.S.C. 154(b) by 406 days.

(21) Appl. No.: 17/027,794

(22) Filed: Sep. 22, 2020

(65) Prior Publication Data

US 2021/0017562 A1 Jan. 21, 2021

Related U.S. Application Data

(63) Continuation of application No. PCT/US2019/023668, filed on Mar. 22, 2019.

(60) Provisional application No. 62/647,404, filed on Mar. 23, 2018.

(51) Int. Cl.
*A61K 35/12* (2015.01)
*C12N 9/10* (2006.01)
*C12P 21/00* (2006.01)

(52) U.S. Cl.
CPC ..... *C12P 21/005* (2013.01); *C12Y 204/01214* (2013.01)

(58) Field of Classification Search
CPC ........ A61K 35/16; A61K 35/28; A61K 35/12; A61K 2035/124; C12Y 204/01214
See application file for complete search history.

(56) References Cited

U.S. PATENT DOCUMENTS

2002/0019342 A1* 2/2002 Bayer ............... A61P 29/00
435/7.1
2010/0322940 A1 12/2010 Bayer
2012/0149887 A1 6/2012 Sawa

FOREIGN PATENT DOCUMENTS

WO 2017201537 11/2017

OTHER PUBLICATIONS

Gisela et al., Stem Cells, 35, 1080-1092, 2017.*
Knibbs, R. N., Craig, R. A., Natsuka, S., Chang, A., Cameron, M., Lowe, J. B., and Stoolman, L. M. (1996) The fucosyltransferase FucT-VII regulates E-selectin ligand synthesis in human T cells. J Cell Biot 133, 911-920.

Nakayama, F., Nishihara, S., Iwasaki, H., Kudo, T., Okubo, R., Kaneko, M., Nakamura, M., Karube, M., Sasaki, K., and Narimatsu, H. (2001) CD15 Expression in Mature Granulocytes is Determined by a1,3-Fucosyltransferase IX, but in Promyelocytes and Monocytes by a1,3-Fucosyltransferase IV. Journal of Biological Chemistry 276, 16100-16106.
Patnaik, S. K., Potvin, B., and Stanley, P. (2004) LEC12 and LEC29 Gain-of-Function Chinese Hamster Ovary Mutants Reveal Mechanisms for Regulating VIM-2 Antigen Synthesis and E-selectin Binding. Journal of Biological Chemistry 279, 49716-49726.
Buffone, A., Mondal, N., Gupta, R., McHugh, K. P., Lau, J. T. Y., and Neelamegham, S. (2013) Silencing a1,3-Fucosyltransferases in Human Leukocytes Reveals a Role for FUT9 Enzyme during E-selectin-mediated Cell Adhesion. Journal of Biological Chemistry 288, 1620-1633.
Tu, L., and Banfield, D. K. (2010) Localization of Golgi-resident glycosyltransferases. Cellular and Molecular Life Sciences 67, 29-41.
Maly, P., Thall, A., Petryniak, B., Rogers, C. E., Smith, P. L., Marks, R. M., Kelly, R. J., Gersten, K. M., Cheng, G., Saunders, T. L., Camper, S. A., Camphausen, R. T., Sullivan, F. X., Isogai, Y., Hindsgaul, 0., von Andrian, U. H., and Lowe, J. B. (1996) The alpha(1,3)fucosyltransferase Fuc-TVII controls leukocyte trafficking through an essential role in L-, E-, and P-selectin ligand biosynthesis. Cell 86, 643-653.
Homeister, J. W., Daugherty, A., and Lowe, J. B. (2004) Alpha(1,3)fucosyltransferases FucT-IV and FucT-VII control susceptibility to atherosclerosis in apolipoprotein E-/mice. Arterioscler Thromb Vasc Biol 24, 1897-1903.
Smithson, G., Rogers, C. E., Smith, P. L., Scheidegger, E. P., Petryniak, B., Myers, J. T., Kim, D. S., Homeister, J. W., and Lowe, J. B. (2001) Fuc-TVII is required for T helper 1 and T cytotoxic 1 lymphocyte selectin ligand expression and recruitment in inflammation, and together with Fuc-TIV regulates naive T cell trafficking to lymph nodes. JExp Med 194, 601-614.
Homeister, J. W., Thall, A. D., Petryniak, B., Maly, P., Rogers, C. E., Smith, P. L., Kelly, R. J., Gersten, K. M., Askari, S. W., and Cheng, G. (2001) The alpha(1,3)fucosyltransferases FucT-IV and FucT-VII exert collaborative control over selectin-dependent leukocyte recruitment and lymphocyte homing. Immunity 15.
Gersten, K. M., Natsuka, S., Trinchera, M., Petryniak, B., Kelly, R. J., Hiraiwa, N., Jenkins, N. A., Gilbert, D. J., Copeland, N. G., and Lowe, J. B. (1995) Molecular Cloning, Expression, Chromosomal Assignment, and Tissue-specific Expression of a Murine a-(1,3)-Fucosyltransferase Locus Corresponding to the Human ELAM-1 Ligand Fucosyl Transferase. Journal of Biological Chemistry 270, 25047-25056.

(Continued)

*Primary Examiner* — Maryam Monshipouri
(74) *Attorney, Agent, or Firm* — Bryan Cave Leighton Paisner LLP

(57) ABSTRACT

The present disclosure provides, inter alia, compositions and methods for enforcing a pattern of cell surface fucosylated lactosaminyl glycans on a human cell. In certain embodiments, the compositions and/or methods utilize one or more members of the α(1,3)-fucosyltransferase family. In certain embodiments, a process for custom-modifying a fucosylated lactosaminyl glycan on a human cell is disclosed.

4 Claims, 18 Drawing Sheets
Specification includes a Sequence Listing.

(56) References Cited

OTHER PUBLICATIONS

Stolfa, G., Mondal, N., Zhu, Y., Yu, X., Buffone, A., Jr., and Neelamegham, S. (2016) Using CRISPR-Cas9 to quantify the contributions of O-glycans, N-glycans and Glycosphingolipids to human leukocyte-endothelium adhesion. Scientific reports 6, 30392.
Mondal, N., Stolfa, G., Antonopoulos, A., Zhu, Y., Wang, S. S., Buffone, A., Jr., Atilla-Gokcumen, G. E., Haslam, S. M., Dell, A., and Neelamegham, S. (2016) Glycosphingolipids on Human Myeloid Cells Stabilize E-Selectin-Dependent Rolling in the Multistep Leukocyte Adhesion Cascade. Arterioscler Thromb Vasc Biol 36, 718-727.
Fukushi, Y., Nudelman, E., Levery, S. B., Hakomori, S., and Rauvala, H. (1984) Novel fucolipids accumulating in human adenocarcinoma. III. A hybridoma antibody (FH6) defining a human cancer-associated difucoganglioside (VI3NeuAcV3III3Fuc2nLc6). J Biol Chem 259, 10511-10517.
Mandal, P. K., and Rossi, D. J. (2013) Reprogramming human fibroblasts to pluripotency using modified mRNA. Nat Protoc 8, 568-582.
Garner, B., Priestman, D. A., Stocker, R., Harvey, D. J., Butters, T. D., and Platt, F. M. (2002) Increased glycosphingolipid levels in serum and aortae of apolipoprotein E gene knockout mice. J Lipid Res 43, 205-214.
Aoki, K., Perlman, M., Lim, J. M., Cantu, R., Wells, L., and Tiemeyer, M. (2007) Dynamic developmental elaboration of N-linked glycan complexity in the *Drosophila melanogaster* embryo. JBiol Chem 282, 9127-9142.
Canis, K., McKinnon, T. A., Nowak, A., Panico, M., Morris, H. R., Laffan, M., and Dell, A. (2010) The plasma von Willebrand factor O-glycome comprises a surprising variety of structures including ABH antigens and disialosyl motifs. J Thromb Haemost 8, 137-145.
Alley, W. R., Jr., Madera, M., Mechref, Y., and Novotny, M. V. (2010) Chip-based reversed-phase liquid chromatography-mass spectrometry of permethylated N-linked glycans: a potential methodology for cancer-biomarker discovery. Anal Chem 82, 5095-5106.
Carlson, D. M. (1966) Oligosaccharides isolated from pig submaxillary mucin. JBiol Chem 241, 2984-2986.
Kang, P., Mechref, Y., Klouckova, I., and Novotny, M. V. (2005) Solid-phase permethylation of glycans for mass spectrometric analysis. Rapid Commun Mass Spectrom 19, 3421-3428.
Ashline, D. J., Hanneman, A. J., Zhang, H., and Reinhold, V. N. (2014) Structural documentation of glycan epitopes: sequential mass spectrometry and spectral matching. J Am Soc Mass Spectrom 25, 444-453.
Ashline, D. J., Zhang, H., and Reinhold, V. N. (2017) Isomeric complexity of glycosylation documented by MSn. Anal Bioanal Chem 409, 439-451.
Mollicone, R., et al., Molecular basis for Lewis alpha(1,3/1,4)-fucosyltransferase gene deficiency (FUT3) found in Lewis-negative Indonesian pedigrees. Journal of Biological Chemistry, 1994. 269(33): p. 20987-20994.
Nishihara, S., et al., Human a-1,3 Fucosyltransferase (FucT-VI) Gene is Located at Only 13 kb 3' to the Lewis Type Fucosyltransferase (FucT-III) Gene on Chromosome 19. Biochemical and Biophysical Research Communications, 1993. 190(1): p. 42-46.
Cameron, H.S., D. Szczepaniak, and B.W. Weston, Expression of Human Chromosome 19p a(1, 3)-Fucosyltransferase Genes in Normal Tissues: Alternative Splicing, Poly ADElVYLATION, and Isoforms. Journal of Biological Chemistry, 1995. 270(34): p. 20112-20122.
De Vries, T., et al., Acceptor Specificity of Different Length Constructs of Human Recombinant al ,3/4-Fucosyltransferases: Replacement of the Stem Region and the Transmembrane Domain of Fucosyltransferase V by Protein a Results in an Enzyme With GDP-Fucose Hydrolyzing Activity. Journal of Biological Chemistry, 1995. 270(15): p. 8712-8722.
De Vries, T., et al., Acceptor specificity of GDP-Fuc:Galal 4GlcNAc-R d3-fucosyltransferase VI (FucT VI) expressed in insect cells as soluble, secreted enzyme. Glycobiology, 1997. 7(7): p. 921-927.
Lowe, J.B., et al., Molecular cloning of a human fucosyltransferase gene that determines expression of the Lewis x and VIM-2 epitopes but not ELAM-1-dependent cell adhesion. Journal of Biological Chemistry, 1991. 266(26): p. 17467-17477.
Clarke, J.L. and W.M. Watkins, 1,3-L-Fucosyltransferase Expression in Developing Human Myeloid Cells: Antigenic, Enzymatic, and mRNA Analyses. Journal of Biological Chemistry, 1996. 271(17): p. 10317-10328.
Chandrasekaran, E.V., et al., Specificity Analysis of Three Clonal and Five Non-Clonal a1,3-1-Fucosyltransferases with Sulfated, Sialylated, or Fucosylated Synthetic Carbohydrates as Acceptors in Relation to the Assembly of 3'-Sialy1-6'-sulfo Lewis x (the L-Selectin Ligand) and Related Complex Structures. Biochemistry, 1996. 35(27): p. 8925-8933.
Nystrom, K., et al., Virus-induced transcriptional activation of host FUT genes associated with neo-expression of Ley in cytomegalovirus-infected and sialyl-Lex in varicella-zoster virus-infected diploid human cells. Glycobiology, 2007. 17 (4): p. 355-366.
Nystrom, K., et al., Induction of sialyl-Lex expression by herpes simplex virus type 1 is dependent on viral immediate early RNA-activated transcription of host fucosyltransferase genes. Glycobiology, 2009. 19(8): p. 847-859.
Koszdin, K.L. and B.R. Bowen, The cloning and expression of a human a-1,3 fucosyltransferase capable of forming the E-selectin ligand. Biochemical and Biophysical Research Communications, 1992. 187(1): p. 152-157.
Costache, M., et al., Evolution of Fucosyltransferase Genes in Vertebrates. Journal of Biological Chemistry, 1997. 272(47): p. 29721-29728.
Borsig, L., et al., Trafficking and localization studies of recombinant al ,3-fucosyltransferase VI stably expressed in CHO cells. Glycobiology, 1998. 8(3): p. 259-268.
Izawa, M., et al., Expression of Sialyl 6-Sulfo Lewis X is Inversely Correlated with Conventional Sialyl Lewis X Expression in Human Colorectal Cancer. Cancer Research, 2000. 60(5): p. 1410-1416.
Wagers, A.J., J.B. Lowe, and G.S. Kansas, An important role for the alpha 1,3 fucosyltransferase, FucT-VII, in leukocyte adhesion to E-selectin. Blood, 1996. 88(6): p. 2125-32.
Kudo, T., et al., Expression cloning and characterization of a novel murine alpha], 3-fucosyltransferase, mFuc-TIX, that synthesizes the Lewis x (CD15) epitope in brain and kidney. J Biol Chem, 1998. 273(41): p. 26729-38.
Huang, M.-C., et al., P-selectin Glycoprotein Ligand-1 and E-selectin Ligand-1 are Differentially Modified by Fucosyltransferases Fuc-TIV and Fuc-TVII in Mouse Neutrophils. Journal of Biological Chemistry, 2000. 275(40): p. 31353-31360.
R. Sackstein, The lymphocyte homing receptors: gatekeepers of the multistep paradigm, Curr Opin Hematol 12, 444 (2005).
T. Lapidot, A. Dar, 0. Kollet, How do stem cells find their way home?, Blood 106, 1901 (2005).
T. A. Springer, Traffic signals for lymphocyte recirculation and leukocyte emigration: the multistep paradigm, Cell 76, 301 (1994).
A. Peled et al., Dependence of human stem cell engraftment and repopulation of NOD/SCID mice on CXCR4, Science 283, 845 (1999).
D. A. Sipkins et al., In vivo imaging of specialized bone marrow endothelial microdomains for tumor engraftment, Nature 435, 969 (2005).
R. Sackstein, Immunol. Rev. 230: 140-163 (2009).
M. J. Polley et al., CD62 and endothelial cell-leukocyte adhesion molecule 1 (ELAM-1) recognize the same carbohydrate ligand, sialyl-Lewis x, Proc Natl Acad Sci USA 88, 6224 (1991).
Z. Laszik et al., P-selectin glycoprotein ligand-1 is broadly expressed in cells of myeloid, lymphoid, and dendritic lineage and in some nonhematopoietic cells, Blood 88, 3010 (1996).
C. J. Dimitroff, J. Y. Lee, S. Rafii, R. C. Fuhlbrigge, R. Sackstein, Cd44 is a Major E-Selectin Ligand on Human Hematopoietic Progenitor Cells, J Cell Biol 153, 1277 (2001).
C. J. Dimitroff, J. Y. Lee, R. C. Fuhlbrigge, R. Sackstein, A distinct glycoform of CD44 is an L-selectin ligand on human hematopoietic cells, Proc Natl Acad Sci US A 97, 13841 (2000).
Fuhlbrigge et al CD43 is a ligand for E-selectin on CLA+ human T cells, Blood 107:1421-1426 (2006).

(56) References Cited

OTHER PUBLICATIONS

Sackstein, R. (2009) Glycosyltransferase-programmed stereosubstitution (GPS) to create HCELL: engineering a roadmap for cell migration. Immunol Rev 230, 51-74.

Gooi, H. C., Feizi, T., Kapadia, A., Knowles, B. B., Solter, D., and Evans, M. J. (1981) Stage-specific embryonic antigen involves alpha 1 goes to 3 fucosylated type 2 blood group chains. Nature 292, 156-158.

Solter, D., and Knowles, B. B. (1978) Monoclonal antibody defining a stage-specific mouse embryonic antigen (SSEA-1). Proc Natl Acad Sci USA 75, 5565-5569.

Fenderson, B. A., Zehavi, U., and Hakomori, S. (1984) A multivalent lacto-N-fucopentaose III-lysyllysine conjugate decompacts preimplantation mouse embryos, while the free oligosaccharide is ineffective. JExp Med 160, 1591-1596.

Capela, A., and Temple, S. (2002) LeX/ssea-1 is expressed by adult mouse CNS stem cells, identifying them as nonependymal. Neuron 35, 865-875.

Klassen, H., Schwartz, M. R., Bailey, A. H., and Young, M. J. (2001) Surface markers expressed by multipotent human and mouse neural progenitor cells include tetraspanins and non-protein epitopes. Neurosci Lett 312, 180-182.

Yanagisawa, M., Taga, T., Nakamura, K., Ariga, T., and Yu, R. K. (2005) Characterization of glycoconjugate antigens in mouse embryonic neural precursor cells. J Neurochem 95, 1311-1320.

Pruszak, J., Ludwig, W., Blak, A., Alavian, K., and Isacson, 0. (2009) CD15, CD24, and CD29 Define a Surface Biomarker Code for Neural Lineage Differentiation of Stem Cells. Stem Cells 27, 2928-2940.

Yagi, H., Saito, T., Yanagisawa, M., Yu, R. K., and Kato, K. (2012) Lewis X-carrying N-glycans regulate the proliferation of mouse embryonic neural stem cells via the Notch signaling pathway. J Blot Chem 287, 24356-24364.

Van Gisbergen, K. P., Sanchez-Hernandez, M., Geijtenbeek, T. B., and van Kooyk, Y. (2005) Neutrophils mediate immune modulation of dendritic cells through glycosylation-dependent interactions between Mac-1 and DC-SIGN. JExp Med 201, 1281-1292.

Gruss, H. J., and Kadin, M. E. (1996) Pathophysiology of Hodgkin's disease: functional and molecular aspects. Baillieres Clin Haematol 9, 417-446.

Read, T. A., Fogarty, M. P., Markant, S. L., McLendon, R. E., Wei, Z., Ellison, D. W., Febbo, P. G., and Wechsler-Reya, R. J. (2009) Identification of CD15 as a marker for tumor-propagating cells in a mouse model of medulloblastoma. Cancer cell 15, 135-147.

Seidmann, L., Anspach, L., and Roth, W. (2016) The embryo-placental CD15-positive "vasculogenic zones" as a source of propranolol-sensitive pediatric vascular tumors. Placenta 38, 93-99.

Foxall, C., Watson, S. R., Dowbenko, D., Fennie, C., Lasky, L. A., Kiso, M., Hasegawa, A., Asa, D., and Brandley, B. K. (1992) The three members of the selectin receptor family recognize a common carbohydrate epitope, the sialyl Lewis(x) oligosaccharide. J Cell Biol 117, 895-902.

Sackstein, R. (2004) The bone marrow is akin to skin: HCELL and the biology of hematopoietic stem cell homing. The Journal of investigative dermatology 122, 1061-1069.

Merzaban, J. S., Burdick, M. M., Gadhoum, S. Z., Dagia, N. M., Chu, J. T., Fuhlbrigge, R. C., and Sackstein, R. (2011) Analysis of glycoprotein E-selectin ligands on human and mouse marrow cells enriched for hematopoietic stem/progenitor cells. Blood 118, 1774-1783.

Silva M, Fung RKF, Donnelly CB, Videira PA, Sackstein R., Cell-Specific Variation in E-Selectin Ligand Expression among Human Peripheral Blood Mononuclear Cells: Implications for Immunosurveillance and Pathobiology, J Immunol. May 1, 2017;198(9):3576-3587.

Julien, S., Ivetic, A., Grigoriadis, A., QiZe, D., Burford, B., Sproviero, D., Picco, G., Gillett, C., Papp, S. L., Schaffer, L., Tutt, A., Taylor-Papadimitriou, J., Pinder, S. E., and Burchell, J. M. (2011) Selectin ligand sialyl-Lewis x antigen drives metastasis of hormone-dependent breast cancers. Cancer Res 71, 7683-7693.

Liang, J. X., Liang, Y., and Gao, W. (2016) Clinicopathological and prognostic significance of sialyl Lewis X overexpression in patients with cancer: a meta-analysis. OncoTargets and therapy 9, 3113-3125.

St Hill, C. A. (2011) Interactions between endothelial selectins and cancer cells regulate metastasis. Front Biosci (Landmark Ed) 16, 3233-3251.

Handa, K., Stroud, M. R., and Hakomori, S. (1997) Sialosyl-fucosyl Poly-LacNAc without the sialosyl-Lex epitope as the physiological myeloid cell ligand in E-selectin-dependent adhesion: studies under static and dynamic flow conditions. Biochemistry 36, 12412-12420.

Tiemeyer, M., Swiedler, S. J., Ishihara, M., Moreland, M., Schweingruber, H., Hirtzer, P., and Brandley, B. K. (1991) Carbohydrate ligands for endothelial-leukocyte adhesion molecule 1. Proc Natl Acad Sci USA 88, 1138-1142.

Kukowska-Latallo, J. F., Larsen, R. D., Nair, R. P., and Lowe, J. B. (1990) A cloned human cDNA determines expression of a mouse stage-specific embryonic antigen and the Lewis blood group alpha(1,3/1,4)fucosyltransferase. Genes & Development 4, 1288-1303.

Lowe, J. B., Kukowska-Latallo, J. F., Nair, R. P., Larsen, R. D., Marks, R. M., Macher, B. A., Kelly, R. J., and Ernst, L. K. (1991) Molecular cloning of a human fucosyltransferase gene that determines expression of the Lewis x and VIM-2 epitopes but not ELAM-1-dependent cell adhesion. Journal of Biological Chemistry 266, 17467-17477.

Goelz, S. E., Hession, C., Goff, D., Griffiths, B., Tizard, R., Newman, B., Chi-Rosso, G., and Lobb, R. (1990) ELFT: A gene that directs the expression of an ELAM-1 ligand. Cell 63, 1349-1356.

Weston, B. W., Nair, R. P., Larsen, R. D., and Lowe, J. B. (1992) Isolation of a novel human alpha (1,3) fucosyltransferase gene and molecular comparison to the human Lewis blood group alpha (1,3/1,4)fucosyltransferase gene. Syntenic, homologous, nonallelic genes encoding enzymes with distinct acceptor substrate specificities. JBiol Chem 267, 4152-4160.

Weston, B. W., Smith, P. L., Kelly, R. J., and Lowe, J. B. (1992) Molecular cloning of a fourth member of a human alpha (1,3)fucosyltransferase gene family. Multiple homologous sequences that determine expression of the Lewis x, sialyl Lewis x, and difucosyl sialyl Lewis x epitopes. JBiol Chem 267, 24575-24584.

Natsuka, S., Gersten, K. M., Zenita, K., Kannagi, R., and Lowe, J. B. (1994) Molecular cloning of a cDNA encoding a novel human leukocyte alpha-1,3-fucosyltransferase capable of synthesizing the sialyl Lewis x determinant. JBiol Chem 269, 16789-16794.

Kaneko, M., Kudo, T., Iwasaki, H., Ikehara, Y., Nishihara, S., Nakagawa, S., Sasaki, K., Shiina, T., Inoko, H., and Saitou, N. (1999) Alpha1,3-fucosyltransferase IX (Fuc-TIX) is very highly conserved between human and mouse; molecular cloning, characterization and tissue distribution of human Fuc-TIX. FEBS Lett 452.

Sasaki, K., Kurata, K., Funayama, K., Nagata, M., Watanabe, E., Ohta, S., Hanai, N., and Nishi, T. (1994) Expression cloning of a novel alpha 1,3-fucosyltransferase that is involved in biosynthesis of the sialyl Lewis x carbohydrate determinants in leukocytes. J Biol Chem 269, 14730-14737.

Kimura, H., Shinya, N., Nishihara, S., Kaneko, M., Irimura, T., and Narimatsu, H. (1997) Distinct substrate specificities of five human alpha-1,3-fucosyltransferases for in vivo synthesis of the sialyl Lewis x and Lewis x epitopes. Biochem Biophys Res Commun 237, 131-137.

Cailleau-Thomas, A., Coullin, P., Candelier, J. J., Balanzino, L., Mennesson, B., Oriol, R., and Mollicone, R. (2000) FUT4 and FUT9 genes are expressed early in human embryogenesis. Glycobiology 10, 789-802.

Niemeld, R., Natunen, J., Majuri, M.-L., Maaheimo, H., Helin, J., Lowe, J. B., Renkonen, 0., and Renkonen, R. (1998) Complementary Acceptor and Site Specificities of Fuc-TIV and Fuc-TVII Allow Effective Biosynthesis of Sialyl-TriLex and Related Polylactosamines Present on Glycoprotein Counterreceptors of Selectins. Journal of Biological Chemistry 273, 4021-4026.

Nishihara, S., Iwasaki, H., Kaneko, M., Tawada, A., Ito, M., and Narimatsu, H. (1999) a1,3-Fucosyltransferase 9 (FUT9; Fuc-TIX) preferentially fucosylates the distal GlcNAc residue of polylactosamine chain while the other four a1,3FUT members preferentially fucosylate the inner GlcNAc residue. FEBS Letters 462, 289-294.

(56) References Cited

OTHER PUBLICATIONS

Shetterly, S., Jost, F., Watson, S. R., Knegtel, R., Macher, B. A., and Holmes, E. H. (2007) Site-specific fucosylation of sialylated polylactosamines by alpha1,3/4-fucosyltransferases-V and -VI is defined by amino acids near the N terminus of the catalytic domain. JBiol Chem 282, 24882-24892.

Basu, M., Hawes, J. W., Li, Z., Ghosh, S., Khan, F. A., Zhang, B. J., and Basu, S. (1991) Biosynthesis in vitro of SA-Lex and SA-diLex by alpha 1-3 fucosyltransferases from colon carcinoma cells and embryonic brain tissues. Glycobiology 1, 527-535.

Becker, D. J., and Lowe, J. B. (2003) Fucose: biosynthesis and biological function in mammals. Glycobiology 13, 41R-53R.

Dykstra, B., Lee, J., Mortensen, L. J., Yu, H., Wu, Z. L., Lin, C. P., Rossi, D. J., and Sackstein, R. (2016) Glycoengineering of E-Selectin Ligands by Intracellular versus Extracellular Fucosylation Differentially Affects Osteotropism of Human Mesenchymal Stem Cells. Stem Cells 34, 2501-2511.

Madeira, C., Mendes, R. D., Ribeiro, S. C., Boura, J. S., Aires-Barros, M. R., da Silva, C. L., and Cabral, J. M. (2010) Nonviral gene delivery to mesenchymal stem cells using cationic liposomes for gene and cell therapy. JBiomedBiotechnol 2010, 735349.

Sackstein, R., Merzaban, J. S., Cain, D. W., Dagia, N. M., Spencer, J. A., Lin, C. P., and Wohlgemuth, R. (2008) Ex vivo glycan engineering of CD44 programs human multipotent mesenchymal stromal cell trafficking to bone. Nat Med 14, 181-187.

Geisler, C., and Jarvis, D. L. (2011) Letter to the Glyco-Forum: Effective glycoanalysis with Maackia amurensis lectins requires a clear understanding of their binding specificities. Glycobiology 21, 988-993.

Bai, X., Brown, J. R., Varki, A., and Esko, J. D. (2001) Enhanced 3-0-sulfation of galactose in Asn-linked glycans and Maackia amurenesis lectin binding in a new Chinese hamster ovary cell line. Glycobiology 11, 621-632.

Chou, M.-Y., Li, S.-C., and Li, Y.-T. (1996) Cloning and Expression of Sialidase L, a NeuAca2->3Gal-specific Sialidase from the Leech, Macrobdella decora. Journal of Biological Chemistry 271, 19219-19224.

Kumar, R., Potvin, B., Muller, W. A., and Stanley, P. (1991) Cloning of a human alpha(1,3)-fucosyltransferase gene that encodes ELFT but does not confer ELAM-1 recognition on Chinese hamster ovary cell transfectants. JBiol Chem 266, 21777-21783.

Sackstein, R. (2012) Re: Ex vivo fucosylation improves human cord blood engraftment in NOD-SCID IL-2R null mice. Experimental Hematology 40, 518-519.

Mollicone, R., Moore, S. E. H., Bovin, N., Garcia-Rosasco, M., Candelier, J.-J., Martinez-Duncker, I., and Oriol, R. (2009) Activity, Splice Variants, Conserved Peptide Motifs, and Phylogeny of Two New a1,3-Fucosyltransferase Families (FUT10 and FUT11). Journal of Biological Chemistry 284, 4723-4738.

Kumar, A., Torii, T., Ishino, Y., Muraoka, D., Yoshimura, T., Togayachi, A., Narimatsu, H., Ikenaka, K., and Hitoshi, S. (2013) The Lewis X-related a1,3-Fucosyltransferase, Fut10, is Required for the Maintenance of Stem Cell Populations. Journal of Biological Chemistry 288, 28859-28868.

Barthel, S. R., Wiese, G. K., Cho, J., Opperman, M. J., Hays, D. L., Siddiqui, J., Pienta, K. J., Furie, B., and Dimitroff, C. J. (2009) Alpha 1,3 fucosyltransferases are master regulators of prostate cancer cell trafficking. Proceedings of the National Academy of Sciences 106, 19491-19496.

Zollner, 0., and Vestweber, D. (1996) The E-selectin ligand-1 is selectively activated in Chinese hamster ovary cells by the alpha(1,3)-fucosyltransferases IV and VII. JBiol Chem 271, 33002-33008.

Huang, M. C., Laskowska, A., Vestweber, D., and Wild, M. K. (2002) The alpha (1,3)-fucosyltransferase Fuc-TIV, but not Fuc-TVII, generates sialyl Lewis X-like epitopes preferentially on glycolipids. JBiol Chem 277, 47786-47795.

R. Sackstein, C. J. Dimitroff, A hematopoietic cell L-selectin ligand that is distinct from PSGL-1 and displays N-glycan-dependent binding activity, Blood 96, 2765 (2000).

C. J. Dimitroff, J. Y. Lee, K. S. Schor, B. M. Sandmaier, R. Sackstein, Differential L-Selectin Binding Activities of Human Hematopoietic Cell L-Selectin Ligands, HCELL and PSGL-1*, J Biol Chem 276, 47623 (2001).

N. E. Good, G. D. Winget, W. Winter, T N. Conolly, S. Izawa and R. M. M. Singh, Hydrogen Ion Buffers for Biological Research, Biochemistry 5, 467 (1966).

N. E. Good, S. Izawa, Hydrogen ion buffers, Methods Enzymol. 24, 62 (1972).

Bertozzi et al., Chemical and Biological Strategies for Engineering Cell Surface Glycosylation, Annu. Rev. Cell Dev. Biol. 2001, 17:1-23.

Wu et al., Imaging specific cellular glycan structures using glycosyltransferases via click chemistry, Glycobiology, vol. 28, Issue 2, 69-79.

Donnelly C, Dykstra B, Mondal N, Huang J, Kaskow BJ, Griffin R, Sackstein R, Baecher-Allan C., Optimizing human Treg immunotherapy by Treg subset selection and E-selectin ligand expression., Sci Rep. Jan. 11, 2018;8(1):420.

Lee J, Dykstra B, Spencer JA, Kenney LL, Greiner DL, Shultz LD, Brehm MA, Lin CP, Sackstein R, Rossi DJ, mRNA-mediated glycoengineering ameliorates deficient homing of human stem cell-derived hematopoietic progenitors, J Clin Invest. Jun. 1, 2017;127(6):2433-2437.

Pachon-Pena G, Donnelly C, Ruiz-Canada C, Katz A, Fernandez-Veledo S, Vendrell J, Sackstein R., A Glycovariant of Human CD44 is Characteristically Expressed on Human Mesenchymal Stem Cells, Stem Cells. Apr. 2017;35(4):1080-1092.

Zerafaoui, et al., alpha(1,2)-fucosylation prevents sialyl Lewis x expression and E-selectin-mediated adhesion of fucosyltransferase VII-transfected cells, Eur J. Biochem. 2000, 267 pp. 53-60.

PCT/US2019/023668 International Search Report and Written Opinion dated Sep. 3, 2019.

* cited by examiner

Unsialylated type 2 lactosamine

Sialylated type 2 lactosamine

Key:
- ■ N-Acetylglucosamine (GlcNAc)
- ◆ N-Acetylneuraminic acid (Neu5Ac)
- ○ Galactose (Gal)
- ▲ Fucose

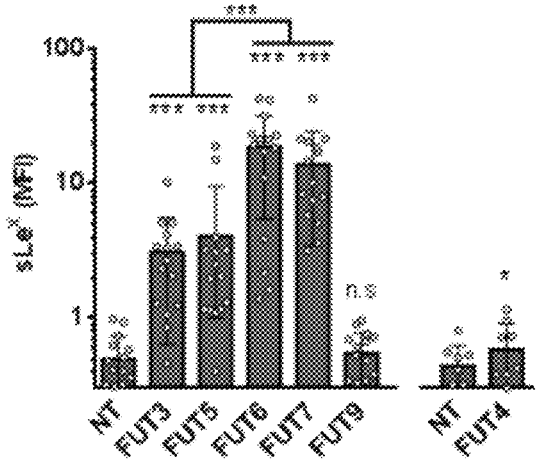

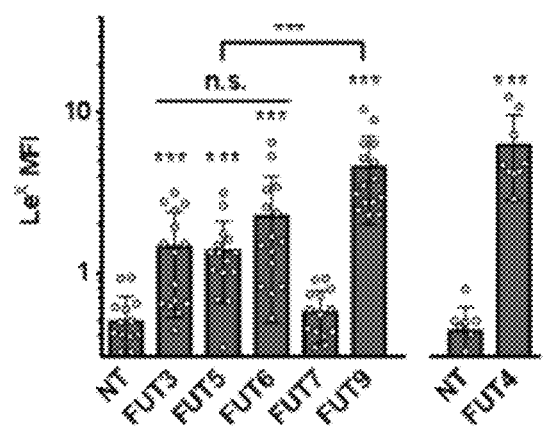

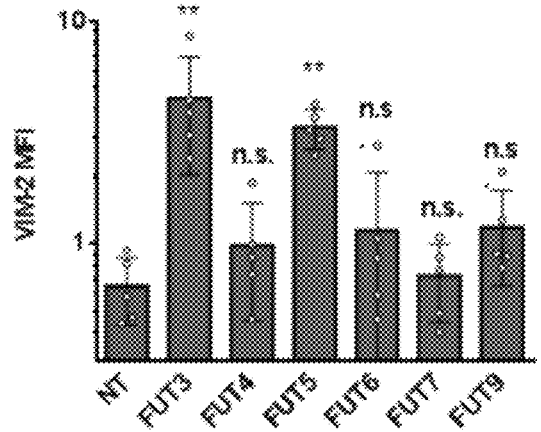

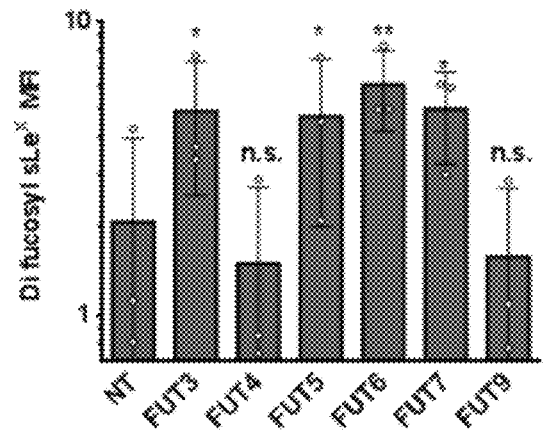
Key:
- ■ N-acetylglucosamine (GlcNAc)
- ◆ N-acetylneuraminic acid (Neu5Ac)
- ○ Galactose
- ▲ Fucose

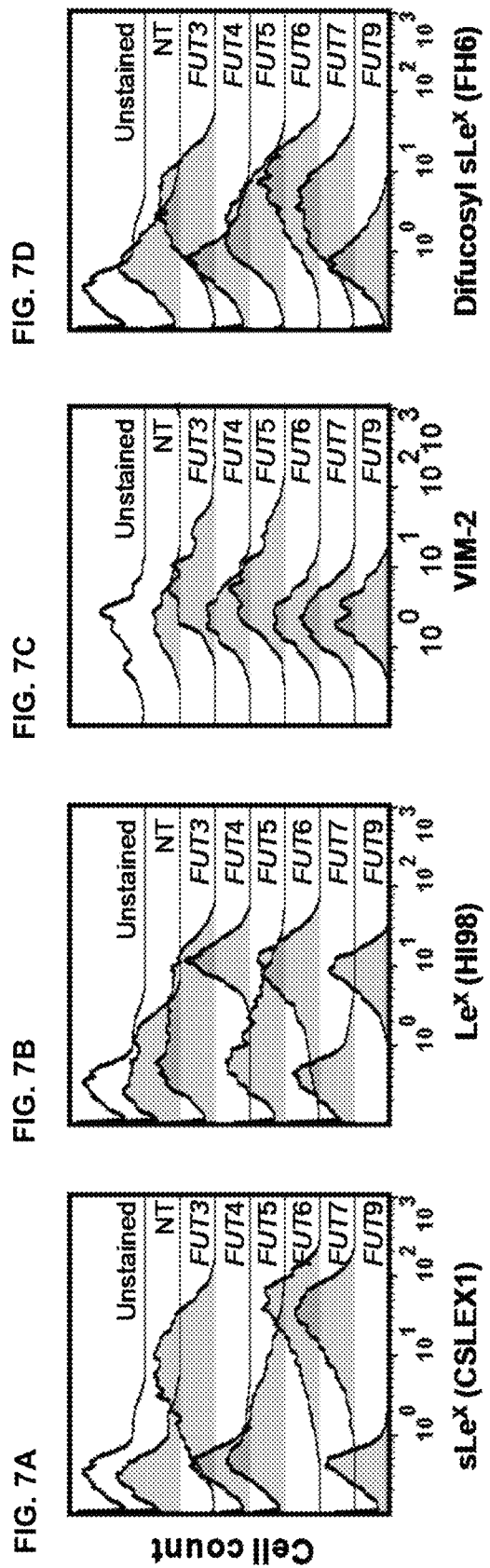

FIG. 8A

| Flow cytometry | Le$^x$ | sLe$^x$ | VIM2 | Difucosyl sLe$^x$ |
|---|---|---|---|---|
| NT | - | - | - | - |
| FUT3 | + | ++ | ++ | + |
| FUT4 | +++ | + | - | - |
| FUT5 | + | ++ | ++ | + |
| FUT6 | ++ | +++ | - | ++ |
| FUT7 | - | +++ | - | + |
| FUT9 | +++ | - | - | - |

FIG. 8B

| Mass spectrometry | Le$^x$ | | | sLe$^x$ | | | Difucosyl sLe$^x$ | | |
|---|---|---|---|---|---|---|---|---|---|
| | O-Gly | N-Gly | GSLs | O-Gly | N-Gly | GSLs | O-Gly | N-Gly | GSLs |
| NT | - | Trace | U | - | U | U | U | U | U |
| FUT3 | + | Present | Trace | ++ | Present | U | U | Present | U |
| FUT4 | +++ | Present | Present | + | Trace | U | U | U | U |
| FUT5 | + | Present | U | ++ | Present | U | U | Present | U |
| FUT6 | ++ | Present | Present | +++ | Present | Present | U | Present | U |
| FUT7 | - | >Trace | U | +++ | Present | Trace | U | Trace | U |
| FUT9 | +++ | Present | Present | - | U | U | U | U | U |

FIG. 8C

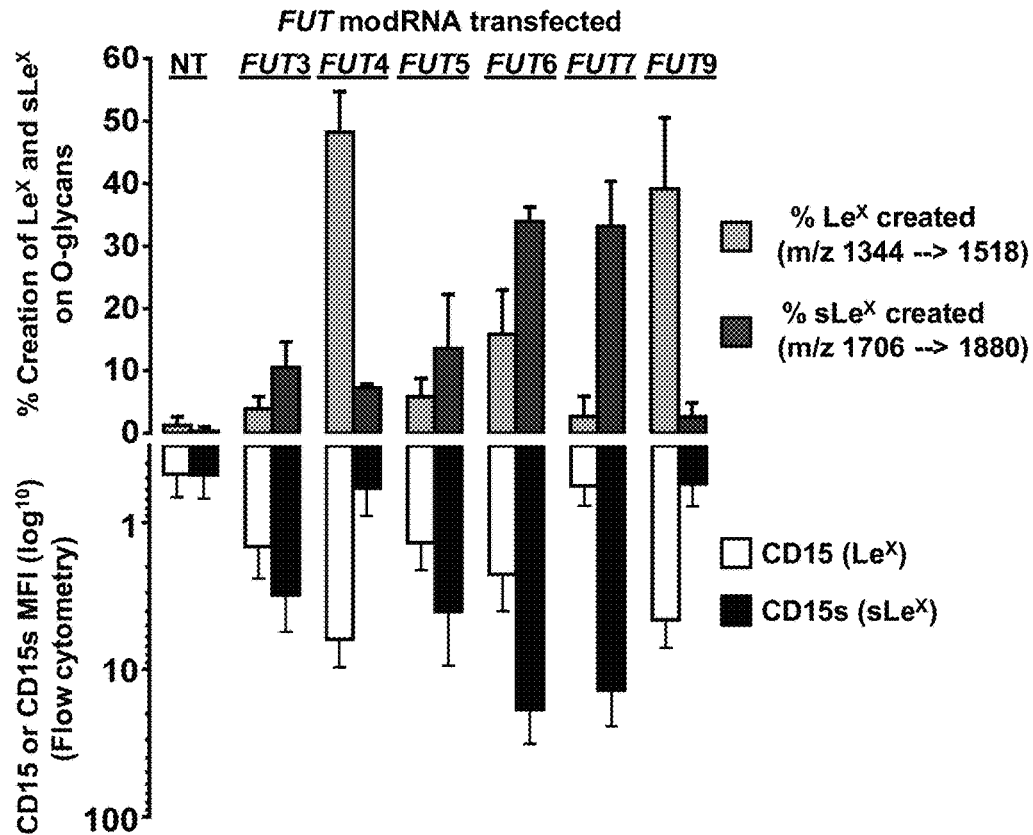

FUT6 transfected hMSCs

*FUT6* transfected hMSCs

*FUT6* transfected hMSCs

FIG. 13

List of qRT-PCR primers

| Protein | Forward Primer (5'–3') | Reverse Primer (5'–3') | Amplicon length (bp) | Reference |
|---|---|---|---|---|
| *FUT3* | GCCGACCGCAAGGTGTAC | TGACTTAGGGTTGGACATGATATCC | 75 | (Higai, Ishihara et al. 2006) |
| *FUT4*$_{COMMON}$ | GGGTTTGGATGAACTTCGAGTCG | GGTAGCCATAAGGCACAAAGACG | 123 | Origene |
| *FUT4* | AAGCCGTTGAGGCGGTTT | ACAGTTGTGTATGAGATTTGGAAGCT | 88 | (Higai, Ishihara et al. 2006) |
| *FUT4*$_{LONG}$ | TCTCGAGCCTCCTGTACCTT | GCCTCATCCGCTACTCTTGA | 150 | Primer3 |
| *FUT5* | ACCTGAGCTACTTTCACTGGCG | TCAGGTGAACCAAGCCGCTATG | 140 | Origene |
| *FUT5* | TATGGCAGTGGAACCTGTCA | CGTCCACAGCAGGATCAGTA | 100 | (Higai, Ishihara et al. 2006) |
| *FUT6* | AATGGGTCCCGCTTCCCAGACAG | GCGTCCGTACACGTCCACCTTG | 534 | (Escrevente, Machado et al. 2006) |
| *FUT6* | CCGACTACATCACCGAGAAGCT | GAACCTCTCGTAGTTGCTTCTGC | 95 | Origene |
| *FUT7* | TCCGCGTGCGACTGTTC | GTGTGGGTAGCGGTCACAGA | 65 | (Higai, Ishihara et al. 2006) |
| *FUT7* | GAATGAGAGCCGATACCAACGC | TAGCGGTCACAGATGGCACAGA | 102 | Origene |
| *FUT8* | ATCCTGATGCCTCTGCAAAC | GGGTTGGTGAGCATAAATGG | 98 | (Bernardi, Soffientini et al. 2013) |
| *FUT9* | TCCCATGCAGTTCTGATCCAT | GAAGGGTGGCCTAGCTTGCT | 78 | (Higai, Ishihara et al. 2006) |
| MGAT1 | CCTATGACCGAGATTTCCTCGC | TGAAGCTGTCCCTGCCCGTATA | 126 | OriGene |
| C2GnT1 | AACCCCTTAGTAAAGAAGAGGCG | AGCAGCTGTCAAGCATTTCA | 85 | PrimerBank |
| ST3Gal3 | GCCTGCTGAATTAGCCACCAA | GCCCACTTGCGAAAGGAGT | 144 | PrimerBank |
| ST3Gal4 | CTTCCTGCGGCTTGAGGATTA | CTCACTCCCCTTGGTCCCATA | 79 | PrimerBank |
| ST3Gal6 | ACTGCATTGCATATTATGGGGAA | TGGCTTTGATAAACAAGGCTGG | 94 | OriGene |

Two different primer sets were used to verify amplification of transcripts for some genes.

FT7 and FT9 treatment of lymphocytes- CD15, CD15s, and HECA452 staining

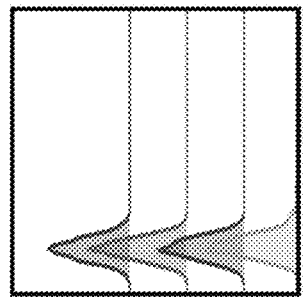

FIG. 14A

| Sample Name | Subset Name | Geometric Mean : Comp-FITC-A |
|---|---|---|
| MOUSE IGM FITC_PBMC_083.fcs | Lymphocytes | 3.38 |
| Untreated CD15_PBMC_018.fcs | Lymphocytes | 3.49 |
| FT7 CD15_PBMC_133.fcs | Lymphocytes | 4.48 |
| FT9 CD15_PBMC_158.fcs | Lymphocytes | 22.3 |

CD15

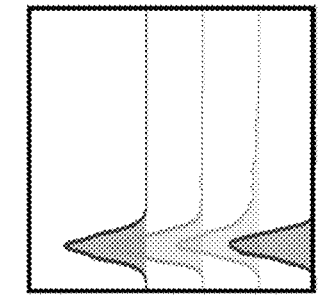

FIG. 14B

| Sample Name | Subset Name | Geometric Mean : Comp-FITC-A |
|---|---|---|
| MOUSE IGM FITC_PBMC_083.fcs | Lymphocytes | 3.38 |
| Untreated CD15S_PBMC_008.fcs | Lymphocytes | 15.7 |
| FT7 CD15S_PBMC_123.fcs | Lymphocytes | 43.3 |
| FT9 CD15S_PBMC_148.fcs | Lymphocytes | 12.0 |

CD15s

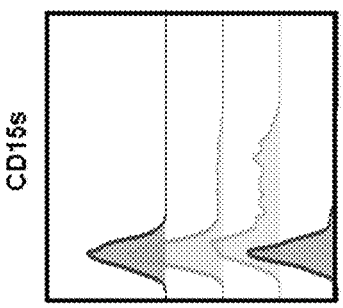

FIG. 14C

| Sample Name | Subset Name | Geometric Mean : Comp-FITC-A |
|---|---|---|
| RAT IGM FITC_PBMC_088.fcs | Lymphocytes | 4.58 |
| Untreated HECA_PBMC_013.fcs | Lymphocytes | 31.7 |
| FT7 HECA_PBMC_128.fcs | Lymphocytes | 106 |
| FT9 HECA_PBMC_153.fcs | Lymphocytes | 26.8 |

HECA-452-FITC

FT7 and FT9 treatment of lymphocytes- VIM-2 and FH6 staining

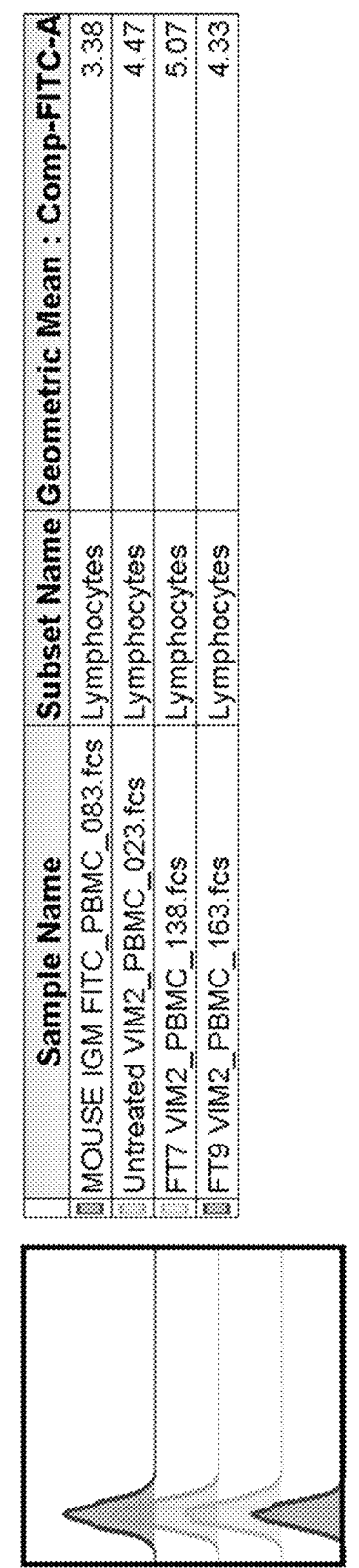

| Sample Name | Subset Name | Geometric Mean : Comp-FITC-A |
|---|---|---|
| MOUSE IGM FITC_PBMC_083.fcs | Lymphocytes | 3.38 |
| Untreated VIM2_PBMC_023.fcs | Lymphocytes | 4.47 |
| FT7 VIM2_PBMC_138.fcs | Lymphocytes | 5.07 |
| FT9 VIM2_PBMC_163.fcs | Lymphocytes | 4.33 |

VIM-2-FITC

FIG. 14D

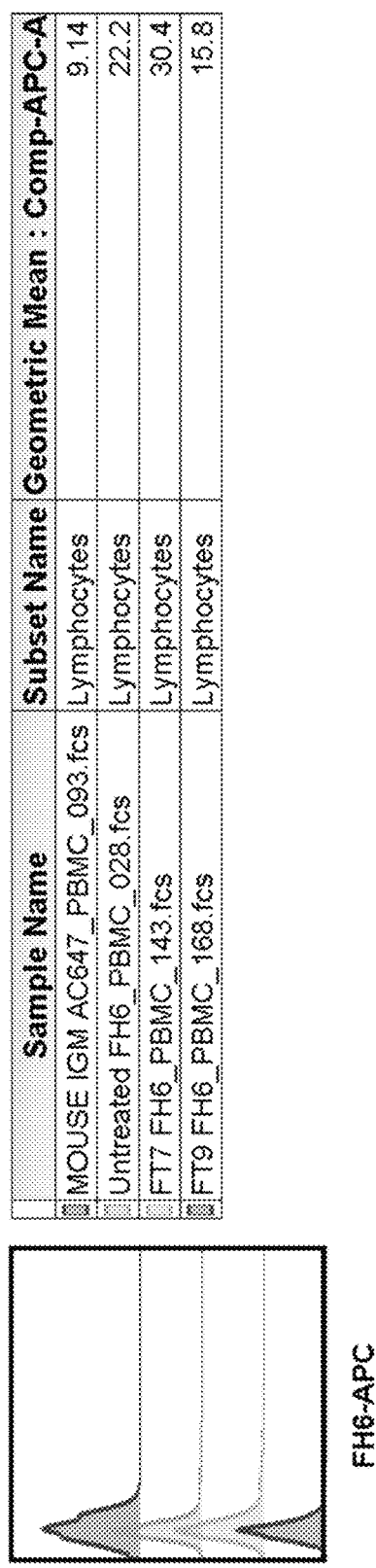

| Sample Name | Subset Name | Geometric Mean : Comp-APC-A |
|---|---|---|
| MOUSE IGM AC647_PBMC_093.fcs | Lymphocytes | 9.14 |
| Untreated FH6_PBMC_028.fcs | Lymphocytes | 22.2 |
| FT7 FH6_PBMC_143.fcs | Lymphocytes | 30.4 |
| FT9 FH6_PBMC_168.fcs | Lymphocytes | 15.8 |

FH6-APC

FIG. 14E

FT7 and FT9 treatment of Monocytes-CD15, CD15s, and HECA452 staining

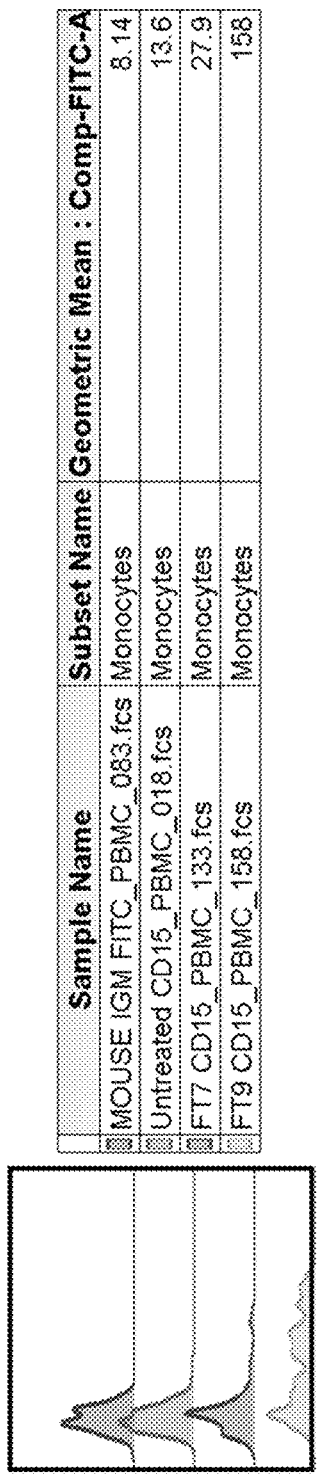

FIG. 15A

| Sample Name | Subset Name | Geometric Mean : Comp-FITC-A |
|---|---|---|
| MOUSE IGM FITC_PBMC_083.fcs | Monocytes | 8.14 |
| Untreated CD15_PBMC_018.fcs | Monocytes | 13.6 |
| FT7 CD15_PBMC_133.fcs | Monocytes | 27.9 |
| FT9 CD15_PBMC_158.fcs | Monocytes | 158 |

CD15

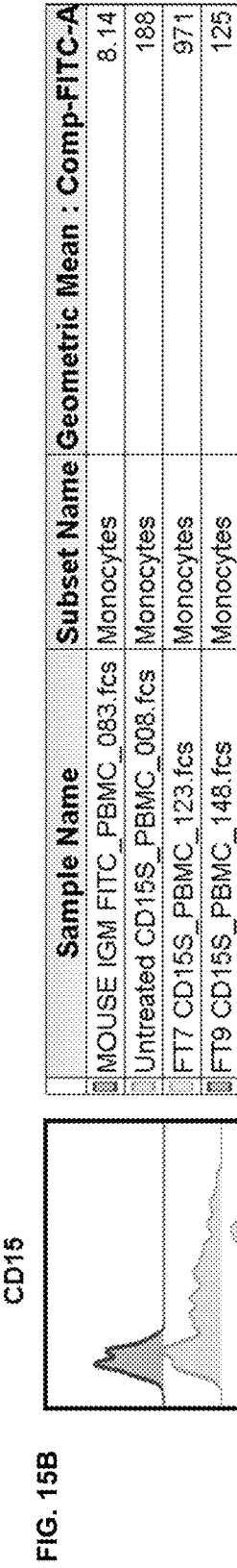

FIG. 15B

| Sample Name | Subset Name | Geometric Mean : Comp-FITC-A |
|---|---|---|
| MOUSE IGM FITC_PBMC_083.fcs | Monocytes | 8.14 |
| Untreated CD15S_PBMC_008.fcs | Monocytes | 188 |
| FT7 CD15S_PBMC_123.fcs | Monocytes | 971 |
| FT9 CD15S_PBMC_148.fcs | Monocytes | 125 |

CD15s

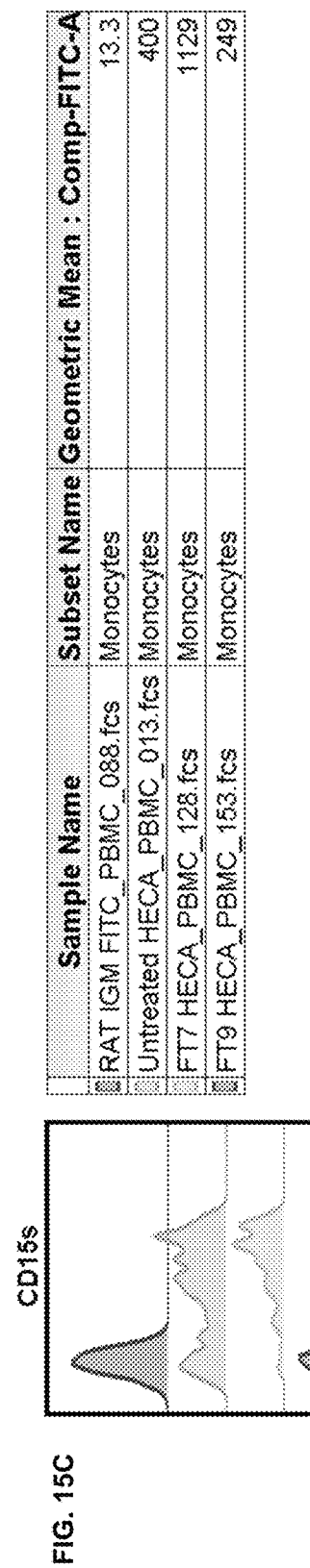

FIG. 15C

| Sample Name | Subset Name | Geometric Mean : Comp-FITC-A |
|---|---|---|
| RAT IGM FITC_PBMC_088.fcs | Monocytes | 13.3 |
| Untreated HECA_PBMC_013.fcs | Monocytes | 400 |
| FT7 HECA_PBMC_128.fcs | Monocytes | 1129 |
| FT9 HECA_PBMC_153.fcs | Monocytes | 249 |

HECA-452-FITC

FT7 and FT9 treatment of Monocytes-VIM-2 and FH6 staining

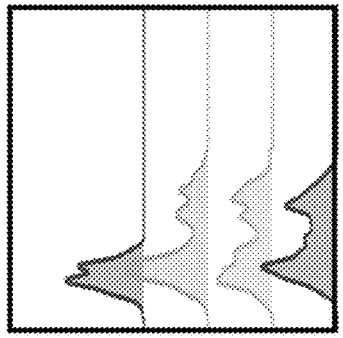

| Sample Name | Subset Name | Geometric Mean : Comp-FITC-A |
|---|---|---|
| MOUSE IGM FITC_PBMC_083.fcs | Monocytes | 8.14 |
| Untreated VIM2_PBMC_023.fcs | Monocytes | 65.6 |
| FT7 VIM2_PBMC_138.fcs | Monocytes | 78.8 |
| FT9 VIM2_PBMC_163.fcs | Monocytes | 84.1 |

VIM-2-FITC

FIG. 15D

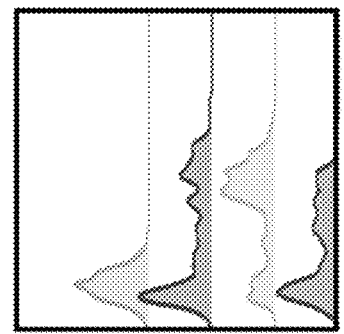

| Sample Name | Subset Name | Geometric Mean : Comp-APC-A |
|---|---|---|
| MOUSE IGM AC647_PBMC_093.fcs | Monocytes | 40.0 |
| Untreated FH6_PBMC_028.fcs | Monocytes | 221 |
| FT7 FH6_PBMC_143.fcs | Monocytes | 502 |
| FT9 FH6_PBMC_168.fcs | Monocytes | 174 |

FH6-APC

FIG. 15E

SEQUENCE LISTING

```
<160> NUMBER OF SEQ ID NOS: 14

<210> SEQ ID NO 1
<211> LENGTH: 361
<212> TYPE: PRT
<213> ORGANISM: Homo sapiens

<400> SEQUENCE: 1

Met Asp Pro Leu Gly Ala Ala Lys Pro Gln Trp Pro Trp Arg Arg Cys
1               5                   10                  15

Leu Ala Ala Leu Leu Phe Gln Leu Leu Val Ala Val Cys Phe Phe Ser
            20                  25                  30

Tyr Leu Arg Val Ser Arg Asp Asp Ala Thr Gly Ser Pro Arg Ala Pro
        35                  40                  45

Ser Gly Ser Ser Arg Gln Asp Thr Thr Pro Thr Arg Pro Thr Leu Leu
    50                  55                  60

Ile Leu Leu Trp Thr Trp Pro Phe His Ile Pro Val Ala Leu Ser Arg
65                  70                  75                  80

Cys Ser Glu Met Val Pro Gly Thr Ala Asp Cys His Ile Thr Ala Asp
                85                  90                  95

Arg Lys Val Tyr Pro Gln Ala Asp Thr Val Ile Val His His Trp Asp
            100                 105                 110

Ile Met Ser Asn Pro Lys Ser Arg Leu Pro Pro Ser Pro Arg Pro Gln
        115                 120                 125

Gly Gln Arg Trp Ile Trp Phe Asn Leu Glu Pro Pro Asn Cys Gln
    130                 135                 140

His Leu Glu Ala Leu Asp Arg Tyr Phe Asn Leu Thr Met Ser Tyr Arg
145                 150                 155                 160

Ser Asp Ser Asp Ile Phe Thr Pro Tyr Gly Trp Leu Glu Pro Trp Ser
                165                 170                 175

Gly Gln Pro Ala His Pro Pro Leu Asn Leu Ser Ala Lys Thr Glu Leu
            180                 185                 190

Val Ala Trp Ala Val Ser Asn Trp Lys Pro Asp Ser Ala Arg Val Arg
        195                 200                 205

Tyr Tyr Gln Ser Leu Gln Ala His Leu Lys Val Asp Val Tyr Gly Arg
    210                 215                 220

Ser His Lys Pro Leu Pro Lys Gly Thr Met Met Glu Thr Leu Ser Arg
225                 230                 235                 240

Tyr Lys Phe Tyr Leu Ala Phe Glu Asn Ser Leu His Pro Asp Tyr Ile
                245                 250                 255
```

```
Thr Glu Lys Leu Trp Arg Asn Ala Leu Glu Ala Trp Ala Val Pro Val
        260                 265                 270

Val Leu Gly Pro Ser Arg Ser Asn Tyr Glu Arg Phe Leu Pro Pro Asp
        275                 280                 285

Ala Phe Ile His Val Asp Asp Phe Gln Ser Pro Lys Asp Leu Ala Arg
        290                 295                 300

Tyr Leu Gln Glu Leu Asp Lys Asp His Ala Arg Tyr Leu Ser Tyr Phe
305                 310                 315                 320

Arg Trp Arg Glu Thr Leu Arg Pro Arg Ser Phe Ser Trp Ala Leu Asp
                325                 330                 335

Phe Cys Lys Ala Cys Trp Lys Leu Gln Gln Glu Ser Arg Tyr Gln Thr
            340                 345                 350

Val Arg Ser Ile Ala Ala Trp Phe Thr
            355                 360

<210> SEQ ID NO 2
<211> LENGTH: 1694
<212> TYPE: DNA
<213> ORGANISM: Homo sapiens

<400> SEQUENCE: 2
```

| | | |
|---|---|---|
| gagaaagcag gcaaccacca tgtcatttga aaacagtttc atcgggatat aattcgcaac | 60 |
| ccatacagtg aatccattta agatactctg acccatggat cccctgggtg cagccaagcc | 120 |
| acaatggcca tggcgccgct gtctggccgc actgctattt cagctgctgg tggctgtgtg | 180 |
| tttcttctcc tacctgcgtg tgtcccgaga cgatgccact ggatccccta gggctcccag | 240 |
| tgggtcctcc cgacaggaca ccactcccac ccgccccacc ctcctgatcc tgctatggac | 300 |
| atggcctttc cacatccctg tggctctgtc ccgctgttca gagatggtgc ccggcacagc | 360 |
| cgactgccac atcactgccg accgcaaggt gtacccacag gcagacacgg tcatcgtgca | 420 |
| ccactgggat atcatgtcca accctaagtc acgcctccca ccttccccga ggccgcaggg | 480 |
| gcagcgctgg atctggttca acttggagcc acccctaac tgccagcacc tggaagccct | 540 |
| ggacagatac ttcaatctca ccatgtccta ccgcagcgac tccgacatct tcacgcccta | 600 |
| cggctggctg agccgtggt ccggccagcc tgccccaccca ccgctcaacc tctcggccaa | 660 |
| gaccgagctg gtggcctggg cggtgtccaa ctggaagccg actcagcca gggtgcgcta | 720 |
| ctaccagagc ctgcaggctc atctcaaggt ggacgtgtac ggacgctccc acaagccccct | 780 |
| gcccaagggg accatgatgg agacgctgtc ccggtacaag ttctacctgg ccttcgagaa | 840 |
| ctccttgcac cccgactaca tcaccgagaa gctgtgagg aacgcccctgg aggcctgggc | 900 |
| cgtgcccgtg gtgctgggcc ccagcagaag caactacgag aggttcctgc cacccgacgc | 960 |
| cttcatccac gtgacgact tccagagccc caaggacctg gcccggtacc tgcaggagct | 1020 |
| ggacaaggac cacgcccgct acctgagcta ctttcgctgg cgggagacgc tgcggcctcg | 1080 |
| ctccttcagc tggcactgg atttctgcaa ggcctgctgg aaactgcagc aggaatccag | 1140 |
| gtaccagacg gtgcgcagca tagcggcttg gttcacctga gaggccggca tggtgcctgg | 1200 |
| gctgccggga acctcatctg cctgggggcct cacctgctgg agtcctttgt ggccaaccct | 1260 |
| ctctcttacc tgggaccctca cacgctgggc ttcacggctg ccaggagcct ctcccctcca | 1320 |
| gaagacttgc ctgctgggga cctcgcctgc tggggacctc gcctgttggg gacctcacct | 1380 |
| gctggggacc tcacctgctg ggacctggg ctgctggagg ctgcacctac tgaggatgtc | 1440 |
| ggcggtcggg gactttacct gctgggacct gctcccagag accttgccac actgaatctc | 1500 |

```
acctgctggg gacctcaccc tggagggccc tgggccctgg ggaactggct tacttggggc    1560
cccacccggg agtgatggtt ctggctgatt tgtttgtgat gttgttagcc gcctgtgagg    1620
ggtgcagaga gatcatcacg gcacggtttc cagatgtaat actgcaagga aaaaaaaaaa    1680
aaaaaaaaaa aaaa                                                      1694

<210> SEQ ID NO 3
<211> LENGTH: 530
<212> TYPE: PRT
<213> ORGANISM: Homo sapiens

<400> SEQUENCE: 3

Met Arg Arg Leu Trp Gly Ala Ala Arg Lys Pro Ser Gly Ala Gly Trp
1               5                   10                  15

Glu Lys Glu Trp Ala Glu Ala Pro Gln Glu Ala Pro Gly Ala Trp Ser
            20                  25                  30

Gly Arg Leu Gly Pro Gly Arg Ser Gly Arg Lys Gly Arg Ala Val Pro
        35                  40                  45

Gly Trp Ala Ser Trp Pro Ala His Leu Ala Leu Ala Ala Arg Pro Ala
    50                  55                  60

Arg His Leu Gly Gly Ala Gly Gln Gly Pro Arg Pro Leu His Ser Gly
65                  70                  75                  80

Thr Ala Pro Phe His Ser Arg Ala Ser Gly Glu Arg Gln Arg Arg Leu
                85                  90                  95

Glu Pro Gln Leu Gln His Glu Ser Arg Cys Arg Ser Ser Thr Pro Ala
            100                 105                 110

Asp Ala Trp Arg Ala Glu Ala Ala Leu Pro Val Arg Ala Met Gly Ala
        115                 120                 125

Pro Trp Gly Ser Pro Thr Ala Ala Gly Gly Arg Arg Gly Trp Arg
    130                 135                 140

Arg Gly Arg Gly Leu Pro Trp Thr Val Cys Val Leu Ala Ala Ala Gly
145                 150                 155                 160

Leu Thr Cys Thr Ala Leu Ile Thr Tyr Ala Cys Trp Gly Gln Leu Pro
                165                 170                 175

Pro Leu Pro Trp Ala Ser Pro Thr Pro Ser Arg Pro Val Gly Val Leu
            180                 185                 190

Leu Trp Trp Glu Pro Phe Gly Gly Arg Asp Ser Ala Pro Arg Pro Pro
        195                 200                 205

Pro Asp Cys Arg Leu Arg Phe Asn Ile Ser Gly Cys Arg Leu Leu Thr
    210                 215                 220

Asp Arg Ala Ser Tyr Gly Glu Ala Gln Ala Val Leu Phe His His Arg
225                 230                 235                 240

Asp Leu Val Lys Gly Pro Pro Asp Trp Pro Pro Trp Gly Ile Gln
                245                 250                 255

Ala His Thr Ala Glu Glu Val Asp Leu Arg Val Leu Asp Tyr Glu Glu
            260                 265                 270

Ala Ala Ala Ala Glu Ala Leu Ala Thr Ser Ser Pro Arg Pro Pro
        275                 280                 285

Gly Gln Arg Trp Val Trp Met Asn Phe Glu Ser Pro Ser His Ser Pro
    290                 295                 300

Gly Leu Arg Ser Leu Ala Ser Asn Leu Phe Asn Trp Thr Leu Ser Tyr
305                 310                 315                 320

Arg Ala Asp Ser Asp Val Phe Val Pro Tyr Gly Tyr Leu Tyr Pro Arg
                325                 330                 335
```

```
Ser His Pro Gly Asp Pro Pro Ser Gly Leu Ala Pro Pro Leu Ser Arg
            340                 345                 350

Lys Gln Gly Leu Val Ala Trp Val Val Ser His Trp Asp Glu Arg Gln
        355                 360                 365

Ala Arg Val Arg Tyr Tyr His Gln Leu Ser Gln His Val Thr Val Asp
    370                 375                 380

Val Phe Gly Arg Gly Gly Pro Gly Gln Pro Val Pro Glu Ile Gly Leu
385                 390                 395                 400

Leu His Thr Val Ala Arg Tyr Lys Phe Tyr Leu Ala Phe Glu Asn Ser
                405                 410                 415

Gln His Leu Asp Tyr Ile Thr Glu Lys Leu Trp Arg Asn Ala Leu Leu
            420                 425                 430

Ala Gly Ala Val Pro Val Val Leu Gly Pro Asp Arg Ala Asn Tyr Glu
        435                 440                 445

Arg Phe Val Pro Arg Gly Ala Phe Ile His Val Asp Asp Phe Pro Ser
    450                 455                 460

Ala Ser Ser Leu Ala Ser Tyr Leu Leu Phe Leu Asp Arg Asn Pro Ala
465                 470                 475                 480

Val Tyr Arg Arg Tyr Phe His Trp Arg Arg Ser Tyr Ala Val His Ile
                485                 490                 495

Thr Ser Phe Trp Asp Glu Pro Trp Cys Arg Val Cys Gln Ala Val Gln
            500                 505                 510

Arg Ala Gly Asp Arg Pro Lys Ser Ile Arg Asn Leu Ala Ser Trp Phe
        515                 520                 525

Glu Arg
    530

<210> SEQ ID NO 4
<211> LENGTH: 2287
<212> TYPE: DNA
<213> ORGANISM: Homo sapiens

<400> SEQUENCE: 4
gcggcagctg ctttagaagg tctcgagcct cctgtacctt cccagggatg aaccgggcct      60
tccctctgga aggcgagggt tcgggccaca gtgagcgagg ccagggcgg tgggcgcgcg      120 cagagggaaa ccggatcagt tgagagagaa tcaagagtag cggatgaggc gcttgtgggg     180
cgcggcccgg aagccctcgg cgcgggctg ggagaaggag tgggcggagg cgccgcagga     240
ggctcccggg gcctggtcgg gccggctggg ccccgggcgc agtggaagaa agggacgggc     300
ggtgcccggt tgggcgtcct ggccagctca ccttgccctg cggctcgcc ccgcccggca     360 cttgggagga gcagggcagg gcccgcggcc tttgcattct ggaccgcccc cttccattc      420 ccgggccagc ggcgagcggc agcgacggct ggagccgcag ctacagcatg agagccggtg     480
ccgctcctcc acgcctgcgg acgcgtggcg agcggaggca gcgctgcctg ttcgcgccat     540
gggggcaccg tggggctcgc cgacggcgg ggcgggcggg cggcgcgggt ggcgccgagg      600 ccggggggctg ccatggaccg tctgtgtgct ggcggccgcc ggcttgacgt gtacggcgct     660
gatcacctac gcttgctggg gcagctgcc ccgctgccc tgggcgtcgc caaccccgtc       720
gcgaccggtg gcgtgctgc tgtggtggga gcccttcggg gggcgcgata gcgcccgag       780 gccgcccct gactgccggc tgcgcttcaa catcagcggc tgccgcctgc tcaccgaccg      840
cgcgtcctac ggagaggctc aggccgtgct tttccaccac cgcgacctcg tgaaggggcc      900
ccccgactgg ccccgccct ggggcatcca ggcgcacact gccgaggagg tggatctgcg      960
```

```
cgtgttggac tacgaggagg cagcggcggc ggcagaagcc ctggcgacct ccagccccag    1020
gcccccgggc cagcgctggg tttggatgaa cttcgagtcg ccctcgcact ccccggggct    1080
gcgaagcctg gcaagtaacc tcttcaactg gacgctctcc taccgggcgg actcggacgt    1140
ctttgtgcct tatggctacc tctacccag aagccacccc ggcgacccgc cctcaggcct    1200
ggccccgcca ctgtccagga acagggggct ggtggcatgg gtggtgagcc actgggacga    1260
gcgccaggcc cgggtccgct actaccacca actgagccaa catgtgaccg tggacgtgtt    1320
cggccggggc gggccggggc agccggtgcc cgaaattggg ctcctgcaca cagtggcccg    1380
ctacaagttc tacctggctt tcgagaactc gcagcacctg gattatatca ccgagaagct    1440
ctggcgcaac gcgttgctcg ctggggcggt gccggtggtg ctgggccag accgtgccaa    1500 ctacgagcgc tttgtgcccc gcggcgcctt catccacgtg gacgacttcc caagtgcctc    1560
ctccctggcc tcgtacctgc ttttcctcga ccgcaacccc gcggtctatc gccgctactt    1620 ccactgcgc cggagctacg ctgtccacat cacctccttc tgggacgagc cttggtgccg    1680
ggtgtgccag gctgtacaga gggctgggga ccggcccaag agcatacgga acttggccag    1740
ctggttcgag cggtgaagcc gcgctcccct ggaagcgacc caggggaggc caagttgtca    1800 gcttttgat cctctactgt gcatctcctt gactgccgca tcatgggagt aagttcttca    1860
aacacccatt tttgctctat gggaaaaaaa cgatttacca attaatatta ctcagcacag    1920
agatgggggc ccggttttcca tattttttgc acagctagca attgggctcc ctttgctgct    1980
gatgggcatc attgtttagg ggtgaaggag ggggttcttc ctcaccttgt aaccagtgca    2040
gaaatgaaat agcttagcgg caagaagccg ttgaggcggt ttcctgaatt tccccatctg    2100
ccacaggcca tatttgtggc ccgtgcagct tccaaatctc atacacaact gttcccgatt    2160 cacgttttc tggaccaagg tgaagcaaat ttgtggttgt agaaggagcc ttgttggtgg    2220
agagtggaag gactgtggct gcaggtggga ctttgttgtt tggattcctc acagccttgg    2280
ctcctga                                                              2287
```

<210> SEQ ID NO 5
<211> LENGTH: 405
<212> TYPE: PRT
<213> ORGANISM: Homo sapiens

<400> SEQUENCE: 5

```
Met Gly Ala Pro Trp Gly Ser Pro Thr Ala Ala Gly Gly Arg
1               5                   10                  15

Gly Trp Arg Arg Gly Arg Gly Leu Pro Trp Thr Val Cys Val Leu Ala
            20                  25                  30

Ala Ala Gly Leu Thr Cys Thr Ala Leu Ile Thr Tyr Ala Cys Trp Gly
        35                  40                  45

Gln Leu Pro Leu Pro Trp Ala Ser Pro Thr Pro Ser Arg Pro Val
    50                  55                  60

Gly Val Leu Leu Trp Trp Glu Pro Phe Gly Gly Arg Asp Ser Ala Pro
65                  70                  75                  80

Arg Pro Pro Pro Asp Cys Arg Leu Arg Phe Asn Ile Ser Gly Cys Arg
                85                  90                  95

Leu Leu Thr Asp Arg Ala Ser Tyr Gly Glu Ala Gln Ala Val Leu Phe
                100                 105                 110

His His Arg Asp Leu Val Lys Gly Pro Pro Asp Trp Pro Pro Trp
            115                 120                 125

Gly Ile Gln Ala His Thr Ala Glu Glu Val Asp Leu Arg Val Leu Asp
```

```
        130                 135                 140
Tyr Glu Glu Ala Ala Ala Ala Glu Ala Leu Ala Thr Ser Ser Pro
145                 150                 155                 160

Arg Pro Pro Gly Gln Arg Trp Val Trp Met Asn Phe Glu Ser Pro Ser
                165                 170                 175

His Ser Pro Gly Leu Arg Ser Leu Ala Ser Asn Leu Phe Asn Trp Thr
            180                 185                 190

Leu Ser Tyr Arg Ala Asp Ser Asp Val Phe Val Pro Tyr Gly Tyr Leu
        195                 200                 205

Tyr Pro Arg Ser His Pro Gly Asp Pro Pro Ser Gly Leu Ala Pro Pro
    210                 215                 220

Leu Ser Arg Lys Gln Gly Leu Val Ala Trp Val Ser His Trp Asp
225                 230                 235                 240

Glu Arg Gln Ala Arg Val Arg Tyr Tyr His Gln Leu Ser Gln His Val
                245                 250                 255

Thr Val Asp Val Phe Gly Arg Gly Pro Gly Gln Pro Val Pro Glu
            260                 265                 270

Ile Gly Leu Leu His Thr Val Ala Arg Tyr Lys Phe Tyr Leu Ala Phe
        275                 280                 285

Glu Asn Ser Gln His Leu Asp Tyr Ile Thr Glu Lys Leu Trp Arg Asn
    290                 295                 300

Ala Leu Leu Ala Gly Ala Val Pro Val Val Leu Gly Pro Asp Arg Ala
305                 310                 315                 320

Asn Tyr Glu Arg Phe Val Pro Arg Gly Ala Phe Ile His Val Asp Asp
                325                 330                 335

Phe Pro Ser Ala Ser Ser Leu Ala Ser Tyr Leu Leu Phe Leu Asp Arg
            340                 345                 350

Asn Pro Ala Val Tyr Arg Arg Tyr Phe His Trp Arg Arg Ser Tyr Ala
        355                 360                 365

Val His Ile Thr Ser Phe Trp Asp Glu Pro Trp Cys Arg Val Cys Gln
    370                 375                 380

Ala Val Gln Arg Ala Gly Asp Arg Pro Lys Ser Ile Arg Asn Leu Ala
385                 390                 395                 400

Ser Trp Phe Glu Arg
                405

<210> SEQ ID NO 6
<211> LENGTH: 1215
<212> TYPE: DNA
<213> ORGANISM: Homo sapiens

<400> SEQUENCE: 6
atgggggcac cgtggggctc gccgacggcg gcggcgggcg gcggcgcggg gtggcgccga     60
ggccgggggc tgccatggac cgtctgtgtg ctggcggccg ccggcttgac gtgtacggcg    120
ctgatcacct acgcttgctg ggggcagctg ccgccgctgc cctgggcgtc gccaaccccg    180
tcgcgaccgg tgggcgtgct gctgtggtgg gagcccttcg gggggcgcga tagcgccccg    240
aggccgcccc ctgactgccg gctgcgcttc aacatcagcg gctgccgcct gctcaccgac    300
cgcgcgtcct acgagaggc tcaggccgtg cttttccacc accgcgacct cgtgaagggg    360 cccccccgact ggccccccgcc ctggggcatc caggcgcaca ctgccgagga ggtggatctg    420
cgcgtgttgg actacgagga ggcagcgcg cggcagaag ccctggcgac ctccagcccc    480
aggcccccgg gccagcgctg ggtttggatg aacttcgagt cgccctcgca ctccccgggg    540
```

-continued

```
ctgcgaagcc tggcaagtaa cctcttcaac tggacgctct cctaccgggc ggactcggac    600
gtctttgtgc cttatggcta cctctacccc agaagccacc ccggcgaccc gccctcaggc    660
ctggccccgc cactgtccag gaaacagggg ctggtggcat gggtggtgag ccactgggac    720
gagcgccagg cccgggtccg ctactaccac caactgagcc aacatgtgac cgtggacgtg    780
ttcggccggg gcgggccggg gcagccggtg cccgaaattg gctcctgca cacagtggcc     840 cgctacaagt ctacctggc tttcgagaac tcgcagcacc tggattatat caccgagaag     900
ctctggcgca acgcgttgct cgctggggcg gtgccggtgg tgctgggccc agaccgtgcc    960
aactacgagc gctttgtgcc ccgcggcgcc ttcatccacg tggacgactt cccaagtgcc   1020
tcctccctgg cctcgtacct gcttttcctc gaccgcaacc ccgcggtcta tcgccgctac   1080
ttccactggc gccggagcta cgctgtccac atcacctcct tctgggacga gccttggtgc   1140
cgggtgtgcc aggctgtaca gagggctggg gaccggccca agagcatacg gaacttggcc   1200
agctggttcg agcgg                                                    1215
```

<210> SEQ ID NO 7
<211> LENGTH: 374
<212> TYPE: PRT
<213> ORGANISM: Homo sapiens

<400> SEQUENCE: 7

```
Met Asp Pro Leu Gly Pro Ala Lys Pro Gln Trp Leu Trp Arg Arg Cys
1               5                   10                  15

Leu Ala Gly Leu Leu Phe Gln Leu Leu Val Ala Val Cys Phe Phe Ser
            20                  25                  30

Tyr Leu Arg Val Ser Arg Asp Asp Ala Thr Gly Ser Pro Arg Pro Gly
        35                  40                  45

Leu Met Ala Val Glu Pro Val Thr Gly Ala Pro Asn Gly Ser Arg Cys
    50                  55                  60

Gln Asp Ser Met Ala Thr Pro Ala His Pro Thr Leu Leu Ile Leu Leu
65                  70                  75                  80

Trp Thr Trp Pro Phe Asn Thr Pro Val Ala Leu Pro Arg Cys Ser Glu
                85                  90                  95

Met Val Pro Gly Ala Ala Asp Cys Asn Ile Thr Ala Asp Ser Ser Val
            100                 105                 110

Tyr Pro Gln Ala Asp Ala Val Ile Val His His Trp Asp Ile Met Tyr
        115                 120                 125

Asn Pro Ser Ala Asn Leu Pro Pro Thr Arg Pro Gln Gly Gln Arg
    130                 135                 140

Trp Ile Trp Phe Ser Met Glu Ser Pro Ser Asn Cys Arg His Leu Glu
145                 150                 155                 160

Ala Leu Asp Gly Tyr Phe Asn Leu Thr Met Ser Tyr Arg Ser Asp Ser
                165                 170                 175

Asp Ile Phe Thr Pro Tyr Gly Trp Leu Glu Pro Trp Ser Gly Gln Pro
            180                 185                 190

Ala His Pro Pro Leu Asn Leu Ser Ala Lys Thr Glu Leu Val Ala Trp
        195                 200                 205

Ala Val Ser Asn Trp Lys Pro Asp Ser Ala Arg Val Arg Tyr Tyr Gln
    210                 215                 220

Ser Leu Gln Ala His Leu Lys Val Asp Val Tyr Gly Arg Ser His Lys
225                 230                 235                 240

Pro Leu Pro Lys Gly Thr Met Met Glu Thr Leu Ser Arg Tyr Lys Phe
                245                 250                 255
```

```
Tyr Leu Ala Phe Glu Asn Ser Leu His Pro Asp Tyr Ile Thr Glu Lys
            260                 265                 270

Leu Trp Arg Asn Ala Leu Glu Ala Trp Ala Val Pro Val Leu Gly
        275                 280                 285

Pro Ser Arg Ser Asn Tyr Glu Arg Phe Leu Pro Pro Asp Ala Phe Ile
        290                 295                 300

His Val Asp Asp Phe Gln Ser Pro Lys Asp Leu Ala Arg Tyr Leu Gln
305                 310                 315                 320

Glu Leu Asp Lys Asp His Ala Arg Tyr Leu Ser Tyr Phe Arg Trp Arg
                325                 330                 335

Glu Thr Leu Arg Pro Arg Ser Phe Ser Trp Ala Leu Ala Phe Cys Lys
                340                 345                 350

Ala Cys Trp Lys Leu Gln Gln Glu Ser Arg Tyr Gln Thr Val Arg Ser
            355                 360                 365

Ile Ala Ala Trp Phe Thr
    370

<210> SEQ ID NO 8
<211> LENGTH: 1487
<212> TYPE: DNA
<213> ORGANISM: Homo sapiens

<400> SEQUENCE: 8
acagacatga gccacctcgc ccagccttt catggctgag tgatattcca ttgtgtggat        60
ggatcacact agctactctg acccatggat cccctgggcc cagccaagcc acagtggctg      120
tggcgccgct gtctggccgg gctgctgttt cagctgctgg tggctgtgtg tttcttctcc      180
tacctgcgtg tgtcccgaga cgatgccact ggatccccta ggccagggct tatggcagtg      240
gaacctgtca ccggggctcc caatgggtcc cgctgccagg acagcatggc gacccctgcc      300 cacccaccc tactgatcct gctgtggacg tggccttttta acacaccgt ggctctgccc       360 cgctgctcag agatggtgcc cggcgcggcc gactgcaaca tcactgccga ctccagtgtg      420
tacccacagg cagacgcggt catcgtgcac cactgggata tcatgtacaa ccccagtgcc      480
aacctcccgc ccccaccag gccgcagggg cagcgctgga tctggttcag catggagtcc      540
cccagcaact gccggcacct ggaagccctg gacggatact tcaatctcac catgtcctac      600
cgcagcgact ccgacatctt cacgcccat ggctggctgg agccgtggtc cggccagcct       660
gcccacccac cgctcaacct ctcggccaag accgagctgg tggcctgggc ggtgtccaac      720
tggaagccgg actcggccag ggtgcgctac taccagagcc tgcaggctca tctcaaggtg      780
gacgtgtacg acgctcccca aagcccctg cccaaggga ccatgatgga gacgctgtcc        840
cggtacaagt tctatctggc cttcgagaac tccttgcacc cgactacat cacgagaag        900 ctgtggagga acgccctgga ggcctgggc gtgcccgtgg tgctgggccc cagcagaagc       960
aactacgaga ggttcctgcc acccgacgcc ttcatccacg tggatgactt ccagagcccc     1020
aaggacctgg cccggtacct gcaggagctg acaaggacc acgcccgcta cctgagctac     1080
tttcgctggc gggagacgct gcggcctcgc tccttcagct gggcactggc tttctgcaag    1140
gcctgctgga agctgcagca ggaatccagg taccagacgt gcgcagcat gcggcttgg      1200 ttcacctgag aggccggcat ggggcctggg ctgccaggac ctcactttcc cagggcctca    1260
cctacctagg gtctcactag tcgggggatt tacctacctg ggcctcggc tgcctggggt     1320 ctcacctgcc tggggcctca cctgctggag tctttggtgg ccaggcatgt gacttacctg    1380
```

-continued

```
ggatttcact tgccgggctt cactgccagg agcctcccct gctggggacc ttgccagctg    1440
gggctgggga tggtgcctac tggggacctt gctttctgga ggctgca                  1487
```

<210> SEQ ID NO 9
<211> LENGTH: 359
<212> TYPE: PRT
<213> ORGANISM: Homo sapiens

<400> SEQUENCE: 9

```
Met Asp Pro Leu Gly Pro Ala Lys Pro Gln Trp Ser Trp Arg Cys Cys
1               5                   10                  15

Leu Thr Thr Leu Leu Phe His Leu Leu Met Ala Val Cys Phe Phe Ser
            20                  25                  30

Tyr Leu Arg Val Ser Gln Asp Asp Pro Thr Val Tyr Pro Asn Gly Ser
        35                  40                  45

Arg Phe Pro Asp Ser Thr Gly Thr Pro Ala His Ser Ile Pro Leu Ile
    50                  55                  60

Leu Leu Trp Thr Trp Pro Phe Asn Lys Pro Ile Ala Leu Pro Arg Cys
65                  70                  75                  80

Ser Glu Met Val Pro Gly Thr Ala Asp Cys Asn Ile Thr Ala Asp Arg
                85                  90                  95

Lys Val Tyr Pro Gln Ala Asp Ala Val Ile Val His His Arg Glu Val
            100                 105                 110

Met Tyr Asn Pro Ser Ala Gln Leu Pro Arg Ser Ser Arg Gln Gly
        115                 120                 125

Gln Arg Trp Ile Trp Phe Ser Met Glu Ser Pro Ser His Cys Trp Gln
    130                 135                 140

Leu Lys Ala Met Asp Gly Tyr Phe Asn Leu Thr Met Ser Tyr Arg Ser
145                 150                 155                 160

Asp Ser Asp Ile Phe Thr Pro Tyr Gly Trp Leu Glu Pro Trp Ser Gly
                165                 170                 175

Gln Pro Ala His Pro Pro Leu Asn Leu Ser Ala Lys Thr Glu Leu Val
            180                 185                 190

Ala Trp Ala Val Ser Asn Trp Gly Pro Asn Ser Ala Arg Val Arg Tyr
        195                 200                 205

Tyr Gln Ser Leu Gln Ala His Leu Lys Val Asp Val Tyr Gly Arg Ser
    210                 215                 220

His Lys Pro Leu Pro Gln Gly Thr Met Met Glu Thr Leu Ser Arg Tyr
225                 230                 235                 240

Lys Phe Tyr Leu Ala Phe Lys Asn Ser Leu His Pro Asp Tyr Ile Thr
                245                 250                 255

Glu Lys Leu Trp Arg Asn Ala Leu Glu Ala Trp Ala Val Pro Val Val
            260                 265                 270

Leu Gly Pro Ser Arg Ser Asn Tyr Glu Arg Phe Leu Pro Pro Asp Ala
        275                 280                 285

Phe Ile His Val Asp Asp Phe Gln Ser Pro Lys Asp Leu Ala Arg Tyr
    290                 295                 300

Leu Gln Glu Leu Asp Lys Asp His Ala Arg Tyr Leu Ser Tyr Phe Arg
305                 310                 315                 320

Trp Arg Glu Thr Leu Arg Pro Arg Ser Phe Ser Trp Ala Leu Ala Phe
                325                 330                 335

Cys Lys Ala Cys Trp Lys Leu Gln Glu Glu Ser Arg Tyr Gln Thr Arg
            340                 345                 350

Gly Ile Ala Ala Trp Phe Thr
```

<210> SEQ ID NO 10
<211> LENGTH: 2875
<212> TYPE: DNA
<213> ORGANISM: Homo sapiens

<400> SEQUENCE: 10

```
ggggagatca tttctctcca ttccaggaag tttgcatagc tccctggact tctgctttgc      60
actgccctgc aggagtgggt ggggaaagga agtggctttg aggcacacag aggggcttgg     120
tgaggccacc ggaggaagct tctgccacca atatgggacc tgtgcccagc ctaccagaag     180
agagcatctg aaaacatgta tcgacatggt aaccctctg cttgaagcct cacatggctc      240
cctattgcct tggtgctgaa caccctatgg ctgaccgtgg cccagcctct gcaacagctc     300
tgcctcctct ccagtggtga agaccagcc tgctgagact cctcctgcag ttcctcaaca      360
tgcctgcatt tctgctgcct cagggccttt gcgaaggttg ttccttgtaa ctggaatgcc     420
cttccatccc ttttttattc aaaaggctgc aattttaatt gaagaaagtt cccttccaag     480
gttcatgagt tgcctgactt gcccaccggt ttcctgcaag atcccttggc ctggcactta     540
gtgctcagga aatatttggt gatgggcaa ctgagtgaga aggtgggatc tggtgggaag      600
gaaagcggaa aggtagaaat tctgctcact tcctcattcc cacctcccaa ggaacccctg     660
gtgtccctgt ggaacccgct ttgggaaccg gtggttcagg tcagccttt cactttgtac      720
tcaaagccac atcgcattga agccacaggt ggggcaaggt catgcatgac ctgagtctcc     780
aaatcccttc accctgtttg gttctgcaac ggggattagg ggagcccac gatttgtttt      840
caaaggatgt ccgggctcca ggacaggatg ccctgggtca cctgatgaca ggtgtggtgg     900
ttggaaaggg cctggtttca gctccgggta cacttcctcc ttccttctgc tgcgtggtgt     960
ggcctcttcc acgtcctcag aatccagctg ttactccgtc cgcggcctct cagctctagg    1020
gccctctgca cactggcccc cccagatact ctgacccatg gatccctggg cccggccaa     1080
gccacagtgg tcgtggcgct gctgtctgac cacgctgctg tttcacctgc tgatggctgt    1140
gtgtttcttc tcctatctgc gtgtgtctca agacgatccc actgtgtacc ctaatgggtc    1200
ccgcttccca gacagcacag ggaccccgc ccactccatc cccctgatcc tgctgtggac     1260
gtggcctttt aacaaaccca tagctctgcc ccgctgctca gagatggtgc ctggcacggc    1320
tgactgcaac atcactgccg accgcaaggt gtatccacag gcagacgcgg tcatcgtgca    1380
ccaccgagag gtcatgtaca accccagtgc ccagctccca cgctcctcga ggcggcaggg    1440
gcagcgatgg atctggttca gcatggagtc cccaagccac tgctggcagc tgaaagccat    1500
ggacggatac ttcaatctca ccatgtccta ccgcagcgac tccgacatct tcacgcccta    1560
cggctggctg gagccgtggt ccggccagcc tgcccaccca ccgctcaacc tctcggccaa    1620
gaccgagctg gtggcctggg cagtgtccaa ctggggccca aactccgcca gggtgcgcta    1680
ctaccagagc ctgcaggccc atctcaaggt ggacgtgtac ggacgctccc acaagcccct    1740
gccccaggga accatgatgg agacgctgtc ccggtacaag ttctatctgg ccttcaagaa    1800
ctccttgcac cccgactaca tcaccgagaa gctgtgagg aacgccctgg aggcctgggc     1860
cgtgcccgtg gtgctgggcc ccagcagaag caactacgag aggttcctgc cgcccgacgc    1920
cttcatccac gtggacgact ccagagccc caaggacctg gccgtacc tgcaggagct       1980
ggacaaggac cacgcccgct acctgagcta ctttcgctgg cgggagacgc tgcggcctcg    2040
ctccttcagc tgggcactcg ctttctgcaa ggcctgctgg aaactgcagg aggaatccag    2100
```

-continued

```
gtaccagaca cgcggcatag cggcttggtt cacctgagag gctggtgtgg ggcctgggct    2160
gccaggaacc tcattttcct ggggcctcac ctgagtgggg gcctcatcta cctaaggact    2220
cgtttgcctg aagcttcacc tgcctgagga ctcacctgcc tgggacggtc acctgttgca    2280
gcttcacctg cctggggatt cacctacctg ggtcctcact ttcctggggc ctcacctgct    2340
ggagtcttcg gtggccaggt atgtccctta cctgggattt cacatgctgg cttccaggag    2400
cgtcccctgc ggaagcctgg cctgctgggg atgtctcctg ggactttgc ctactgggga     2460
cctcggctgt tggggacttt acctgctggg acctgctccc agagaccttc cacactgaat    2520
ctcacctgct aggagcctca cctgctgggg acctcaccct ggagggcact gggccctggg    2580
aactggcacc catggggccc cacccatgag tgatggttct ggctgatttg tttgtgatgt    2640
tgttagccgc ctgtgagggg tgcagagaga taatcaccgc accgtttcca gatgtaatac    2700
tgcaaagaaa accgatgatg aggccgggtg cggtggctca cacctgtaat cccagcactt    2760
tgggaggccg aggcaggcgg atcacaaggt caggagatcg agaccatcct ggccaatatg    2820
gtgaaacccg tctctactaa aaatacaaaa aaaaaaaaaa aaaaaaaaaa aaaaa         2875
```

<210> SEQ ID NO 11
<211> LENGTH: 342
<212> TYPE: PRT
<213> ORGANISM: Homo sapiens

<400> SEQUENCE: 11

```
Met Asn Asn Ala Gly His Gly Pro Thr Arg Arg Leu Arg Gly Leu Gly
1               5                   10                  15

Val Leu Ala Gly Val Ala Leu Ala Ala Leu Trp Leu Leu Trp Leu
            20                  25                  30

Leu Gly Ser Ala Pro Arg Gly Thr Pro Ala Pro Gln Pro Thr Ile Thr
        35                  40                  45

Ile Leu Val Trp His Trp Pro Phe Thr Asp Gln Pro Pro Glu Leu Pro
    50                  55                  60

Ser Asp Thr Cys Thr Arg Tyr Gly Ile Ala Arg Cys His Leu Ser Ala
65                  70                  75                  80

Asn Arg Ser Leu Leu Ala Ser Ala Asp Ala Val Phe His His Arg
            85                  90                  95

Glu Leu Gln Thr Arg Arg Ser His Leu Pro Leu Ala Gln Arg Pro Arg
            100                 105                 110

Gly Gln Pro Trp Val Trp Ala Ser Met Glu Ser Pro Ser His Thr His
        115                 120                 125

Gly Leu Ser His Leu Arg Gly Ile Phe Asn Trp Val Leu Ser Tyr Arg
    130                 135                 140

Arg Asp Ser Asp Ile Phe Val Pro Tyr Gly Arg Leu Glu Pro His Trp
145                 150                 155                 160

Gly Pro Ser Pro Pro Leu Pro Ala Lys Ser Arg Val Ala Ala Trp Val
                165                 170                 175

Val Ser Asn Phe Gln Glu Arg Gln Leu Arg Ala Arg Leu Tyr Arg Gln
            180                 185                 190

Leu Ala Pro His Leu Arg Val Asp Val Phe Gly Arg Ala Asn Gly Arg
        195                 200                 205

Pro Leu Cys Ala Ser Cys Leu Val Pro Thr Val Ala Gln Tyr Arg Phe
    210                 215                 220

Tyr Leu Ser Phe Glu Asn Ser Gln His Arg Asp Tyr Ile Thr Glu Lys
225                 230                 235                 240
```

```
Phe Trp Arg Asn Ala Leu Val Ala Gly Thr Val Pro Val Leu Gly
                245                 250                 255

Pro Pro Arg Ala Thr Tyr Glu Ala Phe Val Pro Ala Asp Ala Phe Val
            260                 265                 270

His Val Asp Asp Phe Gly Ser Ala Arg Glu Leu Ala Ala Phe Leu Thr
        275                 280                 285

Gly Met Asn Glu Ser Arg Tyr Gln Arg Phe Pro Ala Trp Arg Asp Arg
    290                 295                 300

Leu Arg Val Arg Leu Phe Thr Asp Trp Arg Glu Arg Phe Cys Ala Ile
305                 310                 315                 320

Cys Asp Arg Tyr Pro His Leu Pro Arg Ser Gln Val Tyr Glu Asp Leu
                325                 330                 335

Glu Gly Trp Phe Gln Ala
            340

<210> SEQ ID NO 12
<211> LENGTH: 1101
<212> TYPE: DNA
<213> ORGANISM: Homo sapiens

<400> SEQUENCE: 12
gctgactgat cctgggagac tgtggatgaa taatgctggg cacggcccca cccggaggct      60
gcgaggcttg gggtcctgg ccggggtggc tctgctcgct gccctctggc tcctgtggct     120
gctggggtca gccccctcggg gtaccccggc accccagccc acgatcacca tccttgtctg    180
gcactggccc ttcactgacc agcccccaga gctgcccagc gacacctgca cccgctacgg    240
catcgcccgc tgccacctga gtgccaaccg aagcctgctg gccagcgccg acgccgtggt    300
cttccaccac cgcgagctgc agacccgcgc gtcccacctg ccctggccc agcggccgcg    360
agggcagccc tgggtgtggg cctccatgga gtctcctagc cacacccacg gcctcagcca    420
cctccgagc atcttcaact gggtgctgag ctaccggcgc gactcggaca tctttgtgcc    480
ctatggccgc ctggagcccc actgggggcc ctcgccaccg ctgccagcca gagcagggt    540
ggccgcctgg gtggtcagca acttccagga gcggcagctg cgtgccaggc tgtaccggca    600
gctggcgcct catctgcggg tggatgtctt tggccgtgcc aatggacggc cactgtgcgc    660
cagctgcctg gtgcccaccg tgcccagta ccgcttctac ctgtcctttg agaactctca    720
gcaccgcgac tacattacgg agaaattctg cgcaacgca ctggtggctg gcactgtgcc    780
agtggtgctg gggccccac gggccaccta tgaggccttc gtgccggctg acgccttcgt    840
gcatgtggat gactttggct cagcccgaga gctggcggct ttcctcactg gcatgaatga    900
gagccgatac caacgcttct ttgcctggcg tgacaggctc cgcgtgcgac tgttcaccga    960
ctggcgggaa cgtttctgtg ccatctgtga ccgctaccca cacctacccc gcagccaagt   1020
ctatgaggac cttgaggtt ggtttcaggc ctgagatccg ctggccgggg gaggtgggtg    1080
tgggtggaag ggctgggtgt c                                              1101

<210> SEQ ID NO 13
<211> LENGTH: 359
<212> TYPE: PRT
<213> ORGANISM: Homo sapiens

<400> SEQUENCE: 13

Met Thr Ser Thr Ser Lys Gly Ile Leu Arg Pro Phe Leu Ile Val Cys
1               5                   10                  15
```

Ile Ile Leu Gly Cys Phe Met Ala Cys Leu Leu Ile Tyr Ile Lys Pro
            20                  25                  30

Thr Asn Ser Trp Ile Phe Ser Pro Met Glu Ser Ala Ser Ser Val Leu
        35                  40                  45

Lys Met Lys Asn Phe Phe Ser Thr Lys Thr Asp Tyr Phe Asn Glu Thr
50                  55                  60

Thr Ile Leu Val Trp Val Trp Pro Phe Gly Gln Thr Phe Asp Leu Thr
65                  70                  75                  80

Ser Cys Gln Ala Met Phe Asn Ile Gln Gly Cys His Leu Thr Thr Asp
                85                  90                  95

Arg Ser Leu Tyr Asn Lys Ser His Ala Val Leu Ile His His Arg Asp
            100                 105                 110

Ile Ser Trp Asp Leu Thr Asn Leu Pro Gln Gln Ala Arg Pro Pro Phe
            115                 120                 125

Gln Lys Trp Ile Trp Met Asn Leu Glu Ser Pro Thr His Thr Pro Gln
130                 135                 140

Lys Ser Gly Ile Glu His Leu Phe Asn Leu Thr Leu Thr Tyr Arg Arg
145                 150                 155                 160

Asp Ser Asp Ile Gln Val Pro Tyr Gly Phe Leu Thr Val Ser Thr Asn
                165                 170                 175

Pro Phe Val Phe Glu Val Pro Ser Lys Glu Lys Leu Val Cys Trp Val
            180                 185                 190

Val Ser Asn Trp Asn Pro Glu His Ala Arg Val Lys Tyr Tyr Asn Glu
            195                 200                 205

Leu Ser Lys Ser Ile Glu Ile His Thr Tyr Gly Gln Ala Phe Gly Glu
210                 215                 220

Tyr Val Asn Asp Lys Asn Leu Ile Pro Thr Ile Ser Ala Cys Lys Phe
225                 230                 235                 240

Tyr Leu Ser Phe Glu Asn Ser Ile His Lys Asp Tyr Ile Thr Glu Lys
                245                 250                 255

Leu Tyr Asn Ala Phe Leu Ala Gly Ser Val Pro Val Val Leu Gly Pro
            260                 265                 270

Ser Arg Glu Asn Tyr Glu Asn Tyr Ile Pro Ala Asp Ser Phe Ile His
            275                 280                 285

Val Glu Asp Tyr Asn Ser Pro Ser Glu Leu Ala Lys Tyr Leu Lys Glu
290                 295                 300

Val Asp Lys Asn Asn Lys Leu Tyr Leu Ser Tyr Phe Asn Trp Arg Lys
305                 310                 315                 320

Asp Phe Thr Val Asn Leu Pro Arg Phe Trp Glu Ser His Ala Cys Leu
                325                 330                 335

Ala Cys Asp His Val Lys Arg His Gln Glu Tyr Lys Ser Val Gly Asn
            340                 345                 350

Leu Glu Lys Trp Phe Trp Asn
        355

<210> SEQ ID NO 14
<211> LENGTH: 2565
<212> TYPE: DNA
<213> ORGANISM: Homo sapiens

<400> SEQUENCE: 14
ggcgaagccg agatgggca gagagcgcgc gcggcgcagc agctccagat tcactgctct      60
cccctgcagc tccccgcgcc ccgccgctg tcgctgcctc ggtgtccccc agccccagtc     120
gcgctcttag gacagcgccg ccaccgccgc ctggccctgc ctgcctcctg cgccgcgcag    180

-continued

```
ccctcgcgag cgccccggaa ggcgctttac ccctaggacc gatttagaat gtaataactc      240
aaggatttga taatacagtg aagtagtata acaactgtct acgtgcttcc catgatatgt      300
tctctatatt gaaaaattat gacatcaaca tccaaaggaa ttcttcgccc attttttgatt     360 gtctgcatta tcctgggctg tttcatggca tgtcttctca tttacatcaa acctaccaac     420
agctggatct tcagtccaat ggaatcagcc agctctgtgc tgaaaatgaa aaacttctttt    480 tccaccaaaa ctgattattt taatgaaact actattctgg tgtgggtgtg gccatttggg     540
cagacctttg accttacatc ctgccaagca atgttcaaca tccaaggatg ccatctcaca     600
acggaccgtt cactgtacaa caaatcccat gcagttctga tccatcaccg agacatcagt     660
tgggatctga caaatttacc tcagcaagct aggccaccct tccagaaatg gatttggatg     720
aatttggaat caccaactca cactccccaa agagtggca ttgagcactt gtttaacctg      780
actctgactt accgccgtga ttcagatatc caagtgcctt atggcttctt gacggtaagc     840
acaaatccct tcgtgtttga agtgccaagc aaagagaaat tggtgtgctg ggttgtgagt     900
aactggaacc ctgagcatgc cagagtcaag tattacaatg agctaagcaa aagcattgaa     960
atccatacct acgggcaagc atttggagaa tatgtcaatg ataaaaattt gattcctacc    1020
atatctgctt gtaaatttta tcttttccttt gaaaattcaa tccacaagga ttacatcacg    1080
gaaaagctat acaatgcttt tctggctggc tctgtacctg ttgttctggg accatctagg     1140
gaaaactatg agaattatat tccagcagat tcattcattc atgtggaaga ttataactct    1200
cccagtgagc tagcaaagta tctgaaggaa gtcgacaaaa acaataagtt ataccttagt    1260
tactttaact ggaggaagga tttcactgta aatcttccac gattttggga atcacatgca    1320
tgtttggctt gcgatcatgt gaaaaggcat caagaatata agtctgttgg taatttagag    1380
aaatggtttt ggaattaaaa ttttttcatca cttgcacact tgataaatat tttgatgaga    1440
tatcatccaa gtattgagga taagaagaga tgcaacatac tactttttgtg tcacaattta    1500 tttttatcac cctctctagg gtaacgtgta tattttggtg gagattttta aaagctcagc    1560
atgagcaatc attccattcg gttttaaatt atcctgtata tacctaatta tgtgcactgg    1620
agagtaattt attcttcatt atcatttgta aacattgctt tttcacattt ttgtagttgt    1680
ccataatgta agcttgtggt ttgattattg tttccacact gatcagctgt ttaatctatt    1740
tgggaaatga agatgcacat cttaaagtat gtaaaatttt cactaagtat tacaatgtct    1800
agttccaact ttgcatacta taacagagga agaacatgtt gcgattgaat tctaaccttct   1860 ttgactccta agatgaatga agtgtataac tgtctctatt tgatctattt tttttacctg    1920
tttatcacat ttgtgaaggt gaaattattc atggagtgaa taagaaagat atgaagcaga    1980
actgttctat tcaggaagct attagacttc tcatttatttt tcattaagct gatttgcagc    2040
tacttattct catggtctta aattaaatta ttcaagtatt tttaaatatc caatttgttg    2100 tgatttcag cacctgggaa gtaatcccaa taatacttta gaaaatctaa gacagttctt      2160
tctgctactg atgacactca ttgtcataat aaaacaaata atttcctcaa ataacaaaga    2220
aaaatgatac ctataaatat atttataaat ggtgtcattt atgaacaatg tttaattatg    2280
tatcaattta agattttttt ctgaagccct aatatttaaa atggccttat tttaccatat    2340
ggatataaga tttggctcat aatgatgagc cctatcattt gatttgagtt ctatcattta    2400
```

```
agagagccta actaaaatta tcatcaaggt attaaatata agacgttaaa tataataaag    2460
tggggatata tagaaaacac acagtgttag cacagagtaa gatctcaatg cacatttgtt    2520
ggatgaataa ataaatgcaa ttgaattccc aaaaaaaaaa aaaaa                     2565
```

COMPOSITIONS AND METHODS FOR ENFORCING FUCOSYLATION OF LACTOSAMINYL GLYCANS IN HUMAN CELLS WITH ALPHA(1,3)-FUCOSYLTRANSFERASES

CROSS REFERENCE TO RELATED APPLICATIONS

The present application is a continuation of International Application No. PCT/US2019/023668 filed on Mar. 22, 2019, which claims benefit of U.S. Provisional Patent Application Ser. No. 62/647,404 filed on Mar. 23, 2018, which applications are incorporated by reference herein in their entirety.

GOVERNMENT FUNDING

This invention was made with government support under grants PO1 HL107146 awarded by the National Institutes of Health. The government has certain rights in this invention.

FIELD OF THE INVENTION

This disclosure relates to improved compositions and methods for enforcing a distinct pattern of fucosylated lactosaminyl glycans on a cell. In some embodiments, a distinct pattern of monosaccharides in stereospecific linkages, such as α(1,3)-fucosylated lactosaminyl glycans, are enforced on a living cell surface, whether or not the cell originally had α(1,3)-fucosylated lactosaminyl glycans. In other embodiments, stereospecific addition of a molecular tag-modified donor nucleotide fucose allows for subsequent linkage of other molecules onto the installed fucose in a distinct pattern onto cell surface lactosaminyl glycans. In other embodiments, molecules containing distinct biologic properties can be covalently linked to the donor nucleotide fucose and can thus be stereospecifically added in a distinct pattern onto cell surface lactosaminyl glycans. In other embodiments, the distinct patterns of expression of fucosylated lactosamines installed on the cell surface by contacting cells with one or more α(1,3)-fucosyltransferases can be used to characterize and isolate defined cell subsets within a heterogenous mixture of cells.

INCORPORATION BY REFERENCE OF SEQUENCE LISTING

This application contains references to amino acids and/or nucleic acid sequences that have been filed concurrently herewith as sequence listing text file "SEQUENCE LISTING.txt", file size of 42 KB, created on Mar. 20, 2018. The aforementioned sequence listing is hereby incorporated by reference in its entirety pursuant to 37 C.F.R. § 1.52(e)(5).

BACKGROUND OF THE INVENTION

Custom-Modification of Glycans on a Cell Surface, on a Given Protein, or on a Given Lipid In mammals, every cell of the body is covered with a sugar coat. Moreover, almost every protein and every lipid found on the cell surface, and those found within the extracellular fluids (e.g., blood), contains sugar modifications. These sugar decorations (which comprise a subset of "post-translational modifications") impart key biologic effects on both the cell surface, and on each individual lipid (i.e., glycolipid) and protein (i.e., glycoprotein). Indeed, several key biologic effects are exclusively mediated by glycan determinants/composition. For example, the amount of sialic acid found on the surface of a blood leukocyte or a platelet dictates whether that cell will be destroyed (cleared) by the reticulo-endothelial system. Similarly, the sialic acid content of a glycoprotein dictates the half-life of that protein in circulation, with more sialylation generally yielding a longer half-life. Besides sialylation, the content and location of fucoses on the cell surface or on a particular glycoprotein imparts critical biology. For example, fucosylation of the Fc portion of antibodies dampens the ability of the antibody to participate in antibody-dependent cell-mediated cytotoxicity (ADCC). Thus, it is evident that the capacity to install a desired type or amount or a desired ratio of certain sugar structures can impart critical biologic effects on a cell, on a protein, or on a lipid. In many cases, the discrete compositional combination and relevant linkages (i.e., stereospecific localization) of certain monosaccharides (i.e, core sugar units) covalently clustered into oligosaccharides or polysaccharides imparts a certain biologic property. To achieve the intended biologic effect, therefore, it is necessary to custom-modify the creation of that target oligosaccharide and/or polysaccharide motif on the surface of a given cell, on a given (glyco)protein, or on a given (glyco)lipid. As such, the ability to stereospecifically install a requisite quantity of one or more pertinent monosaccharides, or of an oligosaccharide/polysaccharide motif or a desired combination of various oligosaccharide/polysaccharide motifs on a given cell, glycolipid or glycoprotein, is highly desired. Moreover, the capacity to install a distinct pattern of a given monosaccharide moiety allows for placement of larger molecular assemblies onto the installed monosaccharide, either via use of a chemical tag motif placed on the donor monosaccharide itself or as a molecular complex covalently attached to the donor monosaccharide moiety. Lastly, the capacity of a cell to undergo monosaccharide modification(s) to yield creation of a given glycan determinant is a reflection of the inherent "glycosignature" of that cell; as such, stratification of cells on the basis of the relative amount and extent of a given glycan determinant that is engendered by monosaccharide installation is useful for identifying distinct subsets of cells.

Directing the Migration of Blood-Borne Cells into Tissue

The success of cell-based therapeutics (also known as "adoptive cellular therapeutics") depends on getting the relevant cells to the site(s) where they are needed in sufficient amount(s) to achieve intended biologic effect(s). Delivery of cells for clinical indications can be achieved by direct (local) injection into involved tissue(s), by intravascular administration (e.g., systemically or by catheter-based delivery to a particular vascular bed), or by application/placement of cells directly onto the affected area (e.g., for skin ulcers, burns, etc.). In all forms of cell administration, it would be advantageous for administered cells to possess membrane molecules that would promote lodgement of the cell within the administered site precisely within tissue microenvironments that are critical to achieve intended effect, e.g., control of inflammation, tissue repair, elimination of rejection, eradication of cancer, etc. One such microenvironmental site are the "perivascular areas" present in and around microvessels within an injured tissue, as it is well known that integrity of the microvasculature, and production of new microvessels ("angiogenesis"), is a critical prerequisite to tissue regeneration/repair. Indeed, at all sites of tissue injury, inflammation, and cancer, endothelial cells within the microvessels of affected tissue(s) display a characteristic set of adhesion molecules that serve a key role in recruitment of circulating (blood-borne) cells to the target site. These endothelial molecules are upregulated by inflammatory cytokines such as tumor necrosis factor (TNF) and interleukin 1 (IL-1), and, in humans include the molecule E-selectin, and, in mouse, the molecules E-selectin and P-selectin, which are lectins belonging to a family of adhesion molecules known as "selectins" (to be described in more detail below). In addition, leukocytes that have been recruited to any inflammatory site (including cancer) or to a site of tissue injury/damage display L-selectin, the "leukocyte" selectin, and, therefore, expression of ligands for L-selectin on administered cells would promote lodgement of such cells to regions of leukocyte infiltrates within the affected tissue(s).

At first glance, direct delivery might seem to be the most efficient approach to cell administration, especially considering that a concentrated bolus of cells could be applied to an affected area. However, there are situations where local injection may actually be counterproductive to intended therapeutic effects, and, moreover, local injection is practical for only certain anatomic locations: (1) By introducing pertinent cells in media suspension under hydrostatic pressure, the injection procedure could harm the delivered cells and, furthermore, could further compromise tissue integrity and disrupt incipient tissue repair and/or host defense processes, thereby exacerbating the inflammatory condition or counteracting appropriate immune reactions in situ; (2) By virtue of being an invasive method, the injection needle/device (and the suspension solution) could induce target tissue damage and/or instigate collateral tissue damage; (3) Direct injection is most feasible for organs/tissues with well-defined anatomic boundaries (e.g., the heart), and is impractical for tissues without extensive connective tissue support (e.g., the lung); (4) The injection procedure could be technologically demanding and labor-intensive, requiring use of sophisticated delivery systems with substantial imaging support, especially for relatively inaccessible and/or fragile organs/tissues (e.g., the central nervous system); (5) Most importantly, many degenerative and inflammatory conditions are widely distributed and multifocal in nature (e.g., osteoporosis, inflammatory bowel disease, multiple sclerosis, etc.), and thus direct injection is neither practical nor effective. Thus, though there are clinical conditions/situations in which local injection is feasible, the vascular route of administration is mandated for all generalized "systemic" disorders, as well as for any tissue with problematic access and/or anatomy not amenable to local injection (e.g., the pancreas in diabetes, the lung in chronic obstructive pulmonary disease). The capacity to administer cells repeatedly with minimal effort is another important practical advantage of systemic infusion. Therefore, creation of methodologies to optimize the expression/activity of molecular effectors directing both the adhesion/lodgement of directly injected cells within the inflammatory milieu and the physiologic migration of intravascularly administered cells to the affected site(s) is key to achieving the tremendous promise of all cell-based therapeutics.

The capacity to direct migration of blood-borne cells to a predetermined location ("homing") has profound implications for a variety of physiologic and pathologic processes. Recruitment of circulating cells to a specific anatomic site is initiated by discrete adhesive interactions between cells in flow and vascular endothelium at the target tissue(s). The molecules that mediate these contacts are called "homing receptors," and, as defined historically, these structures pilot tropism of cells in blood to the respective target tissue. Historically, three "tissue-specific homing receptors" were described: L-selectin for peripheral lymph nodes, $\alpha_4\beta_7$ (LPAM-1) for intestines and gut-associated lymphoid tissue, and a specialized sialofucosylated glycoform of the molecule P-selectin Glycoprotein Ligand-1 (PSGL-1) known, specifically, as the "Cutaneous Lymphocyte Antigen" (CLA) that promotes cell migration to skin (90). Notably, apart from these tissues, it had been recognized for several decades that circulating cells, especially hematopoietic stem cells (HSCs), navigate effectively to bone marrow (91), and several studies pointed to a role for selectins, predominantly E-selectin binding to HSC E-selectin ligands, in mediating recruitment of HSCs to marrow.

From a biophysical perspective, a homing receptor functions as a molecular brake, effecting initial tethering then sustained rolling contacts of cells in blood flow onto the vascular endothelium at velocities below that of the prevailing bloodstream (Step 1) (90). Thereafter, a cascade of events ensue, typically potentiated by chemokines, resulting in activation of integrin adhesiveness (Step 2), firm adherence (Step 3) and endothelial transmigration (Step 4) (92). This "multi-step paradigm" holds that tissue-specific migration is regulated by a discrete combination of homing receptor and chemokine receptor expression on a given circulating cell, allowing for recognition of a pertinent "traffic signal" displayed by the relevant vascular adhesive ligands and chemokines expressed within target endothelium in an organ-specific manner. Following engagement of homing receptor(s) directing trafficking of cells to bone marrow, several lines of evidence indicate that one chemokine in particular, SDF-1 (CXCL12), plays an essential role in Step 2-mediated recruitment of cells to this site (91; 93; 94). However, expression of SDF-1 is not limited to the marrow, and this chemokine is typically expressed at all sites of tissue injury/inflammation (95).

The most efficient effectors of Step 1 rolling interactions are the selectins (E-, P- and L-selectin) and their ligands (90). As the name implies, selectins are lectins that bind to specialized carbohydrate determinants, consisting of sialofucosylations containing an $\alpha(2,3)$-linked sialic acid substitution(s) and an $\alpha(1,3)$-linked fucose modification(s) prototypically displayed as the tetrasaccharide sialyl Lewis X (sLe$^x$; Neu5Ac$\alpha$2-3Gal$\beta$1-4[Fuc$\alpha$1-3]GlcNAc$\beta$1-R)) (90; 96). The sLe$^X$ glycan is recognized by a variety of monoclonal antibodies (mAbs), including the mAb known as "CSLEX-1" and another mAb known as "HECA452." Compared to HECA452, the CSLEX-1 mAb has a more restricted specificity in that it recognizes only sLe$^X$, whereas HECA452 recognizes both sLe$^X$ and the isomeric sialofucosylated type 1 lactosaminyl glycan known as sialylated Lewis A (sLe$^A$). E- and P-selectin are expressed on vascular endothelium (P-selectin also on platelets), and L-selectin is expressed on circulating leukocytes (90). E- and P-selectin are typically inducible endothelial membrane molecules that are prominently expressed only at sites of tissue injury and inflammation, where their expression is generated in response to inflammatory cytokines. However, the microvasculature of bone marrow and skin constitutively expresses these selectins, and they play a key role in steady-state recruitment of blood-borne cells to these sites (15). Importantly, within all inflammatory sites and sites of tissue injury/damage in primates (but not rodents), E-selectin is the principal vascular selectin mediating cell recruitment, as the promoter element responsive to the inflammatory cytokines TNF and IL-1 has been deleted from the P-selectin gene. Thus, at all inflammatory sites of humans, vascular E-selectin expression is more pronounced than that of P-selectin (95).

Two principal ligands for E-selectin have been identified on human hematopoietic stem/progenitor cells (HSPC), the highly sialofucosylated "CLA" glycoform of PSGL-1 (97, 95) and a specialized sialofucosylated CD44 glycoform known as Hematopoietic Cell E-/L-selectin Ligand (HCELL) (98, 99). CD44 is a rather ubiquitous cell membrane protein, but the HCELL phenotype is found predominantly on human HSPCs. In contrast to HCELL's restricted distribution, CLA/PSGL-1 is widely expressed among hematopoietic progenitors and more mature myeloid and lymphoid cells within the marrow (97, 95). HCELL is operationally defined as CD44 that binds to E-selectin and L-selectin under shear conditions, and is identified by Western blot analysis of cell lysates as a CD44 glycoform reactive with E-selectin-Ig chimera (E-Ig) and with mAb 452, which recognizes sialyl Lewis X (and, as noted above, in addition to $sLe^X$, HECA452 recognizes the tetrasaccharide isomer of $sLe^X$ known as a "sialylated Lewis a" ($sLe^A$) in which fucose is attached in $\alpha(1,4)$-linkage to N-acetylglucosamine within a type 1 lactosamine backbone). In addition to CLA and HCELL, human leukocytes and HSPCs can also express a CD43 glycoform known as "CD43-E" which can serve as an E-selectin ligand (100, 16), and, in mouse leukocytes, another E-selectin ligand known as E-selectin Ligand-1 (ESL-1) has been described (16). In all glycoprotein selectin ligands (e.g., CD43-E, CLA, and HCELL) binding to E-selectin (and, also, to L-selectin and P-selectin) is critically dependent on $\alpha(2,3)$-sialic acid and $\alpha(1,3)$-fucose modifications (98; 99; 101; 102). On human HSPCs, HCELL displays the pertinent sialofucosylated selectin binding determinants on N-glycans (103; 101). In vitro assays of E- and L-selectin binding under hemodynamic shear stress indicate that HCELL is the most potent ligand for these molecules expressed on any human cell (98; 102). Importantly, though E-selectin is constitutively expressed on microvascular endothelium of the marrow and skin, this molecule is prominently expressed on endothelial beds at all sites of inflammation—both acute and chronic types—regardless of whether it is induced by direct tissue injury (e.g., burns, trauma, decubitus ulcers, etc.), ischemic/vascular events (e.g., myocardial infarct, stroke, shock, hemorrhage, coagulopathy, etc.), infections (e.g., cellulitis, pneumonia, meningitis, SIRS, etc.), neoplasia (e.g., breast cancer, lung cancer, lymphoma, etc.), immunologic/autoimmune conditions (e.g., graft vs. host disease, multiple sclerosis, diabetes, inflammatory bowel disease, lupus erythematosus, rheumatoid arthritis, psoriasis, etc.), degenerative diseases (e.g., osteoporosis, osteoarthritis, Alzheimer's disease, etc.), congenital/genetic diseases (e.g., muscular dystrophies, lysosomal storage diseases, Huntington's disease, etc.), adverse drug effects (e.g., drug-induced hepatitis, drug-induced cardiac injury, etc.), toxic injuries (e.g., radiation exposure(s), chemical exposure(s), alcoholic hepatitis, alcoholic pancreatitis, alcoholic cardiomyopathy, cocaine cardiomyopathy, etc.), metabolic derangements (e.g., uremic pericarditis, metabolic acidosis, etc.), iatrogenic conditions (e.g., radiation-induced tissue injury, surgery-related complications, etc.), and/or idiopathic processes (e.g., amyotrophic lateral sclerosis, Parsonnage-Turner Syndrome, etc.). Indeed, E-selectin expressed all over the endothelial cell, i.e., on both the luminal and abluminal sides of the endothelium.

Glycosylation Patterns of Cells

The overwhelming majority of proteins and lipids in mammalian cells are glycosylated, and distinct glycan determinants regulate critical aspects of cell biology. Assembly of glycans on N-linked glycoproteins and glycolipids is initiated in the ER, whereas O-glycosylation of proteins is initiated in the Golgi. In each case, glycan extension occurs by step-wise addition of monosaccharide units via the action of glycosyltransferases, type II integral membrane enzymes that stereo- and regiospecifically link the relevant monosaccharide to the pertinent substrate(s) (known as glycan "acceptors"). In humans, the terminal fucosylated lactosaminyl glycans known as Lewis-X ($Le^X$, also called "CD15": Gal-$\beta(1,4)$-[Fuc-$\alpha(1,3)$]-GlcNAc-R) and "sialyl Lewis-X" ($sLe^X$, also called "CD15s": NeuAc-$\alpha(2,3)$-Gal-$\beta(1,4)$-[Fuc-$\alpha(1,3)$]-GlcNAc-R) bear major biological significance. These trisaccharide ($Le^X$) and tetrasaccharide ($sLe^X$) structures are displayed on the cell surface on both glycoproteins and glycolipids, and, in each case, the final step in their assembly requires $\alpha(1,3)$-linked fucose modifications of N-acetylglucosamine (GlcNAc) within respective unsialylated or sialylated terminal Type 2 lactosamine (LacNAc) acceptors, i.e., Gal-$\beta(1,4)$-GlcNAc-R or NeuAc-$\alpha(2,3)$-Gal-$\beta(1,4)$-GlcNAc-R (FIG. 1). Importantly, $sLe^X$ can only be created by fucosylation of sialylated LacNAc, as there is no mammalian sialyltransferase that can place sialic acid in $\alpha(2,3)$-linkage to Gal in $Le^X$ to create $sLe^X$. Thus, the biosynthesis of $Le^X$ and $sLe^X$ in each case critically pivots on fucose addition. This reaction is programmed by glycosyltransferases known as $\alpha(1,3)$-fucosyltransferases ($\alpha(1,3)$-FTs), which, in humans, constitute a family of six Golgi isoenzymes: FT3, FT4, FT5, FT6, FT7, and FT9.

Display of $Le^X$ and $sLe^X$ are each very tightly regulated among mammalian cells (1), indicating that they each serve highly specialized biology. $Le^X$ is well-known to mediate a variety of important cellular functions in development and immunity. In mice, $Le^X$ is known as stage-specific embryonic antigen-1 (SSEA-1); it serves as a major marker of murine (but not human) embryonic stem cells (2, 3), and its expression is necessary for compaction of the morula (4). Importantly, in both mice and humans, $Le^X$ is a marker for neural stem cells (5-8), and $Le^X$-bearing glycoconjugates mediate neural stem cell proliferation by activating the Notch signaling pathway (9). $Le^X$ is immunomodulatory, serving as one of the main glycans recognized by DC-SIGN (CD209), a C-type lectin (i.e., requiring $Ca^{2+}$ for ligand binding) expressed by dendritic cells (10). Conspicuously, human (but not mouse) myeloid leukocytes express $Le^X$, and its expression in hematopoiesis is a hallmark of myeloid-specific lineage differentiation. Moreover, $Le^X$ is characteristically expressed on Reed-Sternberg cells in Hodgkin's lymphoma (11), and is displayed on certain human vascular and CNS malignancies (e.g., gliomas) in which it is considered an indicator of cancer stem cells (12, 13).

Though expression of $Le^X$ has garnered significant scientific interest, even more attention has been directed to $sLe^X$ as, has been described above, this glycan is the prototypical binding determinant for the family of C-type lectins ("selectins") that includes the endothelial molecule E-selectin (CD62E) (14). Binding of E-selectin to $sLe^X$-bearing glycoconjugates on circulating cells is critical to enable the deceleration of the flowing cells onto the endothelial surface, which is the key first step in cell migration. In all mammals, E-selectin is constitutively expressed in microvessels in the bone marrow and skin and is inducibly expressed in endothelial beds at inflammatory sites in response to the cytokines tumor necrosis factor (TNF) and interleukin-1 (IL-1) (15). Expression of cell surface $sLe^X$ is therefore a prerequisite for extravasation of all mammalian leukocytes and for migration of mammalian hematopoietic stem/progenitor cells (HSPCs) to marrow (15-17). Importantly, while $sLe^X$ plays a critical role in controlling leukocyte and HSPC migration, aberrant expression of this tetrasaccharide by human malignant cells is a critical mediator of cancer metastasis (18-20). Importantly, in addition to sLe$^X$, E-selectin can also bind to other α(1,3)-fucosylated sialyllactosamines known as "VIM-2" (or "CD65s") (21, 22) (in which fucose is α(1,3)-linked to GlcNAc within the penultimate LacNAc unit of a terminal polylactosaminyl glycan, i.e., NeuAc-α(2,3)-Gal-β(1,4)-GlcNAc-β(1,3)-Gal-β(1,4)-[Fu-α(1,3)]-GlcNAc-R) and difucosyl sLe$^X$ (in which fucose is α(1,3)-linked to GlcNAc within both the ultimate and penultimate LacNAc units, i.e., NeuAc-α(2,3)-Gal-β(1,4)-[Fuc-α(1,3)]-GlcNAc-β(1,3)-Gal-β(1,4)-[Fuc-α(1,3)]-GlcNAc-R) (See FIG. 1) (21).

In light of the conspicuously restricted cell expression patterns and the vital roles of Le$^x$ and sLe$^x$ in human cell biology, it is important to understand how the various α(1,3)-FTs shape the intracellular biosynthesis of these glycan determinants in humans. Extensive efforts in the 1980s and 1990s led to the identification and molecular cloning of all six human α(1,3)-FUTs that can catalyze creation of Le$^X$ and/or sLe$^X$ (FUT3 (23), FUT4 (24,25), FUT5 (26), FUT6 (27), FUT7 (28), and FUT9 (29)). These studies functionally characterized the enzymes as isolated proteins, analyzing their biosynthetic properties under non-physiologic ex vivo reaction conditions. Further studies employed a variety of molecular biology approaches in which cell surface fucosylated glycans were evaluated after transfecting various mammalian cell lines with individual α(1,3) FUT genes (30,31), in some cases in combination with biochemical approaches whereby α(1,3)FT activity was measured in the lysates of such cells using synthetic oligosaccharide (32-34) and glycolipid (35,36) acceptors. This body of work provided catalytic insights and yielded working classifications of the product specificities of the α(1,3)-FUT gene family, but caution must be drawn to the reliability of these specificities, especially on primary human cells, owing to the wide tapestry of methods and non-human, immortalized cell lines used to characterize the enzymatic targets (1, 37)).

Notably, there are substantial uncertainties in fucosyltransferase specificities resulting from variances in identified product profiles from all the prior studies employing both artificial substrates and cell lines (See Table 1A and 1B). For example, one only needs to consider the substrate and product specificities of Fucosyltransferase III and Fucosyltransferase IV to appreciate the overwhelming inconsistencies in the results of Le$^x$ and sLe$^x$ synthesis. Regarding Fucosyltransferase III on artificial substrates, there are five reports indicating synthesis of Lex (written in black; refs 23, 73, 75, 78, 26), two reports that it cannot make Lex (written in red; refs 76, 77) and one report that it can make a low amount of Lex (written in blue; ref 32) (Table 1A and 1B). For sLe$^x$, there are 5 reports stating that Fucosyltransferase III synthesizes sLe$^x$ (written in black; refs 73, 75, 76, 78, 26), two reports that it cannot synthesize sLe$^x$ (written in red; refs 76, 77), and one report that is can make a low amount of sLe$^x$ (written in blue; ref 32) (Table 1A and 1B). Regarding Fucosyltransferase IV on artificial substrates, there are four reports stating that it cannot synthesize sLe$^x$ (written in red; refs 76, 78, 26, 83) and five reports that it can make a low amount of sLe$^x$ (written in blue; refs 33, 79, 54, 32, 28) (Table I). By contrast, in analyses of cell lines, Fucosyltransferase III had no trouble making Lex or sLe$^x$ (Table 1A and 1B). Furthermore, Fucosyltransferase IV was found to synthesize Le$^x$, but it is inconsistent with respect to sLe$^x$ synthesis (i.e. three reports indicate that Fucosyltransferase IV can synthesize sLe$^x$ (written in black; refs 50, 49, 49), six reports state that it cannot synthesize sLe$^x$ (written in red; refs 78, 79, 27, 32, 86, 28), and three reports state that it can make low amounts of sLe$^x$ (written in blue; refs 54, 30, 31). Given the abundance of such disparate data, a person of ordinary skill in the art is unable to predict glycosylation product profiles of fucosyltransferases (FTs) on any type of cell. Furthermore, studies utilizing non-human cell lines and immortalized (i.e. carcinogenic) cell lines are not useful in human clinical applications wherein one would wish to employ a healthy (native) human cell bearing a distinct pattern of installed fucose(s).

Thus, there remain two overarching caveats regarding our current understanding of the human α(1,3)-FT isoenzymes that modify terminal lactosaminyl glycans: (i) Their ex vivo chemistry may not reflect their Golgi chemical biology; and (ii) their chemical biology within immortal cell lines, and, in particular, immortal non-human cell lines, can differ significantly from that within human cells.

Human mesenchymal stem cells (hMSCs) are known to natively display sialylated terminal Type 2 lactosaminyl glycans (thus possessing glycosyltransferases necessary to create this structure), but are natively deficient in Le$^x$ (CD15) and sLe$^x$ CD15s) expression, and also lack expression of VIM-2 (CD65s) and difucosyl sLe$^x$ (38,40). The present disclosure provides compositions and methods comprising all six human α(1,3)-FTs to generate sLe$^x$ and Le$^x$, as well as the related structures VIM-2 and difucosyl sLe$^x$, in cultures of human mesenchymal stem cells (hMSCs) and other types of human cells. According to some embodiments, the disclosure provides hMSCs modified by human α(1,3)-FT isoenzymes, that have clinical significance (e.g., the hMSCs may be used as precursors of bone-forming osteoblasts and/or used for their immunomodulation/anti-inflammatory properties and/or may be gene-modified to perform a pertinent biologic activity). According to some embodiments, hMSCs are transfected with modified-mRNA encoding the relevant human α(1,3)-FTs (i.e., FT3, FT4, FT5, FT6, FT7, and FT9) to generate a controlled pulse of the pertinent FT activity in these cells. In some embodiments, the distinct fucosylated lactosaminyl glycan products of these enzymes are then identified by flow cytometry analysis of the cell surface using well-validated monoclonal antibodies as probes. In some embodiments, the resulting cell surface glycan determinants are examined using mass spectrometry (MS) analysis, alone or together with flow cytometry analysis. In other embodiments, the cell surface of the hMSCs, or of other types of stem/progenitor cells, is modified by treatment with a relevant α(1,3)-FTs (i.e., FT3, FT4, FT5, FT6, FT7, and/or FT9) together with the donor nucleotide sugar (GDP-fucose) to install fucose stereospecifically onto a particular cell surface lactosaminyl glycan acceptor, thus generating one or a combination of cell surface glycans comprising Le$^X$, sLe$^X$, VIM-2 and difucosyl sLe$^X$, and the expression of the resulting glycan determinants are examined by flow cytometry and/or MS. In some embodiments, across several types/subsets of human leukocytes, the relevant cell surface glycans are modified by treatment with a pertinent α(1,3)-FTs (i.e., FT3, FT4, FT5, FT6, FT7, and/or FT9) together with the donor nucleotide sugar (GDP-fucose) to install fucose stereospecfically on a particular glycan acceptor and the expression of the resulting cell surface glycan determinants are examined using flow cytometry and/or MS. The present disclosure provides new insights on the biosynthetic properties of this important class of glycosyltransferases within the context of a human cell type, yielding novel compositions and methods for shaping expression of functionally significant α(1,3)-fucosylated glycan moieties on both glycoproteins and glycolipids in human cells. Based on such knowledge of the distinct product specificities of the various α(1,3)-FTs, the present disclosure also provides new insights on how to direct the placement upon a cell surface lactosaminyl glycan of a GDP-fucose donor wherein the fucose is modified with a chemically-reactive tag (e.g., a functional group serving as a chemical reporter) which would then allow subsequent conjugation with another structure (e.g., via a bioorthogonal chemical reaction) and/or wherein the fucose with GDP-fucose is linked (modified covalently) prior to introduction onto the cells with one or more additional molecules that confer a desired biologic property (-ies); in such cases, the use of the α(1,3)-FTs confers both regiospecificity and stereospecificity in the placement of the pertinent molecular moiety which is linked to the installed fucose. Furthermore, the capacity of a certain cell to display a given level of a glycan determinant following installation of a monosaccharide (e.g., α(1,3)-fucosylation) is a measure of the underlying (native) glycosignature that cell, and this glycosignature serves as a distinguishing marker of that specific cell type; thus, cells may be operationally stratified on the basis of the range/level of pertinent glycan determinants that are enforced by monosaccharide substitution (such as by contacting the cell with a relevant glycosyltransferase), thereby defining distinct subsets of cells within a complex mixture of cells.

SUMMARY OF THE INVENTION

The present disclosure provides a method of selectively enforcing a pattern of cell surface fucosylated lactosaminyl glycans on human cells, such as human primary cells. According to some embodiments, the pattern of cell surface fucosylated lactosaminyl glycans is enforced by introducing nucleic acid encoding a relevant glycosyltransferase or combinations of glycosyltransferases and/or exofucosylating the human cell with a relevant glycosyltransferase or combination of glycosyltransferases. According to some embodiments, the method of enforcement (e.g., nucleic acid transfection and/or exofucosylation) and selected glycosyltransferase(s) can result in a unique pattern of fucosylated lactosaminyl glycans enforced on the cell surface. In other embodiments, addition of a donor GDP-fucose wherein the fucose has been modified by methods known in the art with a chemical reactive group/molecular tag (e.g., biotinylated GDP-fucose, azido-GDP-fucose, etc.) thereby allowing for subsequent linkage of other molecules onto the installed fucose within cell surface lactosaminyl glycans (examples of this approach include, but are not limited to, utility of biotinylated GDP-fucose with subsequent complexing using streptavidin-conjugated molecules and/or use of "click chemistry" wherein the azido-containing fucose molecule is then complexed to an alkyne-containing molecule). In other embodiments, molecules covalently linked to the donor nucleotide fucose (i.e., GDP-fucose with covalent attachment of additional molecule(s)) can be stereospecifically added in a distinct pattern onto cell surface lactosaminyl glycans to endow a desired biologic property upon the cell. In other embodiments, the distinct patterns of expression of fucosylated lactosamines installed on the cell surface by contacting cells with one or more α(1,3)-fucosyltransferases can be used to characterize and isolate defined cell subsets within a heterogenous mixture of cells. In other embodiments, use of additional glycosyltransferases (in concert with their respective nucleotide sugar donor, e.g., an α(2,3)-sialyltransferase and CMP-sialic acid), can be utilized to enforce creation of the pertinent acceptor lactosaminyl glycan (e.g., α(2,3)-sialylated Type 2 lactosaminyl glycans) upon which, subsequently, the pertinent α(1,3)-fucosyltransferase will then add the fucose moiety (thereby, further increasing expression of sLeX, VIM-2, and/or difucosyl sLe$^x$). In other embodiments, a glycosidase can be used (e.g., a sialidase to cleave terminal α(2,3)-sialic acid or terminal α(2,6)-sialic acid, thereby creating "neutral" type 2 lactosamine termini; a hexosaminidase to cleave N-acetylgalactosamine from the Sda antigen (GalNAc-β(1,4)-[Neu5Ac-α(2,3)]-Gal-β(1,4)-GlcNAc-R) to create α(2,3)-sialylated Type 2 lactosaminyl glycans), upon which, subsequently, a pertinent fucosyltransferase can add the fucose moiety (e.g., by use of sialidases, to selectively enforce desired higher levels of Le$^x$ on the cell surface by use of FT9; by use of hexosaminidases, to selectively enforce desired higher levels of sLeX on the exposed α(2,3)-sialylated Type 2 lactosaminyl glycans).

According to some embodiments, the composition of the installed terminal lactosaminyl glycan determinants, i.e., the enforced fucosylated lactosaminyl glycan glycosylation pattern on cells, is selected from the group consisting of:

(i) Le$^x$ expression (i.e., Le$^x$(+)) substantially greater (i.e., ">>") than sLe$^x$ expression (sLe$^x$ (+)), without VIM-2 expression (i.e., VIM-2 (−)), and without Di-Fuc-sLe$^x$ expression (i.e., Di-Fuc-sLe$^x$ (−)) (altogether, abbreviated as Le$^x$(+)>>sLe$^x$ (+), with VIM-2 (−) and Di-Fuc-sLe$^x$ (−));

(ii) sLe$^x$ (+)>>Le$^x$(+), with Di-Fuc-sLe$^x$ (+), and VIM-2 (−);

(iii) sLe$^x$ (+) and Di-Fuc-sLe$^x$ (+), with Le$^x$(−), and VIM-2 (−);

(iv) Le$^x$(+), with sLe$^x$ (−), VIM-2 (−), and Di-Fuc-sLe$^x$ (−); and (v) sLe$^x$ (+), VIM-2 (+), and Di-Fuc-sLe$^x$ (+)>Le$^x$(+).

According to some embodiments, the glycosyltransferase is an α(1,3)-fucosyltransferase. According to some embodiments, the fucosyltransferase is selected from the group consisting of Fucosyltransferase III, Fucosyltransferase IV, Fucosyltransferase V, Fucosyltransferase VI, Fucosyltransferase VII, Fucosyltransferase IX. According to some embodiments, contacting the cell with Fucosyltransferase IV results in the enforced glycosylation pattern of (i). According to some embodiments, contacting the cell with Fucosyltransferase VI results in the enforced glycosylation pattern of (ii). According to some embodiments, contacting the cell with Fucosyltransferase VII results in the enforced glycosylation pattern of (iii). According to some embodiments, contacting the cell with Fucosyltransferase IX results in the enforced glycosylation pattern of (iv). According to some embodiments, contacting the cell with Fucosyltransferase III and/or Fucosyltransferase V results in the enforced glycosylation pattern of (v). According to some embodiments, the cell is a stem cell. According to some embodiments, the cell is a progenitor cell. According to some embodiments, the stem/progenitor cell is a human mesenchymal stem cell (hMSC). According to some embodiments, the cell is a leukocyte. According to some embodiments, the enforced glycosylation pattern is effective to increase the cell binding to E- and/or L-selectin. According to some embodiments, the enforced glycosylation pattern is effective to increase reactivity of the cell to antibodies that recognize sLe$^x$ (e.g., HECA-452 antibody) or to antibodies directed to Le$^x$. According to some embodiments, one or more of the Le$^x$, sLe$^x$, VIM-2, and Di-Fuc-sLe$^x$ comprises functionalized fucose capable of being covalently linked to another molecule by a subsequent chemical reaction (e.g., via "click" chemistry). According to some embodiments, contacting the functionalized fucose with a molecule forms a covalent link between the functionalized fucose and the molecule. According to some embodiments, the molecule comprises biotin. According to some embodiments, a streptavidin-labeled molecule is then contacted with the biotin, e.g., a streptavidin-labelled antibody is contacted with the biotin to conjugate the antibody to the fucose(s) of the $Le^x$, $sLe^x$, VIM-2, and/or Di-Fuc-$sLe^x$. In some embodiments, the cells are further contacted with a sialidase, hexosaminidase, or combinations thereof, before or concurrently with the combination of glycosyltransferases comprising a sialyltransferase.

The present disclosure also provides a cell comprising an enforced glycosylation pattern made by the process of contacting the cell with a glycosyltransferase, wherein the enforced glycosylation pattern is selected from the group consisting of: (i) $Le^x(+)\gg sLe^x$ (+), with VIM-2 (−) and Di-Fuc-$sLe^x$ (−); (ii) $sLe^x$ (+)$\gg Le^x(+)$, with Di-Fuc-$sLe^x$ (+), and VIM-2 (−); (iii) $sLe^x$ (+) and Di-Fuc-$sLe^x$ (+), with $Le^x(-)$, and VIM-2 (−); (iv) $Le^x(+)$, with $sLe^x$ (−), VIM-2 (−), and Di-Fuc-$sLe^x$ (−); (v) $sLe^x$ (+), VIM-2 (+), and Di-Fuc-$sLe^x$ (+)$>Le^x(+)$. According to some embodiments, the glycosyltransferase is an $\alpha(1,3)$-fucosyltransferase. According to some embodiments, the fucosyltransferase is selected from the group consisting of Fucosyltransferase III, Fucosyltransferase IV, Fucosyltransferase V, Fucosyltransferase VI, Fucosyltransferase VII, Fucosyltransferase IX. According to some embodiments, contacting the cell with Fucosyltransferase IV results in the enforced glycosylation pattern of (i). According to some embodiments, contacting the cell with Fucosyltransferase VI results in the enforced glycosylation pattern of (ii). According to some embodiments, contacting the cell with Fucosyltransferase VII results in the enforced glycosylation pattern of (iii). According to some embodiments, contacting the cell with Fucosyltransferase IX results in the enforced glycosylation pattern of (iv). According to some embodiments, contacting the cell with Fucosyltransferase III and/or Fucosyltransferase V results in the enforced glycosylation pattern of (v). According to some embodiments, the cell is a tissue progenitor cell or a stem cell. According to some embodiments, the stem/progenitor cell is a human mesenchymal stem cell (hMSC). According to some embodiments, the enforced glycosylation pattern is effective to increase the cell binding to E- and/or L-selectin. According to some embodiments, the enforced glycosylation pattern is effective to increase reactivity of the cell to one or more of HECA-452 antibody, CSLEX1 antibody (reactive with $sLe^x$), HI98 antibody (reactive with $Le^x$), VIM-2 antibody, and FH6 antibody (reactive with difucosyl $sLe^x$). According to some embodiments, one or more of the $Le^x$, $sLe^x$, VIM-2, and Di-Fuc-$sLe^x$ comprises functionalized fucose covalently linked to a molecule. In some embodiments, the molecule comprises biotin. According to some embodiments, the biotin is then conjugated to an avidin/streptavidin bound molecule, e.g., an avidin/strepavidin-labelled antibody which can then be complexed to the fucose(s) of the $Le^x$, $sLe^x$, VIM-2, and/or Di-Fuc-$sLe^x$. In some embodiments, the cells are contacted with a sialidase, hexosaminidase, or combinations thereof, before or concurrently with the combination of glycosyltransferases comprising a sialyltransferase.

The present disclosure also provides a method of selectively tuning the cell surface glycans of a human cell (such as mesenchymal stem cell (hMSC)) to express the following glycosylation pattern, $Le^x(+)$, $sLe^x$ (+), VIM-2 (−), and Di-Fuc-$sLe^x$ (−), comprising selecting a Fucosyltransferase IV and contacting the human cell with the selected enzyme.

The present disclosure also provides a method of selectively tuning the cell surface glycans of a human cell (such as mesenchymal stem cell (hMSC)) to express the following glycosylation pattern, $Le^x(+)$, $sLe^x$ (+), VIM-2 (−), and Di-Fuc-$sLe^x$ (+), comprising selecting a Fucosyltransferase VI and contacting the cell (e.g., hMSC) with the selected enzyme.

The present disclosure also provides a method of selectively tuning the cell surface glycans of a human cell such as a mesenchymal stem cell (hMSC) to express the following glycosylation pattern, sLex(+), Lex(−), VIM-2 (−), and Di-Fuc-$sLe^x$ (+), comprising selecting a Fucosyltransferase VII and contacting the human cell with the selected enzyme.

The present disclosure also provides a method of selectively tuning the cell surface glycans of a human cell such as a mesenchymal stem cell (hMSC) to express the following glycosylation pattern, $Le^x(+)$, $sLe^x$ (−), VIM-2 (−), and Di-Fuc-$sLe^x$ (−), comprising selecting a Fucosyltransferase IX and contacting the human cell with the selected enzyme.

The present disclosure also provides a method of selectively tuning the cell surface glycans of a human cell such as a human mesenchymal stem cell (hMSC) to express the following glycosylation pattern, $Le^x(+)$, $sLe^x$ (+), VIM-2 (+), and Di-Fuc-$sLe^x$ (+), comprising selecting Fucosyltransferase III and/or Fucosyltransferase V and contacting the human cell with the selected enzyme(s). Desired expression patterns of fucosylated lactosaminyl glycans could be achieved by using a combination of $\alpha(1,3)$-fucosyltransferases (e.g., Fucosyltransferase VI in combination with Fucosyltransferase IX, to enforce high expression of both $Le^x$ and $sLe^x$ (i.e., $Le^x(+)$ and $sLe^x$ (+)), with Di-Fuc-$sLe^x$ (+) and VIM-2 (−)).

The present disclosure also provides a method of treating tissue injury of a subject comprising the steps of administering to the subject a cell according to any one or more of the disclosed embodiments. The present disclosure also provides a method of delivering a cell to any site of inflammation in a subject comprising the step of administering the cell of any one or more of the disclosed embodiments to the subject. The present disclosure also provides a method of delivering a cell to any site of cancer in a subject comprising the step of administering the cell of any one or more of the disclosed embodiments to the subject. The present disclosure also provides a method of delivering a cell to the bone marrow of a subject comprising the step of administering the cell of any one or more of the disclosed embodiments to the subject. The present disclosure also provides a method of delivering a cell to the skin of a subject comprising the step of administering the cell of any one or more disclosed embodiments to the subject.

The present disclosure also provides, a composition comprising a cell having an enforced glycosylation pattern selected from the group consisting of:
(i) $Le^x(+)\gg sLe^x$ (+), with VIM-2 (−) and Di-Fuc-$sLe^x$ (−);
(ii) $sLe^x$ (+)$\gg Le^x(+)$, with Di-Fuc-$sLe^x$ (+), and VIM-2 (−);
(iii) $sLe^x$ (+) and Di-Fuc-$sLe^x$ (+), with $Le^x(-)$, and VIM-2 (−);
(iv) $Le^x(+)$, with $sLe^x$ (−), VIM-2 (−), and Di-Fuc-$sLe^x$ (−); and
(v) $sLe^x$ (+), VIM-2 (+), and Di-Fuc-$sLe^x$ (+)$>Le^x(+)$.

According to some embodiments, the cell is a human cell. According to some embodiments, the cell is a human primary cell. According to some embodiments, the human cell is a human mesenchymal stem cell (hMSC). According to some embodiments, the cell binds to one or more of HECA-452 antibody, CSLEX1 antibody, H198 antibody, VIM-2 antibody, and FH6 antibody. According to some embodiments, the cell binds to E- and/or L-selectin. In some embodiments, one or more of the $Le^x$, $sLe^x$, VIM-2, and Di-Fuc-$sLe^x$ comprises functionalized fucose covalently linked to a molecule. In some embodiments, the molecule comprises biotin. In some embodiments, the biotin is conjugated to an avidin/streptavidin bound antibody on the fucoses of the $Le^x$, $sLe^x$, VIM-2, and Di-Fuc-$sLe^x$.

The present disclosure also provides, a process for custom engineering a fucosylated lactosaminyl glycan comprising: (a) determining a desired glycosylation pattern for a target human cell, wherein the glycosylation pattern is selected from the group consisting of:

(i) $Le^x$(+)>>$sLe^x$ (+), with VIM-2 (−) and Di-Fuc-$sLe^x$ (−);
(ii) $sLe^x$ (+)>>$Le^x$(+), with Di-Fuc-$sLe^x$ (+), and VIM-2 (−);
(iii) $sLe^x$ (+) and Di-Fuc-$sLe^x$ (+), with $Le^x$(−), and VIM-2 (−);
(iv) $Le^x$(+), with $sLe^x$ (−), VIM-2 (−), and Di-Fuc-$sLe^x$ (−); and
(v) $sLe^x$ (+), VIM-2 (+), and Di-Fuc-$sLe^x$ (+)>$Le^x$(+);

(b) selecting an α(1,3)-fucosyltransferase capable of producing the desired glycosylation pattern; and (c) contacting the target human cell with the selected fucosyltransferase. According to some embodiments, the fucosyltransferase is selected from the group consisting of Fucosyltransferase III, Fucosyltransferase IV, Fucosyltransferase V, Fucosyltransferase VI, Fucosyltransferase VII, and Fucosyltransferase IX. According to some embodiments, contacting the cell with Fucosyltransferase IV results in the enforced glycosylation pattern of (i). According to some embodiments, contacting the human cell with Fucosyltransferase VI results in the enforced glycosylation pattern of (ii). According to some embodiments, contacting the human cell with Fucosyltransferase VII results in the enforced glycosylation pattern of (iii). According to some embodiments, contacting the cell with Fucosyltransferase IX results in the enforced glycosylation pattern of (iv). According to some embodiments, contacting the cell with Fucosyltransferase III and or Fucosyltransferase V results in the enforced glycosylation pattern of (v). According to some embodiments, the contacting of step (c) occurs in the presence of functionalized fucose capable of being covalently linked to another molecule, wherein the functionalized fucose is incorporated into one or more of the $Le^x$, $sLe^x$, VIM-2, and Di-Fuc-$sLe^x$. In some embodiments, the process further comprises the step of contacting the $Le^x$, $sLe^x$, VIM-2, and Di-Fuc-$sLe^x$ comprising functionalized fucose with a molecule to form a covalent link between the functionalized fucose and the molecule. In some embodiments, the molecule comprises biotin. In some embodiments, the process further comprises the step of contacting a streptavidin-labeled molecule (e.g., an antibody) with the biotin (e.g., conjugating the antibody to the fucoses of the $Le^x$, $sLe^x$, VIM-2, and/or Di-Fuc-$sLe^x$). In some embodiments, the cells are contacted with a sialidase, hexosaminidase, sialyltransferase or other glycosyltransferases, or combinations thereof, before or concurrently with the fucosyltranferase.

The present disclosure also provides, a process for custom engineering a fucosylated lactosaminyl glycan comprising: (a) determining a desired glycosylation pattern for a target human cell, wherein the glycosylation pattern is selected from the group consisting of:

(i) $Le^x$(+)>>$sLe^x$ (+), with VIM-2 (−) and Di-Fuc-$sLe^x$ (−);
(ii) $sLe^x$ (+)>>$Le^x$(+), with Di-Fuc-$sLe^x$ (+), and VIM-2 (−);
(iii) $sLe^x$ (+) and Di-Fuc-$sLe^x$ (+), with $Le^x$(−), and VIM-2 (−);
(iv) $Le^x$(+), with $sLe^x$ (−), VIM-2 (−), and Di-Fuc-$sLe^x$ (−); and
(v) $sLe^x$ (+), VIM-2 (+), and Di-Fuc-$sLe^x$ (+)>$Le^x$(+);

(b) selecting an α(1,3)-fucosyltransferase capable of producing the desired glycosylation pattern; and (c) contacting the target human cell with the selected fucosyltransferase. According to some embodiments, the fucosyltransferase is selected from the group consisting of Fucosyltransferase III, Fucosyltransferase IV, Fucosyltransferase V, Fucosyltransferase VI, Fucosyltransferase VII, and Fucosyltransferase IX. According to some embodiments, contacting the cell with Fucosyltransferase IV results in the enforced glycosylation pattern of (i). According to some embodiments, contacting the human cell with Fucosyltransferase VI results in the enforced glycosylation pattern of (ii). According to some embodiments, contacting the human cell with Fucosyltransferase VII results in the enforced glycosylation pattern of (iii). According to some embodiments, contacting the cell with Fucosyltransferase IX results in the enforced glycosylation pattern of (iv). According to some embodiments, contacting the cell with Fucosyltransferase III and or Fucosyltransferase V results in the enforced glycosylation pattern of (v). The creation of these fucosylated lactosamine profiles can then be used to define distinct cells that have been contacted with the pertinent Fucosyltransferase(s). For example, by selecting cells by fluorescence-activated cell sorting (FACS) that contain either the highest or lowest expression levels (i.e., MFI) for a given determinant that is labeled by a fluorescence tag, one can enrich for subpopulations of cells with inherently different glycosignatures; such glycosignatures could thus be useful in defining unique subsets of cells with distinct operational capabilities. In some embodiments, the cells are contacted with a sialidase, hexosaminidase, sialyltransferase or other glycosyltransferases, or combinations thereof, before or concurrently with the fucosyltranferase.

The present disclosure also provides a method of selecting and/or identifying human cells comprising the steps of (a) providing a population of human cells; (b) contacting the population of human cells with one or more α(1,3)-fucosyltransferase(s); (c) detecting the fucosylated lactosaminyl glycans $Le^x$, $sLe^x$, VIM-2, and Di-Fuc-$sLe^x$ on the population of human cells; and (d) identifying the population of human cells having a fucosylated lactosaminyl glycan pattern selected from the group consisting of: (i) $Le^x$(+)>>$sLe^x$ (+), VIM-2 (−), and Di-Fuc-$sLe^x$ (−); (ii) $sLe^x$ (+)>>$Le^x$(+), with Di-Fuc-$sLe^x$ (+), and VIM-2 (−); (iii) $sLe^x$(+), $Le^x$(−), VIM-2 (−), and Di-Fuc-$sLe^x$ (+); (iv) $Le^x$(+), $sLe^x$ (−), VIM-2 (−), and Di-Fuc-$sLe^x$ (−); and (v) $sLe^x$ (+)>$Le^x$(+), VIM-2 (+), and Di-Fuc-$sLe^x$ (+). In some embodiments, the α(1,3)-fucosyltransferase is selected from the group consisting of Fucosyltransferase III, Fucosyltransferase IV, Fucosyltransferase V, Fucosyltransferase VI, Fucosyltransferase VII, Fucosyltransferase IX. In some embodiments, contacting the cell with Fucosyltransferase IV results in the enforced glycosylation pattern of (i). In some embodiments, contacting the cell with Fucosyltransferase VI results in the enforced glycosylation pattern of (ii). In some embodiments, contacting the cell with Fucosyltransferase VII results in the enforced glycosylation pattern of (iii). In some embodiments, contacting the cell with Fucosyltransferase IX results in the enforced glycosylation pattern of (iv). In some embodiments, contacting the cell with Fucosyltransferase III and/or Fucosyltransferase V results in the enforced glycosylation pattern of (v). In some embodiments, the method further comprises (e) selecting a sub-population of cells from the population of human cells having the fucosylated lactosaminyl glycan pattern of (i), (ii), (iii), (iv), or (v) after fucosylation with FTIV, FTVI, FTVII, FTIX, or FTIII/FTV, respectively. In some embodiments, the sub-population of human cells is selected for expression of one or more of markers $Le^x$, $sLe^x$, VIM-2, or Di-Fucosyl-$sLe^x$ in the upper 50th percentile or greater of expression level of the population. In some embodiments, the sub-population of human cells is selected for expression of one or more of markers $Le^x$, $sLe^x$, VIM-2, or Di-Fucosyl-$sLe^x$ in the upper 20th percentile or greater of expression level of the population. In some embodiments, the sub-population of human cells is selected for expression of one or more of markers $Le^x$, $sLe^x$, VIM-2, or Di-Fucosyl-$sLe^x$ in the upper 10th percentile or greater of expression level of the population. In some embodiments, the sub-population of human cells is selected for expression of one or more of $Le^x$, $sLe^x$, VIM-2, or Di-Fucosyl-$sLe^x$ in the upper 5th percentile or greater of expression level of the population. In some embodiments, the sub-population of human cells is selected for expression of one or more of $Le^x$, $sLe^x$, VIM-2, or Di-Fucosyl-$sLe^x$ in the lower 50th percentile or lower of expression level of the population. In some embodiments, the sub-population of human cells is selected for expression of one or more of $Le^x$, $sLe^x$, VIM-2, or Di-Fucosyl-$sLe^x$ in the lower 30th percentile or lower of expression level of the population. In some embodiments, the sub-population of human cells is selected for expression of one or more of $Le^x$, $sLe^x$, VIM-2, or Di-Fucosyl-$sLe^x$ in the lower 10th percentile or lower of expression level of the population.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

BRIEF DESCRIPTION OF THE DRAWINGS

FIG. 1A shows Stereospecific addition of fucose in $\alpha(1,3)$-linkage to N-acetylglucosamine (GlcNAc) of a terminal Type 2 lactosamine creates Lewis X ($Le^x$). FIG. 1B shows stereospecific addition of fucose in $\alpha(1,3)$-linkage to the terminal GlcNAc of a sialylated type 2 polylactosamine terminal creates $sLe^x$, while addition of fucose to the penultimate GlcNAc yields VIM-2, and, fucosylation of both the terminal and penultimate GlcNAc generates Difucosyl $sLe^x$.

FIG. 1A shows quantitative RT-PCR performed to measure human MSC gene expression levels of glycosyltransferases required for lactosamine synthesis (Beta4GalT1, n=3), initiation of complex N-glycans (MGAT1, n=7), and construction of core 2 O-glycans (C2GnT-1, n=3), as well as the three human $\alpha(2,3)$ sialyltransferases that can terminally sialylate a Type 2 lactosamine (n=4). FIG. 2B shows quantitative RT-PCR performed to measure hMSC gene expression levels of the six human $\alpha(1,3)$ fucosyltransferases (FUT 3, 4, 5, 6, 7, 9) and the core $\alpha(1,6)$ fucosyltransferase FUT8 (for each, minimum of n=4). FIG. 2C shows MALII lectin binding (which detects sialylated lactosamines) to untreated or sialidase-treated hMSCs was evaluated by flow cytometry (n=5; Paired T-test, *p<0.001; Error bars represent SD). FIG. 2D shows cell surface levels of unsialylated lactosamines on untreated and sialidase treated hMSCs, as measured by flow cytometry for ECA lectin (which detects unsialylated lactosamines) (n=5; Paired T-test, p=0.01; Error bars represent SD). FIG. 2E shows cell surface levels of $Le^X$ (measured by antibody H198; light grey bars) and $sLe^X$ (measured by antibody CSLEX1; dark grey bars), on native (untreated) hMSCs or after exofucosylation ("exo MSC") with purified FT6 enzyme. Unstained hMSCs are also shown to indicate background of detection (n=4; Paired T-test, **p<0.01 between untreated and FT6 exo MSC; Individual data points are depicted, with error bars representing SD.

FIG. 3A shows ECA-lectin binding (left panel), SNA lectin binding (which detects $\alpha(2,6)$-sialylated lactosamines; middle panel) and MALII lectin binding (right panel) were measured on hMSCs, either untreated (clear dotted histograms), or treated with sialidase from *Macrobdella decora* (specific for $\alpha(2,3)$-sialic acid linkages; light grey histograms), or treated with sialidase from *Arthobacter ureacaciens* (which cleaves all types of sialic acid linkages; dark grey histograms). FIG. 3B shows $sLe^X$ expression (left panel), and $Le^X$ expression (right panel) measured on hMSCs, either untreated (clear histogram) or hMSCs exofucosylated with FT6 (FT6-exo; grey histogram).

FIG. 4A shows a schematic diagram of long and short FUT4 isoforms including 5' and 3' untranslated regions (UTR), start codons (ATG) and stop codons.

FIG. 4B shows a schematic diagram of modRNA constructs including the coding sequence from the long and short FUT4 isoforms. FIG. 4C shows Lewis X (CD15) levels measured by flow cytometry on hMSCs transfected 2 days prior with $FUT4_{long}$ modRNA or $FUT4_{short}$ modRNA. Statistics performed: 1-way ANOVA (p<0.0001) plus Dunnett post-test to compare all stained samples with unstained control. ** p<0.01. Individual data points are depicted, with error bars representing SD.

FIG. 5A shows quantitative RT-PCR performed to measure the transcript level of $FUT4_{LONG}$ isoform in hMSCs (light grey bars; n=3 independent hMSC lines) compared with HL60 cells used as positive control (dark grey bars; n=2 independent measurements for $FUT4_{LONG}$, and three independent measurements for $FUT4_{COMMON}$). Individual data points are depicted, with error bars representing SD. FIG. 5B shows representative gel images display amplicon size detected by both FUT4$_{LONG}$ and FUT4$_{COMMON}$ primers in hMSCs (left panel) and in positive control samples (right panel). Numbers on the left of each image present size of DNA fragment in base pairs (bp).

FIG. 6A shows sLe$^X$ (measured by antibody CSLEX1) levels and FIG. 6B shows Le$^X$ (measured by antibody HI98) levels measured on the cell surface. Non-transfected (NT) hMSCs and matched FUT3, 5, 6, 7, and 9 transfected hMSCs were compared relative to each other (n=15), while FUT4 transfected hMSCs were compared separately along with a partially overlapping set of matched NT controls (n=9). Statistics performed were repeated measures ANOVA ($p<0.0001$ for both FIG. 6A and FIG. 6B) followed by a Tukey post-test, comparing all columns with each other. Symbol above each bar compares to NT. For sLe$^X$, FUT9 is significantly lower than FUT3, 5, 6, and 7 ($p<0.001$), and for Le$^X$, FUT7 is significantly lower than FUT3, FUT5, FUT6, and FUT9 ($p<0.001$).

FIG. 7A to FIG. 7D depict representative flow cytometry histograms of hMSC FUT-transfectants stained with glycan-specific antibodies (mentioned in parentheses). FIG. 7A shows sLe$^X$ (CD15s) expression measured by mAb CSLEX1 binding. FIG. 7B shows Le$^X$ (CD15) expression measured by mAb HI98 binding. FIG. 7C shows VIM-2 (CD65s) expression measured by mAb VIM-2 binding. FIG. 7D shows difucosyl sLe$^x$ expression was measured by mAb FH6 binding.

FIG. 8A to FIG. 8C depicts a summary and comparison of fucosylated glycan products generated by the human α(1,3)-FTs using flow cytometry of cell surface and mass spectrometry analysis of fractionated cellular glycans. FIG. 8A shows a summary table of all flow cytometry data. (−): Insignificant amounts created on the cell surface. (+): Low, (++) moderate, and (+++) high levels created on the cell surface. NT=non-transfected. FIG. 8B shows a summary table of all mass spectrometry data. Glycans were fractionated into N-glycans, O-glycans, and glycospingolipids (GSLs) and analyzed separately for Le$^X$, sLe$^X$, and difucosyl sLe$^X$. NT=non-transfected. N-glycan and GSL analysis was not quantitative and results are presented as present, trace, or undetected (U). O-glycan analysis was semi-quantitative (FIG. 10), and was classified as (−) insignificant, (+) Low, (++) moderate, and (+++) high. FIG. 8C shows a comparison of Le$^X$ and sLe$^X$ creation on O-glycans (measured by LC-MS, n=3 to 6) and on the cell surface (measured by FACS, n=9 to 15) after transfection with FUT modRNA. NT=non-transfected control. Error bars represent SD.

FIG. 9A to FIG. 9D shows the disassembly of the m/z 1322$^{2+}$ precursor. FIG. 9A shows the MS$^2$ spectrum, which contains fragments of the multiple isomers sharing this composition. FIG. 9B shows the MS$^3$ fragmentation spectrum of the m/z 660 fragment, which is consistent with a Le$^X$ structure. FIG. 9C and FIG. 9D show the MS$^3$ and MS$^4$ spectra of the m/z 1021 and m/z 646 fragments, respectively. These spectra are indicative of a sialylated Le$^X$-containing isomer. FIG. 9E shows the MS$^2$ spectrum of the difucosylated, monosialylated, triLacNAc composition. This spectrum is clearly made up of multiple isomers of biantennary and triantennary structures. FIG. 9F shows the MS$^3$ spectrum of the putative sLe$^x$-Le$^x$ heptasaccharide fragment. The NeuAc loss fragment, in the presence of sLe$^x$ tetrasaccharide and internal Le$^x$ trisaccharide fragments, are strongly indicative of the sLe$^x$-Le$^x$ motif.

FIG. 11A shows the MS$^2$ spectrum of a putative fucosylated tetraosylceramide. Due to fatty acid heterogeneity, this is likely a mixture of sample components, but fragments of the fucosylated neolactotetraosylceramide are certainly present. FIG. 11B shows the MS$^3$ spectrum of the m/z 660 fragment, which has the same mass and fragmentation spectrum as the Le$^X$ structure from N-glycans. The protonated ceramide moiety has the same precursor mass and contributes some peaks in this spectrum. FIG. 11C shows the MS$^2$ spectrum of the m/z 1066 precursor, which would include the putative sialofucosylated tetraosylceramide, among other sample components. Due to this sample complexity, an MS$^3$ spectrum (FIG. 11D) is required to detect the sLe$^x$ structure, with the prominent NeuAc loss at m/z 646. For this sample, there was sufficient ion intensity to obtain an MS$^4$ spectrum (FIG. 11E), further confirming the sLe$^x$ structure.

FIG. 12A to FIG. 12B show disassembly of the m/z 1518 precursor. FIG. 12B shows the CID spectrum of the fucosylated-LacNAc consistent with a Le$^x$ motif. FIG. 12C to FIG. 12E show the disassembly of the m/z 1880 precursor. FIG. 12D and FIG. 12E show the sLe$^x$ fragmentation spectra.

FIG. 13 shows a list of qRT-PCR primers

FIG. 14A to 14E shows representative flow cytometry histograms of exofucosylated lymphocytes stained for Le$^x$ (CD15), sLe$^x$ (CD15s and HECA-452-FITC), VIM-2 (VIM-2-FITC), and difucosyl sLe$^x$ (FH6-APC). The histograms represent (from top to bottom) mouse IgM FITC control cells, untreated control cells, FT7 exofucosylated cells, and FT9 exofucoslyated cells.

FIG. 15A to 15E shows representative flow cytometry histograms of exofucosylated monocytes stained for Le$^x$ (CD15-FITC), sLe$^x$ (CD15s-FITC and HECA-452-FITC), VIM-2 (VIM-2-FITC), and difucosyl sLe$^x$ (FH6-APC). The histograms represent (from top to bottom) IgM-FITC (isotype control-labeled) cells, untreated control cells, FT7 exofucosylated cells, and FT9 exofucosylated cells.

DETAILED DESCRIPTION

Figure 1A:
FIG. 1A and FIG. 1B shows the biosynthesis of terminally fucosylated lactosaminyl glycans from sialylated or unsialylated type 2 lactosamine acceptors.
Figure 1B:
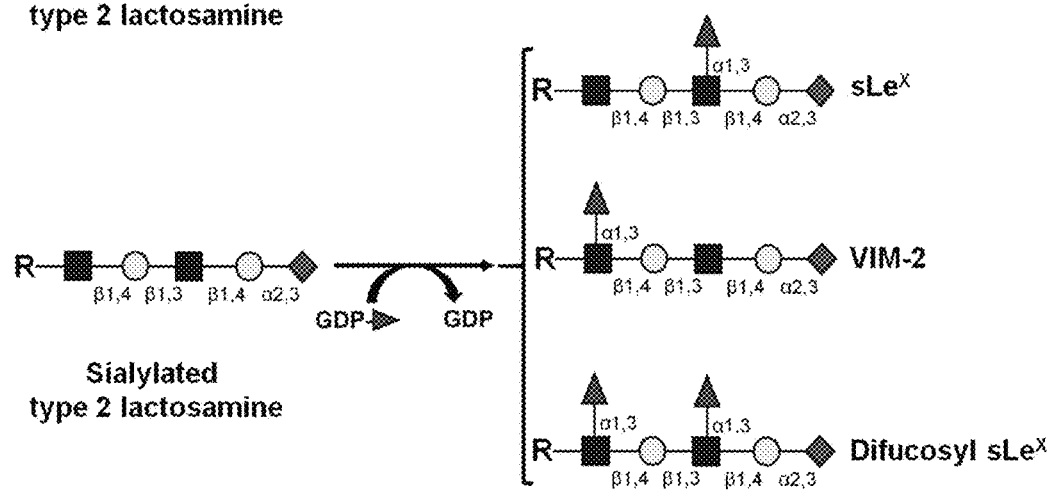

The present disclosure is directed to methods and compositions for enforcing a pattern of cell surface glycosylation. According to some embodiments, the pattern of enforced cell surface glycosylation comprises selectively enforced fucosylated lactosaminyl glycans on a human cell. The human cell may be a primary cell. The human cell may be derived from any somatic tissue source (a mature cell), or any progenitor cell or stem cell derived from ectodermal, mesodermal or endodermal-lineage tissues/cells, including cells derived from epithelial tissue, muscle tissue, connective tissue, or nervous tissue. According to some embodiments, the cell is derived from organs of the musculoskeletal system, digestive system, respiratory system, urinary system, reproductive organs, endocrine system, cardiovascular system, lymphatic system, nervous system, sensory organs, integumentary system, among others.

According to some embodiments, the cell is a human mesenchymal stem cell. The term "mesenchymal stem cell" (MSC) refers to cells isolated from stroma, the connective tissue that surrounds other tissues and organs. MSCs express a panel of markers including, but not limited to, CD13, CD44, CD73, CD105. MSC derived from Bone Marrow (BMMSCs) are postnatal stem cells capable of self-renewing and differentiating into osteoblasts, chondrocytes, adipocytes, and neural cells. These cells typically express STRO-1, CD29, CD73, CD90, CD105, CD146, and SSEA4, but do not express hematopoietic cell markers, especially CD14 and CD34; however, MSCs derived from tissues other than marrow (e.g., from adipose tissue) and a subset of MSCs known as "pericytes" natively express CD34, and this marker is characteristically lost on culture-expansion. In some embodiments, the MSCs are cultured at low densities (i.e. less than 70% maximum confluency). The MSC could be unmodified or may be modified (e.g., by nucleic acid transfection to express a desired protein product of interest).

According to some embodiments, the cell is a leukocyte, such as a peripheral blood mononuclear cell (PBMC). PBMCs include lymphocytes (e.g., T-cells, B-cells, NK-cells), and monocytes. Other types of leukocytes include granulocytes (e.g. neutrophils, basophils, eosinophils) and dendritic cells. The leukocyte may be culture-expanded (e.g., culture expanded regulatory T cells (Tregs) or NK cells or other effector lymphocyte subsets; culture-expanded dendritic cells; etc.)) and/or gene-modified to express desired proteins (e.g., chimeric antigen receptor-T cells (CAR-T cells)).

According to some embodiments, the cell is a human "polymorphonuclear cell" (PMN). PMNs include immune cells having granules (e.g. granulocytes) that are released during infections, allergic reactions, and asthma. PMNs include, but are not limited to, neutrophils, basophils, eosinophils, and mast cells. In some embodiments, the neutrophils are characterized as comprising the markers $CD15^+$, $CD16^+$, and $CD49d^-$. In some embodiments, the basophils are characterized as comprising 2D7 antigen, $CD117^-$, $CD123^+$, $CD203c^+$, and $Fc\epsilon RI\alpha^+$. In some embodiments, the eosinophils are characterized as comprising $CD11b^+$, $CD193^+$, $EMR1^+$, and $Siglec-8^+$.

Custom-Modifying Expression of Glycan Determinants

According to some embodiments, distinct patterns of glycans, such as fucosylated lactosaminyl glycans, may be enforced on a population of cells. In some embodiments, the pattern of cell surface fucosylated lactosaminyl glycans on a cell comprises the presence or absence of one or more of $sLe^x$, $Le^x$, VIM-2, and Di-Fuc-$sLe^x$. The glycosylation pattern may be represented using notation such as:
$Le^x$ (+), $sLe^x$ (+), VIM-2 (+), and Di-Fuc-$sLe^x$ (+);
$Le^x$ (+), $sLe^x$ (+), VIM-2 (−), and Di-Fuc-$sLe^x$ (−);
$Le^x$ (+), $sLe^x$ (+), VIM-2 (−), and Di-Fuc-$sLe^x$ (+);
$Le^x$ (−), $sLe^x$ (+), VIM-2 (−), and Di-Fuc-$sLe^x$ (+); and
$Le^x$ (+), $sLe^x$ (−), VIM-2 (−), and Di-Fuc-$sLe^x$ (−)

where the symbol "(+)" indicates the presence of a fucosylated lactosaminyl glycan and the symbol "(−)" indicates the absence of a fucosylated lactosaminyl glycan.

According to some embodiments, the presence (+) or absence (−) of a glycan is determined using a negative control. For example, FIG. 6 discloses flow cytometry data measuring mean fluroescence intensity (MFI) of various glycans in a population of cells after being transfected with a fucosyltransferase or not transfected (NT). In this particular example, the negative control is the non-transfected (NT) group. According to some embodiments, the determination of whether a glycan is present (+) or absent (−) is made by evaluating the statistical significance of the measured glycan (by MFI) relative to a negative control. According to some embodiments, one or more of ANOVA, t-tests, F-tests, among others, may be used to determine the statistical significance of a glycan measurement. According to some embodiments, if the glycan is measured to be statistically significant (ANOVA ($p<0.05$)) compared to values obtained from that of a negative control, the glycan is present (+). If the glycan is measured as not being statistically significant (ANOVA ($p>0.05$)) above a negative control, the glycan is not present (−).

According to some embodiments, the presence or absence of fucosylated lactosaminyl glacans can be enforced in one or more of the following patterns:

TABLE 2

| Pattern No. | $Le^x$ | $sLe^x$ | VIM-2 | Difucosyl $sLe^x$ |
|---|---|---|---|---|
| 1 | + | + | + | + |
| 2 | + | + | − | − |
| 3 | + | + | − | + |
| 4 | − | + | − | + |
| 5 | + | − | − | − |

In some embodiments, the enforced fucosylated lactosaminyl glycan comprises varying amounts of $sLe^x$, $Le^x$, VIM-2, and Di-Fuc-$sLe^x$ relative to each other. In some embodiments, a predetermined balance of $Le^x$ expression and/or $sLe^x$ expression, or a predetermined balance of any other of the various combinations of $Le^x$, $sLe^x$, VIM-1, and difucosyl $sLe^x$ glycan determinants can be enforced. For example, the enforced pattern of fucosylated lactosaminyl glycans may be represented using the notation:
$Le^x$(+)>>$sLe^x$ (+), VIM-2 (−), and Di-Fuc-$sLe^x$ (−);
$sLe^x$ (+)>>$Le^x$(+), VIM-2 (−), and Di-Fuc-$sLe^x$ (+);
$sLe^x$(+), $Le^x$(−), VIM-2 (−), and Di-Fuc-$sLe^x$ (+);
$Le^x$(+), $sLe^x$ (−), VIM-2 (−), and Di-Fuc-$sLe^x$ (−);
$sLe^x$ (+)>$Le^x$(+), VIM-2 (+), and Di-Fuc-$sLe^x$ (+),
where the symbol ">" indicates more of one glycan relative to another glycan and the symbol ">>" indicates substantially more of one glycan relative to another glycan. As a guide to how each of the above-identified patterns is generated, reference is made to FIGS. 6A to 6D in which relative amounts of cell surface glycans are measured in response to specific enzymes.

According to some embodiments, the determination by flow cytometry of whether a greater amount of a certain glycan (a "first" glycan) is present relative to another glycan (a "second" glycan) is made by evaluating the statistical significance (compared to the untreated control) of the measured mean channel fluorescence amounts of the first and second glycan. If a glycan is measured as having an average MFI of 3-fold or more than the negative control, that glycan is denoted (++). If a glycan is measured as having a MFI of more than 20-fold than the negative control, that glycan is denoted (+++). Thus, a comparison of the relative amounts of glycan can be made by comparing increase MFI over negative controls. For example, a glycan having a (++) amount is greater than (>) a glycan having a (+) amount. Similarly, a glycan having a (+++) amount is substantially greater than (>>) a glycan having a (+) or a (++) amount. For example, the notation Le$^x$(+)>>sLe$^x$ (+) indicates substantially more Le$^x$ is present relative to sLe$^x$. As another example, the notation sLe$^x$(+)>Le$^x$(+) indicates that more sLe$^x$ is present relative to Le$^x$. The relative amounts of glycan can be determined by relative MFI values as obtained by flow cytometry, mass spectrometry (in some embodiments in combination with other modalities such as liquid chromatography, i.e., LC-MS), or any other method known in the art for quantification of cell surface moieties. For example, the amount of glycan can be quantified by mean fluorescence intensity (MFI) units, such as geometric mean fluorescence intensity units, or median fluorescence intensity units in combination with immunofluorescence staining and quantification by flow cytometry.

According to some embodiments, the relative amounts of fucosylated lactosaminyl glycans are enforced in one or more of the following patterns:

TABLE 3

| Pattern No. | Le$^x$ | sLe$^x$ | VIM-2 | Difucosyl sLe$^x$ |
|---|---|---|---|---|
| 1 | ++ | ++ | ++ | + |
| 2 | +++ | + | – | – |
| 3 | + | ++ | ++ | + |
| 4 | ++ | +++ | – | ++ |
| 5 | – | +++ | – | + |
| 6 | +++ | – | – | – |

According to some embodiments, the fucosylated lactosaminyl glycan may be "N-linked" (e.g. linked through N-Acetylglucosamine to the amino acid asparagine), "O-linked" (e.g. linked through N-Acetylgalactosamine to the amino acid serine or threonine), or displayed on glycosphingolipids (GSLs). By LC-MS analysis, it is possible to provide a relative (semi-quantitative) ratio of expression glycans displayed as O-glycans and GSLs, but MS profiles of N-glycans do not provide quantitative data. As shown in FIG. 8B, in some embodiments the enforced glycan pattern comprises O-linked glycans having the relative amounts of:
(i) Le$^x$(+)>>sLe$^x$ (+), and Di-Fuc-sLe$^x$ (–);
(ii) sLe$^x$ (+)>Le$^x$(+), and Di-Fuc-sLe$^x$ (–);
(iii) sLe$^x$(+), Le$^x$(–), and Di-Fuc-sLe$^x$ (–);
(iv) Le$^x$(+), sLe$^x$ (–), and Di-Fuc-sLe$^x$ (–);
(v) Le$^x$ (+)>sLe$^x$(+), and Di-Fuc-sLe$^x$ (–).

In some embodiments, the enforced glycan pattern comprises N-linked glycans comprising the pattern: (i) Le$^x$(+), sLe$^x$ (+), and Di-Fuc-sLe$^x$ (+); or (ii) Le$^x$ (+), sLe$^x$(+), and Di-Fuc-sLe$^x$ (–). (FIG. 8B)

In some embodiments, the enforced glycan pattern comprises glycosphingolipids (GSLs) comprising the pattern: (i) Le$^x$(+), sLe$^x$ (–), and Di-Fuc-sLe$^x$ (–); (ii) Le$^x$ (–), sLe$^x$(–), and Di-Fuc-sLe$^x$ (–); (iii) Le$^x$(+), sLe$^x$ (+), and Di-Fuc-sLe$^x$ (–); (iv) sLe$^x$(+), Le$^x$(–), and Di-Fuc-sLe$^x$ (–). (FIG. 8B)

According to some embodiments, a desired ratio of certain glycan structures can be enforced on the surface of a living cell. For example, the ratio of one glycan structure to another (such as sLe$^x$:Le$^x$, Le$^x$:sLe$^x$, sLe$^x$:Di-Fc-sLe$^x$, Le$^x$:Di-Fc-sLe$^x$, etc.) may be at least 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, or more.

According to some embodiments, the pattern of fucosylated lactosaminyl glycan can be enforced by a member of the α(1,3)-fucosyltransferase family. The α(1,3)-fucosyltransferase family includes Fucosyltransferase III (also called FTIII, FT3, FUTIII, FUT3), Fucosyltransferase IV (also called FTIV, FT4, FUTIV, FUT4), Fucosyltransferase V (also called FTV, FT5, FUTV, FUT5), Fucosyltransferase VI (also called FTVI, FT6, FUTVI, FUT6), Fucosyltransferase VII (also called FTVII, FT7, FUTVII, FUT7), Fucosyltransferase IX (also called FTIX, FT9, FUTIX, FUT94), and variants thereof. The cDNA/protein sequences for the α(1,3)-fucosyltransferase family are as follows:

TABLE 4

| Name | GenBank Acc. No. | ID NO: |
|---|---|---|
| Fucosyltransferase III (FUT3; FT3) | BC108675 | SEQ ID NO: 1 (AA) |
|  |  | SEQ ID NO: 2 (cDNA) |
| Fucosyltransferase IV (FUT4; FT4) | BC136374 | Long |
|  |  | SEQ ID NO: 3 (AA) |
|  |  | SEQ ID NO: 4 (cDNA) |
|  |  | Short |
|  |  | SEQ ID NO: 5 (AA) |
|  |  | SEQ ID NO: 6 (cDNA) |
| Fucosyltransferase V (FUT5; FT5) | BC140905 | SEQ ID NO: 7 (AA) |
|  |  | SEQ ID NO: 8 (cDNA) |
| Fucosyltransferase VI (FUT6; FT6) | BC061700 | SEQ ID NO: 9 (AA) |
|  |  | SEQ ID NO: 10 (cDNA) |
| Fucosyltransferase VII (FUT7; FT7) | BC074746 | SEQ ID NO: 11 (AA) |
|  |  | SEQ ID NO: 12 (cDNA) |
| Fucosyltransferase IX (FUT9; FT9) | BC036101 | SEQ ID NO: 13 (AA) |
|  |  | SEQ ID NO: 14 (cDNA) |

As used herein, the notation for a fucosyltransferase should not be construed as limiting to the nucleotide sequence or the amino acid sequence. For example, the notation of Fucosyltransferase IX, FTIX, FT9, FUTIX or FUT9 are used interchangeably as meaning the nucleotide, amino acid sequence, or both, of Fucosyltransferase IX.

According to some embodiments, cells are contacted by one or more of the α(1,3)-fucosyltransferase family members to enforce a specific pattern of fucosylated lactosaminyl glycans. As used herein, the term "contact" (and grammatical variations thereof) of an enzyme with a cell to enforce a specific pattern of glycans includes any form of bringing an enzyme into proximity with its substrate so as to allow for enzymatic activity. For example, cells contacted by one or more α(1,3)-fucosyltransferase family members to enforce a specific pattern of fucosylated lactosaminyl glycans includes, but is not limited to, direct contact of the α(1,3)-fucosyltransferase with cell surface substrates by exofucosylation, and also includes contact of the α(1,3)-fucosyltransferase with intracellular substrates by any means of introducing nucleic acid (e.g., transfection, electroporation, transduction) encoding the α(1,3)-fucosyltransferase into a cell. The contacting can be together (i.e., introducing a nucleic acid encoding a given fucosyltransferase together with cell surface exofucosylation using the same (or another) fucosyltransferase).

In some embodiments, fragments of α(1,3)-fucosyltransferase family members are contacted with a cell. For example, a peptide/nucleotide having at least 50%, 60%, 70%, 80%, 90%, 95%, 96%, 97%, 98%, or 99% identity to an α(1,3)-fucosyltransferase family member is contacted with a cell. As used herein, the term "identity" and grammatical versions thereof means the extent to which two nucleotide or amino acid sequences have the same residues at the same positions in an alignment. Percent (%) identity is calculated by multiplying the number of matches in a sequence alignment by 100 and dividing by the length of the aligned region, including internal gaps.

According to some embodiments, the enforced pattern of fucosylated lactosaminyl glycans can be detected by reactivity to one or more antibodies. For example, the sLe$^x$, Le$^x$, VIM-2, and Di-Fuc-sLe$^x$ may be detected by one or more of the HECA-452 antibody (ATCC HB-11485) and/or CSLEX1 antibody (clone CSLEX1, BD Pharmingen, Billerica, MA), the HI98 antibody (clone HI98, Biolegend, San Diego, CA), the VIM-2 antibody (clone VIM-2, Bio-Rad), and the FH6 antibody (clone FH6, BioLegend), respectively. Other antibodies known in the art that bind to sLe$^x$, Le$^x$, VIM-2, and Di-Fuc-sLe$^x$ motifs may also be used.

According to some embodiments, a specific α(1,3)-fucosyltransferase enforces a specific pattern of fucosylated lactosaminyl glycan. For example, the enforced glycan pattern comprises one of the following:

TABLE 5

| FUT No. | Le$^x$ | sLe$^x$ | VIM-2 | Difucosyl sLe$^x$ |
|---|---|---|---|---|
| FUT3 | ++ | ++ | ++ | + |
| FUT4 | +++ | + | − | − |
| FUT5 | + | ++ | ++ | + |
| FUT6 | ++ | +++ | − | ++ |
| FUT7 | − | +++ | − | + |
| FUT9 | +++ | − | − | − |

According to some embodiments, a specific α(1,3)-fucosyltransferase enforces a specific pattern of fucosylated lactosaminyl glycan, wherein more of one glycan moiety is present than another. For example, the enforced glycan pattern comprises one of the following:

TABLE 6

| FUT No. | Fucosylated Lactosaminyl Glycan Pattern |
|---|---|
| FUT3 | sLe$^x$ (+) > Le$^x$(+), VIM-2 (+), Di-Fuc-sLe$^x$ (+) |
| FUT4 | Le$^x$(+) >> sLe$^x$ (+), VIM-2 (−), Di-Fuc-sLe$^x$ (−) |
| FUT5 | sLe$^x$ (+) > Le$^x$(+), VIM-2 (+), Di-Fuc-sLe$^x$ (+) |
| FUT6 | sLe$^x$ (+) >> Le$^x$(+), VIM-2 (−), and Di-Fuc-sLe$^x$ (+) |
| FUT7 | sLex(+), Lex(−), VIM-2 (−), Di-Fuc-sLe$^x$ (+) |
| FUT9 | Le$^x$(+), sLe$^x$ (−), VIM-2 (−), Di-Fuc-sLe$^x$ (−) |

The present disclosure also provides a process for custom engineering of a cell to have a specific desired glycosylation pattern. According to some embodiments, a glycosylation pattern can be selected based on the identified patterns, disclosed herein, resulting from contacting a cell with one or a combination of defined α(1,3)-fucosyltransferase family member(s). In some embodiments, the selected identified pattern can be enforced by contacting the cell with a single α(1,3)-fucosyltransferase family member. For example, the process for custom engineering a fucosylated lactosaminyl glycan may comprise selecting a pattern from the group disclosed in TABLE 3 then selecting the α(1,3)-fucosyltransferase capable of producing the desired glycosylation pattern, disclosed herein, and contacting a target cell with the selected α(1,3)-fucosyltransferase.

Alternatively, two or more α(1,3)-fucosyltransferases may be used to enforce a unique glycosylation pattern on a human cell. According to some embodiments, this can be achieved by determining a desired glycosylation pattern for a target human cell and contacting the target cell with the appropriate α(1,3)-fucosyltransferases based on the enforced glycosylation patterns disclosed herein. For example, to achieve Le$^x$(+), sLe$^x$(+), VIM-2(−), and Di-Fuc-sLe$^x$(+) on a human cell, one can contact the human cell with Fucosyltransferase VII and Fucosyltransferase IX, either consecutively or concurrently.

According to some embodiments, a cell is selectively tuned to express a distinct glycan pattern by contacting with one or more specific α(1,3)-fucosyltransferases. In some embodiments, the distinct glycan patterns may be achieved by contacting with the following α(1,3)-fucosyltransferases according to TABLE 5.

According to some embodiments, relative amounts of glycan may be enforced on a cell by contacting with one or more specific α(1,3)-fucosyltransferases. In some embodiments, relative amounts of glycan patterns may be achieved by contacting with the following α(1,3)-fucosyltransferases according to TABLE 6.

In some embodiments, the process for custom engineering of a fucosylated lactosaminyl glycan pattern comprises selecting a desired combination glycosylation pattern for a target human cell based on established glycan pattern, and contacting the target human cell with the combination of α(1,3)-fucosyltransferases capable of producing the desired glycosylation pattern. Some non-limiting examples of possible combination selections and glycan profile outcomes can be seen in the table below.

TABLE 7

| α(1,3)-fucosyltransferases | Le$^x$ | sLe$^x$ | VIM-2 | Di-Fuc-sLe$^x$ |
|---|---|---|---|---|
| FUT7 and FUT4 | +++ | +++ | − | + |
| FUT7 and FUT9 | | | | |
| FUT3 and FUT6 | ++ | +++ | ++ | ++ |
| FUT5 and FUT6 | | | | |
| FUT6 and FUT9 | +++ | +++ | − | ++ |

As is apparent in the above table, by selecting individual or combinations of α(1,3)-fucosyltransferases for contacting with cells, it is possible to create glycan patterns that would not otherwise exist on human cells. Furthermore, by selecting combinations of α(1,3)-fucosyltransferases for contacting with cells, it is possible to create glycan patterns that cannot be achieved by contacting the cells with a single α(1,3)-fucosyltransferase. In this manner, it is possible to custom engineer cells with diverse combinations of glycans and glycan amounts.

Various Methods can be Used to Contact a Cell with a Fucosyltransferase to Enforce a Pattern of Cell Surface Fucosylated Lactosaminyl Glycans In some embodiments, the cells are contacted with the desired fucosyltransferase via exofucosyltation. For example, U.S. Pat. Nos. 7,875,585 and 8,084,236, provide compositions and methods for ex vivo modification of cell surface glycans on a viable cell, which may be used to enforce a pattern of cell surface fucosylated lactosaminyl glycans on a cell. In some embodiments, the compositions include a purified glycosyltransferase polypeptide and a physiologically acceptable solution, for use together with appropriate donor nucleotide sugars in reaction buffers and reaction conditions specifically formulated to retain cell viability. In some embodiments, the physiologically acceptable solution is free or substantially free of divalent metal co-factors, to such extent that cell viability is not compromised. In these and other embodiments, the composition is also free or substantially free of stabilizer compounds such as for example, glycerol, again, to such extent that cell viability is not compromised. Glycosyltransferases include for example, fucosyltransferase. In one embodiment, the fucosyltransferase is an α(1,3)-fucosyltransferase such as an α(1,3)-fucosyltransferase III, α(1,3)-fucosyltransferase IV, an α(1,3)-fucosyltransferase V, an α(1,3)-fucosyltransferase VI, an α(1,3)-fucosyltransferase VII or an α(1,3)-fucosyltransferase IX. In some embodiments, an additional glycosyltransferase and/or glycosidase is used to enforce the pertinent acceptor lactosaminyl glycan, upon which a fucosyltransferase could then add a fucose moiety. The glycosyltransferases and glyocosidases capable of forming lactosaminyl glycans (upon with fucose can be added by fucoyltransferase) are well known in the art. In some embodiments, α(2,3)-sialyltransferases such as ST3GalIII, ST3GalIV, and ST3GalVI, can be used to convert unsialylated (i.e., "neutral") terminal Type 2 lactosaminyl glycans into α(2,3)-sialylated Type 2 lactosaminyl glycans, which could then be fucosylated by the fucosyltransferase(s) to create pertinent sialofucosylated lactosaminyl glycans. In some embodiments, a sialidase can be used (e.g., an α(2,3)-sialidase, or an α(2,3/2,6/2,8)-sialidase (such as sialidase from *Vibrio cholerae* (e.g. 0.1 U/ml; Roche)) to cleave terminal α(2,3)-sialic acid and/or terminal α(2,3)-linked, α(2,6)-linked or α(2,8)-linked sialic acid(s) off of sialylated type 2 lactosamines, thereby creating "neutral" type 2 lactosamine termini; these termini could then be fucosylated to create LeX, or, in the case of (originally) α(2,6)-linked or α(2,8)-linked lactosamines, resialylated by α(2,3)-sialyltransferases to create α(2,3)-sialylated Type 2 lactosaminyl glycans, which could then be fucosylated by the fucosyltransferase(s) to create pertinent sialofucosylated lactosaminyl glycans. In some embodiments, a hexosaminidase may be used to cleave N-acetylgalactosamine from the Sda antigen (GalNAc-β(1,4)-[Neu5Ac-α(2,3)]-Gal-β(1,4)-GlcNAc-R) to render substrate α(2,3)-sialylated Type 2 lactosaminyl glycans, which could then be fucosylated by the fucosyltransferase(s) to create pertinent sialofucosylated lactosaminyl glycans. In some embodiments, the contacting of the combination of fucosyltransferase and addition glycosyltrasferase/glycosidase occurs simultaneously or sequentially.

According to some embodiments the human cells may be contacted with a desired fucosyltransferase by transfecting a DNA or RNA nucleotide sequence encoding the desired fucosyltransferase into the cell. According to some embodiments, modified RNA (modRNA) encoding the relevant α(1,3)-FT transcripts is used to enforce the desired pattern of fucosylated lactosaminyl glycans. In some embodiments, the transfected nucleotide sequence encodes a full length or partial peptide sequence of the desired fucosyltransferase. In some embodiments, the nucleotide sequence encodes a naturally existing isoform of a fucosyltransferase.

According to some embodiments, the cells may be contacted with the desired fucosyltanferase by transfecting a recombinant DNA or RNA molecule. As used herein, the term "recombinant DNA or RNA" means a DNA or RNA molecule formed through recombination methods to splice fragments of DNA or RNA from a different source or from different parts of the same source. In some embodiments the recombinant DNA may comprise a plasmid vector, which controls expression of the DNA in the cell.

In some embodiments, glycans are modified on the surface of a cell by contacting a population of cells with one or more glycosyltransferase compositions described above. In some embodiments, the cells are contacted with the glycosyltransferase composition together with appropriate nucleotide sugar donor (e.g., GDP-fucose, CMP-sialic acid) under conditions in which the glycosyltransferase has enzymatic activity. Glycan modification according to this method results in cells that have at least 70%, 75%, 80%, 85%, 90%, 95%, 96%, 97%, 98%, 99% or more viability at 24 hours or more after treatment. In one embodiment, for example, the cells have at least 70% viability at 48 hours after treatment. In one such embodiment, for example, the cells have at least 75% viability at 48 hours after treatment. In one embodiment, for example, the cells have at least 80% viability at 48 hours after treatment. In addition, the phenotype of the cells (other than the glycan modification) is preferably preserved after treatment. By preserved phenotype it is meant the cell maintains its native function and/or activity. For example, if the cell is a stem cell it retains its potency, i.e., its relevant totipotency or pluripotency or multipotency or unipotency, as would be characteristic of that particular stem cell type.

According to some embodiments, glycosyltransferases are contacted with cells in the absence of divalent metal co-factors (e.g. divalent cations such as manganese, magnesium, calcium, zinc, cobalt or nickel) and stabilizers such as glycerol. In some embodiments, a purified glycosyltransferase polypeptide and a physiologically acceptable solution free of divalent metal co-factors is used to enforce a desired glycosylation pattern. The composition is free of stabilizer compounds such as for example, glycerol, or the composition contains stabilizers at levels that do not affect cell viability. Glycosyltransferase contacted with cell in the absence of divalent metal cofactors include for example, α(1,3)-fucosyltransferase such as an α 1,3 fucosyltransferase III, α 1,3 fucosyltransferase IV, an α 1,3 fucosyltransferase VI, an α 1,3 fucosyltransferase VII or an α 1,3 fucosyltransferase IX). In some embodiments, the composition further includes a sugar donor suitable for the specific glycosyltransferase. For example, when the glycoslytransferase is a fucosyltransferase, the donor is GDP-fucose. According to some embodiments, the glycosyltransferase is biologically active. By biologically active means that the glycosyltransferase is capable of transferring a sugar molecule from a donor to acceptor. For example, the glycosyltransferase is capable of transferring 0.1, 0.2, 0.3, 0.4, 0.5, 1.0, 1.5, 2.0, 2.5, 5, 10 or more µmoles of sugar per minute at pH 6.5 at 37° C. In some embodiments, the contacting of a glycosyltranferase with a cell occurs in a physiologically acceptable solution, which is any solution that does not cause cell damage, e.g. death. For example, the viability of the cell is at least 80%, 85%, 90%, 95%, 96%, 97%, 98%, 99% or more after treatment with the compositions of the invention. Suitable physiologically acceptable solutions include, for example, Hank's Balanced Salt Solution (HBSS), Dulbecco's Modified Eagle Medium (DMEM), a Good's buffer (see 104; 105) such as a HEPES buffer, a 2-Morpholinoethanesulfonic acid (WS) buffer, or phosphate buffered saline (PBS).

Functionalized Fucose Deposited on the Cell Surface

The present disclosure also provides methods and compositions for directing the placement upon a cell surface lactosaminyl glycan of a GDP-fucose donor wherein the fucose is modified with a chemically-reactive tag (e.g., a functional group serving as a chemical reporter) which would then allow subsequent conjugation with another structure (e.g., via a bioorthogonal chemical reaction) and/or wherein the fucose with GDP-fucose is linked (modified covalently) prior to introduction onto the cells with one or more additional molecules that confer a desired biologic property. In such embodiments, the use of the α(1,3)-FTs confers both regiospecificity and stereospecificity in the placement of the pertinent molecular moiety which is linked to the installed fucose.

In some embodiments, the modified (functionalized) fucose comprises a uniquely reactive chemical handle that is displayed on the cell surface after the modified fucose is introduced onto a cell (e.g. via fucosyltransferase). The chemical handle will react only when exposed to a reagent or moiety that has a matched reactivity. Thus, according to some embodiments, the modified fucose may be engineered to bear any molecule having (or engineered to have) the concomitant reactivity. According to some embodiments, the modified fucose is effective for chemoselective-ligation reactions that are well known in the art to selectively form a covalent linkage in a biological medium. (See, e.g., 106)

According to some embodiments, stereospecific addition of a molecular tag-modified donor nucleotide fucose allows for subsequent linkage of other molecules onto the installed fucose in a distinct pattern onto cell surface lactosaminyl glycans. In some embodiments, molecules containing distinct biologic properties can be covalently linked to the donor nucleotide fucose and can thus be stereospecifically added in a distinct pattern onto cell surface lactosaminyl glycans. For example, molecules containing distinct biological properties can be covalently linked to fucose of $Le^x$, $sLe^x$, VIM-2, and Difucosyl-$sLe^x$ in patterns according to TABLES 2, 3, 5, 6, or 7.

In some embodiments, the functionalized fucose used in conjunction with one or more fucosyltransferases is an azide- or alkyne-tagged fucose. For example, in some embodiments a GDP-azido-fucose is used. Any azido-fucose analogue known in the art may be used (e.g., GDP-Azido-Fucose, R&D Systems, Bio-Techne Corporation, Cat. No. ES101-100). According to some embodiments, fucose-alkyne is used. Any fucose-alkyne analogue known in the art may be used (e.g. Click-IT Fucose Alkyne, Thermo Fisher, At. No. C10264) According to some embodiments, the alkyne or azide tagged fucose is further conjugated to another molecule. For example, after depositing an azido-fucose onto the surface of a cell using one or more fucosyltransferases, the azido fucose may be conjugated to biotinylated alkyne. The resulting covalently bound biotinylated fucose may then be used to attach any avidin/streptavidin-bound molecule known in the art. Addition of a donor GDP-fucose wherein the fucose has been modified by methods known in the art with a chemical reactive group/molecular tag (e.g., biotinylated GDP-fucose, azido-GDP-fucose, etc.) thereby allowing for subsequent linkage of other molecules onto the installed fucose within cell surface lactosaminyl glycans (examples of this approach include, but are not limited to, utility of biotinylated GDP-fucose with subsequent complexing using streptavidin-conjugated molecules and/or use of "click chemistry" wherein the azido-containing fucose molecule is then complexed to an alkyne-containing molecule). In other embodiments, molecules covalently linked to the donor nucleotide fucose (i.e., GDP-fucose with covalent attachment of additional molecule(s)) can be stereospecifically added in a distinct pattern onto cell surface lactosaminyl glycans to endow a desired biologic property upon the cell.

According to some embodiments, the conjugation of azido-fucose to a biotin moiety is performed via copper mediated click chemistry, as known in the art. For example, for each reaction, 20 nmol of Cu2+, 10 nmol of biotinylated alkyne and 200 nmol of ascorbic acid may be combined at room temperature to allow the Cu2+ to reduce to Cu+. The mixture may then be diluted in 25 mM Tris, 150 nM NaCl at pH 7.5, and then applied for 30 minutes to cells having azido-fucose deposited on the cell surface (e.g., by exofucosylation). The reaction solution may then be removed and cells washed. The resulting biotinylated fucose may then be further conjugated to additional molecules of interest via interaction with biotin. (See, e.g., 107)

The structures that may be conjugated to fucose after being deposited on the cell surface according to embodiments disclosed herein include, but are not limited to, peptides, proteins, nucleotides, polynucleotides, carbohydrates, lipids, antibodies (such as IgA, IgD, IgE, IgG, IgM, and fragments thereof), drugs, probes, and combinations thereof.

Characterization and Isolation of Defined Cell Subsets from a Heterogenous Mixture The present disclosure also provides methods for selecting distinct patterns of expression of fucosylated lactosamines installed on the cell and isolating defined cell subsets within a heterogenous mixture of cells. As disclosed herein, cells undergo monosaccharide modification in response to a glycosyltransferase acting on its relevant acceptor. The specific pattern of a given glycan determinant after contact with a glycosyltransferase (such as fucosyltransferase) thus reflects the presence of the pertinent underlying glycan-acceptor, thus defining the "glycosignature" of a cell (i.e., the presence of a product after glycosyltransferase treatment defines the presence of that acceptor in the target cell (111)). According to some embodiments, the amount of a given glycan determinant engendered by glycosyltransferase is used to identify and select distinct subsets of cells. According to some embodiments, cells are selected on the basis of range/level of pertinent glycan determinant enforced by monosacharride substitution (such as by contacting the cell with a relevant glycosyltransferase), and isolated to capture a distinct subset of cells within a complex mixture that display either high expression levels or low expression levels of the pertinent product glycan In some embodiments, the distinct patterns of expression of fucosylated lactosamines installed on the cell surface by contacting cells with one or more α(1,3)-fucosyltransferases can be used to characterize and isolate defined cell subsets within a heterogenous mixture of cells.

According to some embodiments, the selection of populations and/or sub-populations of cells is performed using any technique known in the art, such as fluorescence activated cell sorting (FACS). For example, if FACS is used for selection, cells that express the highest or lowest amount of a glycan as measured by the spectrum/range of mean fluorescence intensity (MFI) may be selected. According to some embodiments, sub-population(s) of cells from a heterogeneous population having a particular glycan pattern (e.g. fucosylated lactosaminyl glycan pattern) may be selected based on the amount of expression of one or more glycans (e.g. $Le^x$, $sLe^x$, VIM-2, Di-Fucosyl-$sLe^x$). According to some embodiments, a sub-population of cells is selected for expressing a high amount of a given glycan, such as the sub-population expressing more of the given glycan, e.g., greater than that of 90 percent of cells in the heterogeneous population (upper 10th percentile). According to some embodiments, a sub-population of cells is selected for expressing a low amount of a given glycan, such as the sub-population expressing less of a given glycan, e.g., at a level below the lower 10th percentile in the heterogeneous population.

According to some embodiments, the cells of a heterogenous population having a fucosylated lactosaminyl glycan pattern (such as those according to any of TABLES 2, 5, 6, or 7) are selected based on the amount of any one or a combination of $Le^x$, $sLe^x$, VIM-2, or Di-Fucosyl-$sLe^x$ in the cells. In some embodiments the sub-population of human cells may be selected for expression of one or more of $Le^x$, sLe$^x$, VIM-2, or Di-Fucosyl-sLe$^x$ expressed in the upper 50th, 40th, 30th, 20th, 10th, 5th, or 1st percentile or greater of the heterogenous population. In some embodiments, the sub-population of cells is selected for expression of one or more of Le$^x$, sLe$^x$, VIM-2, or Di-Fucosyl-sLe$^x$ in the lower 50th, 40th, 30th, 20th, 10th, 5th, or 1st percentile of the heterogenous population. According to some embodiments, more than one glycan is used to select a sub-population of cells. Any glycan may be used in combination with any other glycan for selection of the sub-population. In one non-limiting example, Le$^x$ may be used in combination with (1) sLe$^x$; (2) sLe$^x$ and VIM-2; or (3) sLe$^x$, VIM-2, and Di-Fucosyl-sLe$^x$. As another non-limiting example, sLe$^x$ may be used in combination with (1) VIM-2; or (2) VIM-2, and Di-Fucosyl-sLe$^x$. Other non-limiting examples include, (1) a sub-population of cells may be selected for expressing Le$^x$ in the upper 10th percentile or greater and sLe$^x$ in the lower 10th percentile or lower; (2) a sub-population of cells may be selected for expressing Le$^x$ in the lower 10th percentile or lower and sLe$^x$ in the upper 10th percentile or greater; (3) a sub-population of cells may be selected for expressing Le$^x$ in the upper 10th percentile or greater and sLe$^x$ in the upper 10th percentile or greater; or (4) a sub-population of cells may be selected for expressing Le$^x$ in the lower 10th percentile or lower and sLe$^x$ in the lower 10th percentile or lower. Any permutation of glycan and percentile of expression may be used as the basis for cell selection.

The present disclosure provides a method of selecting human cells comprising the steps of (a) providing a population of human cells; (b) contacting the population of human cells with one or more $\alpha(1,3)$-fucosyltransferase(s), detecting the fucosylated lactosaminyl glycans Le$^x$, sLe$^x$, VIM-2, and Di-Fuc-sLe$^x$ on the population of human cells; and identifying the population of human cells as having a fucosylated lactosaminyl glycan pattern, such as shown in TABLES 2, 5, 6, or 7. In some embodiments, the method further comprises the step of selecting a sub-population from the population of human cells having the fucosylated lactosaminyl glycan pattern, such as shown in TABLES 2, 5, 6, or 7.

Cell Types

Any type of human cell can be used in the methods described herein. For example, according to some embodiments the cell is a hepatocyte (e.g. a primary hepatocyte), a neuronal cell (e.g. a primary neuronal cell), a myoblast (e.g. a primary myoblast), a mesenchymal stem cell (e.g. a primary mesenchymal stem cell), or a progenitor cell (e.g. a primary progenitor cell). In some embodiments, the cell type includes, but is not limited to, embryonic stem cells, adult stem cells, induced pluripotent stem cells, blood progenitor cells, tissue progenitor cells, epithelial, endothelial, neuronal, adipose, cardiac, skeletal muscle, fibroblast, immune cells (for example, dendritic cells, monocytes, macrophages, leukocytes (e.g., a lymphocyte such as a B-lymphocyte, a T-lymphocyte, or a subset of T-lymphocytes, such as regulatory lymphocyte (e.g., CD4$^+$/CD25$^+$/FOXP3$^+$ cells, Breg cells, etc.), a naive T cell, a central memory T cell, an effector memory T cell, an effector T cell, NK cells, etc.), hepatic, splenic, lung, circulating blood cells, platelets, reproductive cells, gastrointestinal cells, renal cells, bone marrow cells, cardiac cells, endothelial cells, endocrine cells, skin cells, muscle cells, neuronal cells, and pancreatic cells. The cell can be an umbilical cord stem cell, an embryonic stem cell, or a cell isolated from any tissue (such as a primary cell) including, but not limited to brain, liver, lung, gut, stomach, fat, muscle, testes, uterus, ovary, skin, spleen, endocrine organ and bone, and the like. The cell can be culture-expanded and/or modified in vitro by introduction of any nucleic acid sequence encoding a protein of interest.

Where the cell is maintained under in vitro conditions, conventional tissue culture conditions and methods can be used, and are known to those of skill in the art. Isolation and culture methods, and cell expansion methods, for various cells are well within the knowledge of one skilled in the art. Moreover, various cells that contain nucleic acid encoding desired protein products are also incorporated (e.g., CAR-T cells).

In addition, both heterogeneous and homogeneous cell populations are contemplated for use with the methods and compositions described herein. In addition, aggregates of cells, cells attached to or encapsulated within particles, cells within injectable delivery vehicles such as hydrogels, and cells attached to transplantable substrates (including scaffolds) or applied into tissue(s) that harbors scaffolds/transplantable substrates are contemplated for use with the methods and compositions described herein. Moreover, cells may be used in combination with tissue proliferative/enhancing agents and/or anti-inflammatory agents (e.g., growth factors, cytokines, prostaglandins, trophic agents, Resolvins, NSAIDS, steroids, etc.)

Administration of Cell Populations Described Herein

Administration of cell populations described herein for therapeutic indications can be achieved in a variety of ways, in each case as clinically warranted/indicated, using a variety of anatomic access devices, a variety of administration devices, and a variety of anatomic approaches, with or without support of anatomic imaging modalities (e.g., radiologic, MRI, ultrasound, etc.) or mapping technologies (e.g., epiphysiologic mapping procedures, electromyographic procedures, electrodiagnostic procedures, etc.). Cells can be administered systemically, via either peripheral vascular access (e.g., intravenous placement, peripheral venous access devices, etc.) or central vascular access (e.g., central venous catheter/devices, arterial access devices/approaches, etc.). Cells can be delivered intravascularly into anatomic feeder vessels of an intended tissue site using catheter-based approaches or other vascular access devices (e.g., cardiac catheterization, etc.) that will deliver a vascular bolus of cells to the intended site. Cells can be introduced into the spinal canal and/or intraventricularly intrathecally, into the subarachnoid space to distribute within cerebrospinal fluid and/or within the ventricles). Cells can be administered directly into body cavities or anatomic compartments by either catheter-based approaches or direct injection (e.g., intraperitoneal, intrapleural, intrapericardial, intravesicularly (e.g., into bladder, into gall bladder, into bone marrow, into biliary system (including biliary duct and pancreatic duct network), intraurethrally, via renal pelvis/intraureteral approaches, intravaginally, etc.)). Cells can be introduced by direct local tissue injection, using either intravascular approaches (e.g., endomyocardial injection), or percutaneous approaches, or via surgical exposure/approaches to the tissue, or via laparoscopic/thoracoscopic/endoscopic/colonoscopic approaches, or directly into anatomically accessible tissue sites and/or guided by imaging techniques (e.g., intra-articular, into spinal discs and other cartilage, into bones, into muscles, into skin, into connective tissues, and into relevant tissues/organs such as central nervous system, peripheral nervous system, heart, liver, kidneys, spleen, etc.). Cells can also be placed directly onto relevant tissue surfaces/sites (e.g., placement onto tissue directly, onto ulcers, onto burn surfaces, onto serosal or mucosal surfaces, onto epicardium, etc.). Cells can also administered into tissue or structural support devices (e.g., tissue scaffold devices and/or embedded within scaffolds placed into tissues, etc.), and/or administered in gels, and/or administered together with enhancing agents (e.g., admixed with supportive cells, cytokines, growth factors, resolvins, anti-inflammatory agents, etc.).

According to some embodiments, the cell population is administered to the subject with an enforced expression pattern of glycosylation. According to some embodiments, the enforced glycosylation pattern on the surface of administered cells will aid in revascularization, in host defense (e.g., against infection or cancer) and/or in tissue repair/regeneration and/or mediate immunomodulatory processes that will dampen inflammation and/or prevent inflammation. According to some embodiments, the enforced glycosylation pattern guides delivery of intravascularly administered cells to sites of inflammation by mediating binding of blood-borne cells to vascular E-selectin expressed on endothelial cells at sites of inflammation. Moreover, whether cells are administered systemically, intravascularly, into the spinal canal and/or intraventricularly intrathecally, into the subarachnoid space to distribute within cerebrospinal fluid), directly into body cavities or compartments, by direct local tissue injection, or by placement onto relevant tissue surfaces/sites, the enforced expression pattern of ligands for E-selectin and/or L-selectin on administered cells promotes lodgement of cells within the affected tissue milieu, in apposition to cells bearing E-selectin (i.e., endothelial cells) and/or L-selectin (i.e., leukocytes), respectively, within the target site. Thus, the spatial distribution and localization of administered cells within the target tissue is modulated by the enforced glycosylation pattern on administered cells.

Particularly, the colonization of a desired cell type at a site of inflammation occurs as a result of the enforced glycosylation pattern on the administered cells, such that the administered cells have augmented binding to E-selectin, thereby promoting the systemic delivery of the desired cells and/or the lodgement of cells when injected directly into the affected site. For example, the enforced glycosylation pattern of E-selectin ligands (e.g., HCELL) is advantageously capable of anchoring directly injected cells within E-selectin-expressing vessels at sites of inflammation, tissue injury, or cancer. Thus, the present methods augment efficiency in the delivery of relevant cells at or to a site of inflammation, tissue injury, or cancer, including, for example, the capacity to deliver tissue-reparative stem cells, to deliver immunomodulatory cells (e.g., mesenchymal stem cells, T-regulatory cells, NK-cells, dendritic cells, etc.), and the capacity to deliver immune effector cells to combat the inciting inflammatory process or cancer (e.g., in the case of infection or malignancy, delivery of pathogen-specific immune effector T cells or cancer-specific cytotoxic T cells or NK cells, respectively); such immunologic cells (regulatory T-cells, NK cells, cytotoxic T-cells, dendritic cells, etc.) may be antigen-pulsed, tumor cell pulsed, virus pulsed, and other means to create antigen specificity. Similarly, the enforced glycosylation pattern of L-selectin ligands (e.g., HCELL) is advantageously capable of anchoring directly injected cells within L-selectin-expressing cells infiltrating sites of inflammation, tissue injury, or cancer.

According to some embodiments, the enforced glycosylation pattern on the cell surface will drive vascular homing of cells to any site where E-selectin is expressed. In various embodiments, the cell population comprises $Le^x$, $sLe^x$, VIM-2, and/or Di-Fuc-$sLe^x$. For example, since CD44 is a ubiquitously expressed cell membrane protein and is displayed on stem/progenitor cell populations of both "adult" and embryonic types, the capacity to modify glycosylation of this protein by ex vivo glycan engineering to create the HCELL (CD44 glycoform) phenotype will drive migration of injected (e.g., intravascularly) (adoptively transferred) cells in vivo to marrow or to any tissue/organ site where E-selectin is expressed. Thus, the modified cells can be used in therapeutic settings to achieve targeted cell migration in a variety of physiologic and pathologic processes, including, for example, bone diseases, immune diseases, infectious diseases, and cancer therapeutics, to name just a few conditions. According to some embodiments, glycans are engineered in distinct patterns on the surface of a cell to drive a desired amount of E-selectin ligand activity. (See, e.g., 108, 109, 110, 111, 112)

It has also been discovered that the disease, disorder, or medical condition having associated inflammation can be treated using the instant methods even in the absence of differentiation of the cell population in the subject. That is, there are trophic effects of administered cells at the site of inflammation without persistent engraftment and/or repopulation of the administered cells, irrespective of the type of tissue involved. These trophic effects include release of cytokines/growth factors that promote revascularization (e.g., VEGF), that promote tissue repair (e.g., TGF-.beta.), that are immunomodulatory (e.g., IL-10), that stimulate growth/proliferation of tissue-resident progenitors (e.g., SCF, LIF, etc) and many other tissue-reparative processes (e.g., mitochondria delivery to cells). In addition, administered cells (e.g., Tregs, MSCs, dendritic cells, etc.) may have potent immunomodulatory properties, including direct suppression of activated lymphocytes (e.g., via expression of PDL-1).

The Present Disclosure Further Includes the Following Enumerated Embodiments

Embodiment 1. A method of selectively enforcing a glycosylation pattern on a cell comprising contacting the cell with a glycosyltransferase, wherein the enforced glycosylation pattern is selected from the group consisting of: (i) $Le^x$(+), $sLe^x$ (+), VIM-2 (−), and Di-Fuc-$sLe^x$ (−); (ii) $Le^x$ (+), $sLe^x$ (+), VIM-2 (−), and Di-Fuc-$sLe^x$ (+); (iii) $sLe^x$(+), $Le^x$(−), VIM-2 (−), and Di-Fuc-$sLe^x$ (+); and (iv) $Le^x$(+), $sLe^x$ (−), VIM-2 (−), and Di-Fuc-$sLe^x$ (−).

Embodiment 2. A cell comprising an enforced glycosylation pattern made by the process of contacting the cell with a glycosyltransferase, wherein the enforced glycosylation pattern is selected from the group consisting of: (i) $Le^x$(+), $sLe^x$ (+), VIM-2 (−), and Di-Fuc-$sLe^x$ (−); (ii) $Le^x$(+), $sLe^x$ (+), VIM-2 (−), and Di-Fuc-$sLe^x$ (+); (iii) $sLe^x$(+), $Le^x$(−), VIM-2 (−), and Di-Fuc-$sLe^x$ (+); and (iv) $Le^x$(+), $sLe^x$ (−), VIM-2 (−), and Di-Fuc-$sLe^x$ (−).

Embodiment 3. A method of selectively tuning a human mesenchymal stem cell (hMSC) to express the following glycosylation pattern, $Le^x$(+), $sLe^x$ (+), VIM-2 (−), and Di-Fuc-$sLe^x$ (−), comprising selecting a Fucosyltransferase IV and contacting the hMSC with the selected enzyme.

Embodiment 4. A method of selectively tuning a human mesenchymal stem cell (hMSC) to express the following glycosylation pattern, $Le^x$(+), $sLe^x$ (+), VIM-2 (−), and Di-Fuc-$sLe^x$ (+), comprising selecting a Fucosyltransferase VI and contacting the hMSC with the selected enzyme.

Embodiment 5. A method of selectively tuning a human mesenchymal stem cell (hMSC) to express the following glycosylation pattern, sLex(+), Lex(−), VIM-2 (−), and Di-Fuc-$sLe^x$ (+), comprising selecting a Fucosyltransferase VII and contacting the hMSC with the selected enzyme.

Embodiment 6. A method of selectively tuning a human mesenchymal stem cell (hMSC) to express the following glycosylation pattern, $Le^x(+)$, $sLe^x$ (−), VIM-2 (−), and Di-Fuc-$sLe^x$ (−), comprising selecting a Fucosyltransferase IX and contacting the hMSC with the selected enzyme.

Embodiment 7. A composition comprising a cell having an enforced glycosylation pattern selected from the group consisting of: (i) $Le^x(+)$, $sLe^x$ (+), VIM-2 (−), and Di-Fuc-$sLe^x$ (−); (ii) $Le^x(+)$, $sLe^x$ (+), VIM-2 (−), and Di-Fuc-$sLe^x$ (+); (iii) sLex(+), Lex(−), VIM-2 (−), and Di-Fuc-$sLe^x$ (+); and (iv) $Le^x(+)$, $sLe^x$ (−), VIM-2 (−), and Di-Fuc-$sLe^x$ (−).

Embodiment 8. A process for custom engineering a fucosylated lactosaminyl glycan comprising: (a) determining a desired glycosylation pattern for a target cell, wherein the glycosylation pattern is selected from the group consisting of: (i) $Le^x(+)$, $sLe^x$ (+), VIM-2 (−), and Di-Fuc-$sLe^x$ (−); (ii) $Le^x(+)$, $sLe^x$ (+), VIM-2 (−), and Di-Fuc-$sLe^x$ (+); (iii) $sLe^x(+)$, Lex(−), VIM-2 (−), and Di-Fuc-$sLe^x$ (+); and (iv) $Le^x(+)$, $sLe^x$ (−), VIM-2 (−), and Di-Fuc-$sLe^x$ (−); (b) selecting a fucosyltransferase capable of producing the desired glycosylation pattern; and (c) contacting the target cell with the selected fucosyltransferase.

Embodiment 9. The method, composition, or process of any one of Embodiments 1-8, wherein the fucoslytransferase is selected from the group consisting of Fucosyltransferase IV, Fucosyltransferase VI, Fucosyltransferase VII, and Fucosyltransferase IX.

Embodiment 10. The method, composition, or process of any one of Embodiments 1-9, wherein contacting the cell with Fucosyltransferase IV results in the enforced glycosylation pattern of (i).

Embodiment 11. The method, composition, or process of any one of Embodiments 1-10, wherein contacting the cell with Fucosyltransferase VI results in the enforced glycosylation pattern of (ii).

Embodiment 12. The method, composition, or process of any one of Embodiments 1-11, wherein contacting the cell with Fucosyltransferase VII results in the enforced glycosylation pattern of (iii).

Embodiment 13. The method, composition, or process of any one of Embodiments 1-12, wherein contacting the cell with Fucosyltransferase IX results in the enforced glycosylation pattern of (iv).

Embodiment 14. The method, composition, or process of any one of Embodiments 1-13, wherein the cell is a stem cell.

Embodiment 15. The method, composition, or process of any one of Embodiments 1-14, wherein the stem cell is a human mesenchymal stem cell (hMSC).

Embodiment 16. The method, composition, or process of any one of Embodiments 1-15, wherein the enforced glycosylation pattern is effective to increase the cell binding to E- and/or L-selectin.

Embodiment 17. The method, composition, or process of any one of Embodiments 1-16, wherein the enforced glycosylation pattern is effective to increase reactivity of the cell to HECA-452 antibody.

Embodiment 18. The method, composition, or process of any one of Embodiments 1-17, wherein the enforced glycosylation pattern is effective to increase reactivity of the cell to one or more of HECA-452 antibody, CSLEX1 antibody, HI98 antibody, and FH6 antibody.

Embodiment 19. A method of treating tissue injury of a subject comprising the steps of administering to the subject a cell according to any one of Embodiments 1-18.

Embodiment 20. A method of delivering a cell to a site of inflammation in a subject comprising the step of administering the cell according to any one of Embodiments 1-19.

Embodiment 21. A method of delivering a cell to the bone marrow of a subject comprising the step of administering the cell of any one of Embodiments 1-20.

Embodiment 22. A method of delivering a cell to the skin of a subject comprising the step of administering the cell of any one of Embodiments 1-21.

Embodiment 23. The method, composition, or process of any one of Embodiments 1-22, wherein the cell binds to E- and/or L-selectin.

Embodiment 24. The method, composition, or process of any one of Embodiments 1-23, wherein the Fucosyltransferase IV is the short form.

EXAMPLES

The following are examples of methods and compositions of the invention. It is understood that various other embodiments may be practiced, given the general description provided above.

Example 1

Figure 2A:
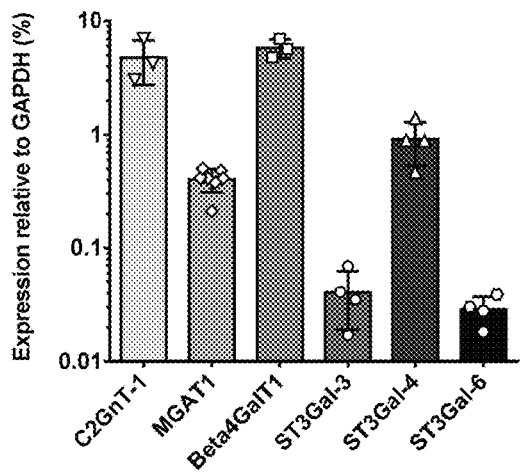
FIG. 2A to FIG. 2E depicts data showing hMSCs express lactosaminyl and sialylated lactosaminyl glycans, but do not express the fucosylated lactosamines (unsialylated or sialylated, respectively) Lewis X ($Le^x$) or sialyl Lewis X ($sLe^x$).
Figure 2B:
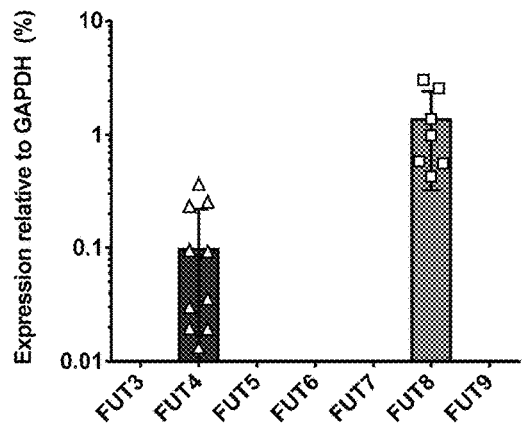

Human MSCs do not Express $sLe^x$ or $Le^x$ Determinants but Construct both Sialylated and "Neutral" (Unsialylated) Type 2 Lactosamines To elucidate the native lactosaminyl glycan "signature" of human MSCs (hMSCs), we performed gene expression studies of glycosyltransferases, in concert with flow cytometry of cell surface lactosaminyl glycan display using a combination of antibody and lectin probes, in multiple hMSC cultures derived from marrow obtained from healthy donors. We first assessed the gene expression levels in hMSCs of glycosyltransferases required for construction of Type 2 lactosaminyl glycans: (i) The enzymes required for initiating O- and N-glycosylations that display terminal lactosamines, respectively, the O-glycan "core 2" branch-initiating enzyme (C2GnT-1) and the "complex type" N-glycan-initiating enzyme (MGAT1); (ii) The galactosyltransferase that predominates in Type 2 lactosamine synthesis (β4GalT1); (iii) The three human α(2,3) sialyltransferases (STs) that are capable of terminally sialylating a Type 2 lactosamine (ST3Gal-3, -4 and -6) (FIG. 2A); and (iv) The six members of the human α(1,3)-FT family (FT3, 4, 5, 6, 7, and 9) that can fucosylate N-acetylglucosamine within terminal Type 2 lactosaminyl glycans (FIG. 2B). In addition, as an internal control for evaluation of fucosyltransferase gene expression by qRT-PCR, we measured transcript levels for the ubiquitously expressed enzyme FT-8, which places fucose in α(1,6)-linkage on the innermost (core) GlcNAc of N-glycans. We observed that hMSCs expressed appreciable transcript levels of all glycosyltransferases tested except for the α(1,3)-FUTs. Notably, FUT4 transcripts were detectable but at extremely low levels, while transcripts for the remaining α(1,3)-FUTs (i.e. FUT3, 5, 6, 7, and 9) were absent (FIG. 2B). However, hMSCs are not uniformly deficient in fucosyltransferases, as prominent transcript levels for FUT8 were observed (FIG. 2B). Collectively, these data indicate that hMSCs express the requisite enzymes to create lactosaminyl and sialylated lactosaminyl glycans on both N-glycans and O-glycans, but lack α(1,3)-FTs required for the synthesis of $Le^x$ and $sLe^x$, and the related sialofucosylated structures VIM-2 and difucosyl $sLe^x$. These data therefore supported the notion that this clinically-relevant, human cell type would serve as a fitting model system to assess the in vivo substrate specificities of the human α(1,3)-FT isoenzymes.

Figure 2C:
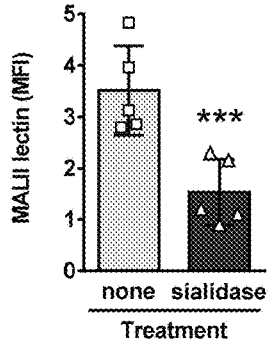
Figure 2D:
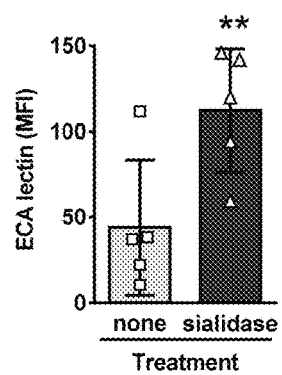
Figure 2E:
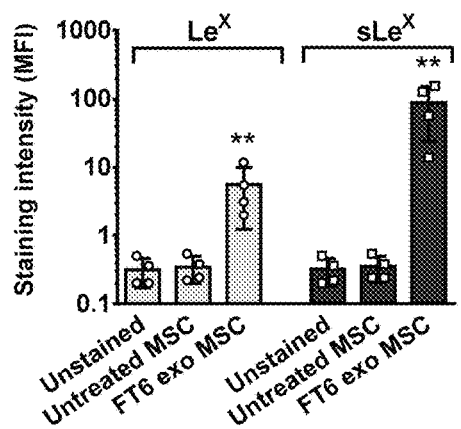
Figure 3A:
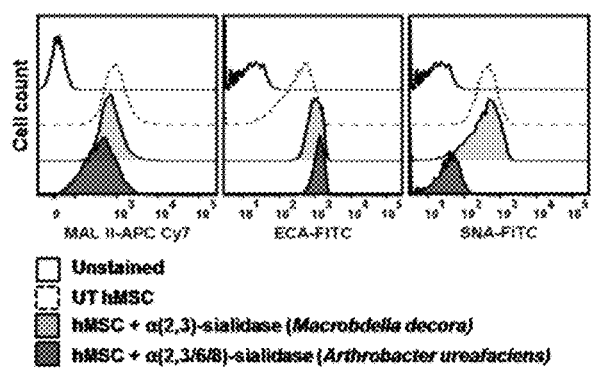
FIG. 3A and FIG. 3B depict data of representative flow cytometry histograms of hMSCs stained with lectins and glycan-specific antibodies.
Figure 3B:
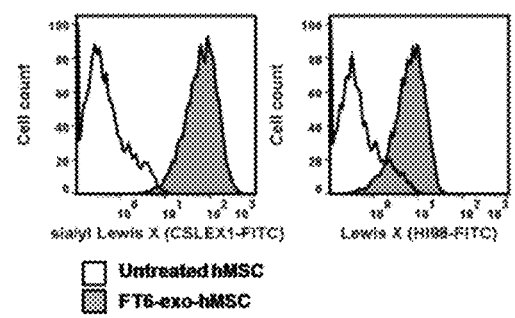

To evaluate the native cell surface expression of both unsialylated and sialylated terminal Type 2 lactosaminyl glycans, two complementary approaches were undertaken: (i) Lectin staining; and (ii) Analysis of products of FT6-mediated exofucosylation. The lectin ECA binds to unsialylated Type 2 lactosamines, whereas the lectin MALII detects sialic acid α(2,3)-linked to galactose (41) (and is also reactive with certain sulfated glycans (41,42)). There was significant baseline binding with both ECA and MALII lectin probes. In initial studies, we observed that treatment with the broad-specificity sialidase from *Arthrobacter ureafaciens* yielded decreased MALII binding and increased ECA binding (FIG. 2C and FIG. 2D). To further assess the presence of α(2,3)-sialylated type 2 lactosamines on hMSCs, we treated these cells with an α(2,3)-specific sialidase (sialidase from *Macrobdella decora* (43)), and evaluated binding of the lectins MALII, ECA, and SNA (a lectin that binds specifically to α(2,6)-linked sialic acid). Upon α(2,3)-sialidase treatment, MAUI lectin binding was reduced, ECA lectin binding was increased sharply, and SNA lectin binding remained unchanged (FIG. 3A). Collectively, these results provided evidence that α(2,3)-sialylated type 2 lactosamines are present on hMSC surface. As predicted by results of α(1,3)-FUT transcript analysis, flow cytometry of cell surface glycans revealed that, natively, hMSCs do not express sLe$^x$ (measured by mAb CSLEX1) or Le$^x$ (measured by mAb HI98) determinants (FIG. 2E, untreated, FIG. 3B). Upon exogenous fucosylation of these cells with FT6 enzyme and GDP fucose, production of both Le$^x$ and sLe$^x$ was observed (FIG. 2E, FT6 exo MSC, FIG. 3B). Altogether, these results confirmed that although hMSCs lack expression of α(1,3)-fucosylated lactosaminyl glycans, both unsialylated and sialylated terminal type 2 lactosamine acceptors are present on the cell surface that can be converted to Le$^x$ and sLe$^x$, respectively, by exofucosylation with a pertinent α(1,3)-FT.

Example 2

Construction of modRNA Encoding the Six Human α(1,3)-Fucosyltransferases

To analyze the enzymatic product specificities of the human α(1,3)-FTs in the context of human cells, we utilized modified-mRNA (modRNA), which is non-permanent and non-genome integrative, and can be readily transfected directly into hMSCs (38). Once inside the cell, the modRNA is recognized by the cell's endogenous translational machinery, and protein synthesis ensues. The resulting protein then undergoes normal post-translational folding and processing, and subsequently becomes localized to its normal position within the cell. We synthesized modRNAs encoding the six human α(1,3)-fucosyltransferases (i.e., creating modRNAs FUT3,4,5,6,7, and 9), transfected them individually into hMSCs, and probed for the presence of surface Le$^x$ and/or sLe$^x$ by flow cytometry. In initial experiments, the α(1,3)-FUT modRNAs generated appreciable levels of Le$^x$ and/or sLe$^x$ with the exception of FUT4, which displayed little or no activity; despite confirming sequence integrity as reported in GenBank (accession number: BC136374), and controlling for modRNA integrity and transfection efficiency, we consistently observed no evidence of fucosylated products using multiple independent FUT4 modRNA preparations.

FUT4 ModRNA Transfection Provides Direct Evidence that Only "Short" FUT4 RNA Creates Functional FT4

Figure 4A:
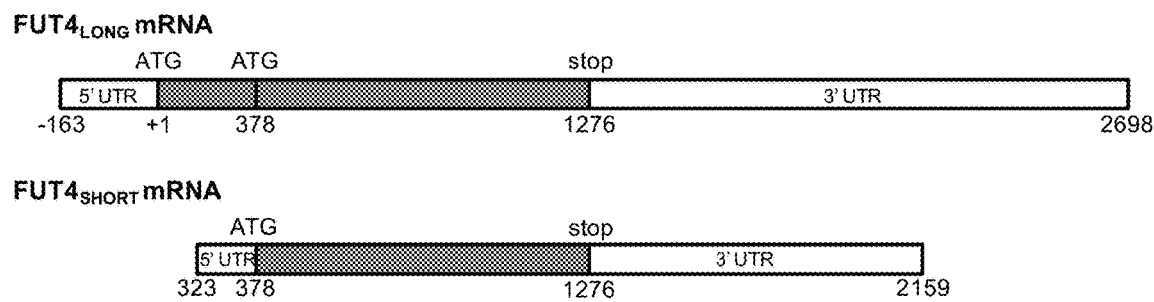
FIG. 4A to FIG. 4C depicts data showing that modified mRNA encoding the short isoform of FUT4 ($FUT4_{short}$) enforces CD15 expression in transfected hMSCs, while the long isoform of FUT4 ($FUT4_{long}$) has no effect.
Figure 4B:
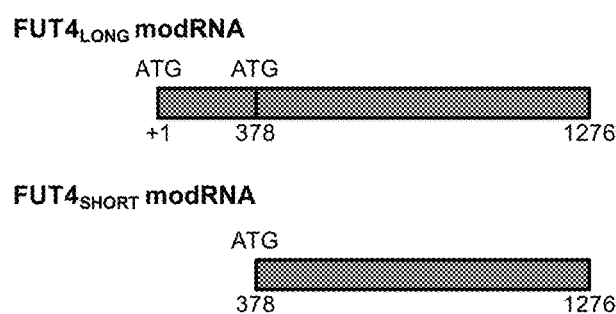
Figure 4C:
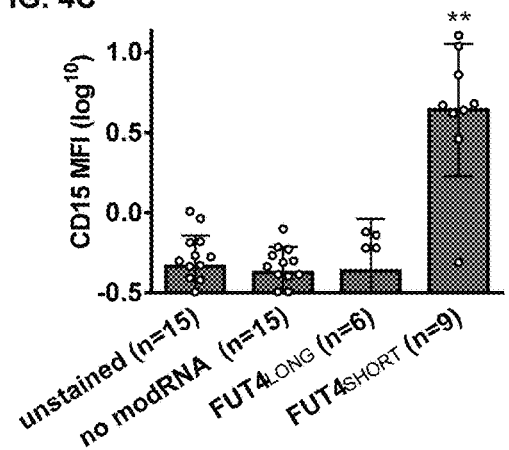

The original report of cloning of human FT4 indicated that two transcript variants of FUT4 (originally named "ELAM-1 ligand fucosyltransferase" (ELFT)) exist: ELFT (indicated here as "FUT4$_{short}$", which encodes a 405 amino acid protein) and a putative longer isoform (ELFT-L; indicated here as "FUT4$_{long}$") (25). Though the molecular basis of these two transcript sizes has not been defined (i.e., alternative splicing of the primary longer transcript or an alternative transcription initiation site embedded within the gene sequence 5' to the "short" ELFT gene product), it is recognized that, compared to ELFT, ELFT-L contains an extended 3' UTR, a different 5' UTR, as well as an alternative ATG start site yielding a coding sequence corresponding to 530 amino acids (FIG. 4A to FIG. 4C). However, the putative ATG start site for ELFT-L is not embedded amongst any of the nucleotides typical of the consensus Kozak sequence, casting doubt on the translational capacity of this longer RNA transcript (25). Despite this fact, genome databases (e.g., GenBank accession number BC136374), have consistently annotated ELFT-L as the authentic FUT4 mRNA coding sequence, and thus this sequence was chosen for all initial experiments. However, as noted above, hMSC transfection with FUT4$_{long}$-modRNA did not yield fucosylated products on the cell surface, and we thus tested whether transfection with FUT4$_{short}$-modRNA could yield enzymatic function. To this end, we performed transfection in hMSCs using FUT4$_{short}$-modRNA versus FUT4$_{long}$-modRNA, and, as can be seen in FIG. 4, FUT4$_{short}$-modRNA produced robust levels of cell surface Le$^x$, while FUT4$_{long}$-modRNA did not produce Le$^x$.

Figure 5A:
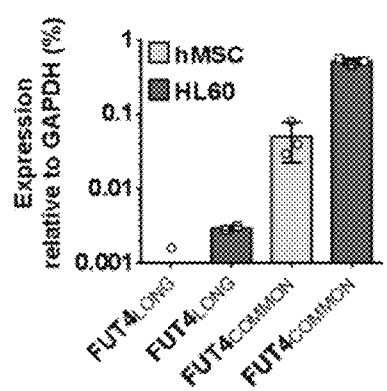
FIG. 5A and FIG. 5B depict data showing that MSCs natively express low levels of $FUT4_{SHORT}$ transcript while $FUT4_{LONG}$ transcript is absent.
Figure 5B:
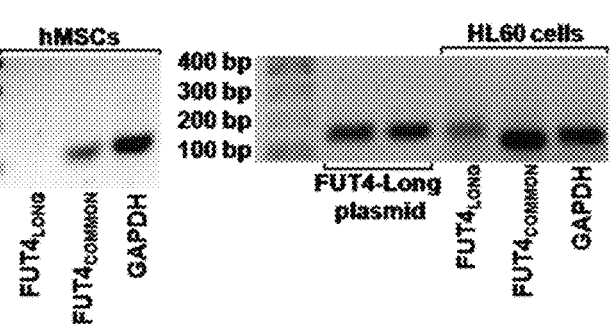
Figure 6A:
FIG. 6A to FIG. 6D depicts a comparative analysis of human α(1,3)-FT product specificities by modified mRNA transfection of hMSCs, measured by flow cytometry.
Figure 6B:
Figure 6C:
Figure 6D:

Since the qRT-PCR primer sets used initially to probe FUT4 transcripts in hMSCs were embedded within the "common" FUT4 coding sequence (i.e., amplifying a 123 bp fragment within the coding region common to both FUT4$_{long}$ and FUT4$_{short}$), we analyzed for FUT4$_{long}$ (i.e., ELFT-L) transcripts using a 5' primer that detects a 150 bp amplicon upstream of (and not overlapping with) the core FUT4 sequence. Plasmid containing FUT4$_{long}$ cDNA was used as positive control, as was RNA isolated from the human promyelocytic cell line HL60 (which is known to express both FUT4 transcripts) (25,44). qRT-PCR of HL60 cells confirmed the presence of FUT4$_{long}$ transcript and the "common" FUT4 transcript (FIG. 5A), with amplicon sizes verified by gel electrophoresis of the PCR products (FIG. 5B). In hMSCs, low transcript level (0.05% of GAPDH) was detected with FUT4$_{common}$-primers, whereas no product was detected with FUT4$_{long}$-primers (FIG. 5A). These findings indicate that only the short form of FUT4 is expressed in hMSCs, although neither Le$^X$ or sLe$^X$ product was detectable on the cell surface by flow cytometry.

modRNA-Driven Expression of α(1,3) FTs Reveal Unique Product Specificities

We transfected hMSCs derived from multiple marrow donors with each of the α(1,3) FUTs (n=15 donors, for FUT 3, 5, 6, 7, 9; n=9 donors, for FUT4$_{short}$), and 48 hours later measured the resulting fucosylated lactosaminyl glycans using monoclonal antibodies recognizing the terminally α(1,3)-fucosylated lactosaminyl glycans Le$^X$ and sLe$^X$, and the related internally (penultimate) α(1,3)-fucosylated lactosaminyl glycans VIM-2, as well as the determinant containing both terminal and penultimate α(1,3)-fucose modifications known as difucosyl sLe$^X$ (FIG. 6, FIG. 7). All six of the α(1,3)-FTs tested were able to fucosylate Type 2 lactosamines to create Le$^X$ and/or sLe$^X$, although clearly distinct enzymatic specificities were observed (FIG. 6). With the exception of FT9, all other α(1,3)-FTs were able to terminally fucosylate a sialylated Type 2 lactosamine, with FT6 and FT7 having the highest potency, FT3 and FT5 having moderate capability, and FT4 showing very limited capacity to create sLe$^X$ (FIG. 6A, FIG. 7A). Conversely, FT9 and FT4 were most potent in terminally fucosylating an unsialylated Type 2 lactosamine to create Le$^X$, FT3, FT5, and FT6 had moderate ability, and FT7 did not create Le$^X$ (FIG. 6B, FIG. 7B). Notably, FT3 and FT5 were the only FTs that could internally fucosylate a sialylated polylactosamine, creating the VIM-2 glycan determinant (FIG. 6C, FIG. 7C). FT3, FT5, FT6, and FT7 were all capable of fucosylating both the penultimate and terminal lactosamines of a sialylated poly-lactosamine, thereby creating the "difucosyl sLe$^X$" structure (FIG. 6D, FIG. 7D). FT4 and FT9 do not create any detectable difucosyl sLe$^X$, but, in contrast to the prior findings, FT6 did so with the highest potency of all the α(1,3)-FTs.

The results of flow cytometry studies are summarized in the table in FIG. 8A. Importantly, we observed strict consistency in this expression profile across all hMSC cultures, indicating that this panel identifies a "lactosaminyl glycosignature" of this human cell type. Surprisingly, our findings identified several divergences between our dataset and prior findings: the VIM-2 glycan is not created by either FT4, FT6 or FT9; there was modest but consistently detectable production of sLe$^X$ following FUT4$_{short}$-modRNA transfection; and, though FT6 does not create VIM-2, it creates significant amounts of difucosyl sLe$^X$.

Glycomic Analysis of modRNA-Transfected hMSCs

Flow cytometry analysis using monoclonal antibodies provides very useful information regarding the relative amounts of fucosylated lactosaminyl glycan determinants created by α(1,3)-FTs but is not able to distinguish their display on different scaffolds, such as O-linked versus N-linked glycans of protein, or glycosphingolipids (GSLs). However, identification of these various structures can be achieved by glycan fractionation followed by mass spectrometry (MS), and, furthermore, ion trap sequential MS (MS$^n$) glycan analysis can provide detailed assessment of the component monosaccharide composition; this information complements and cross-validates the molecular identification of the relevant lactosaminyl glycan determinants detected by flow cytometry. To perform MS, cell lysates were prepared from different hMSC cultures derived from multiple donors at 48 hours after transfection with individual FUT modRNAs. O-glycans, N-glycans, and glycosphingolipid (GSL)-glycans were sequentially released from lysates and isolated. These fractions were then interrogated by various mass spectrometry techniques to determine the presence or absence of specific fucosylated structures.

Figure 9A:
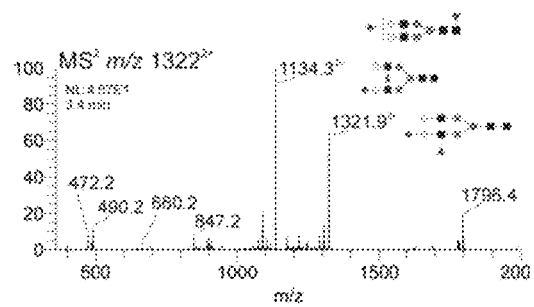
FIG. 9A to FIG. 9F shows a partial MS$^n$ data set for one replicate of a FUT6-transfected sample.
Figure 9B:
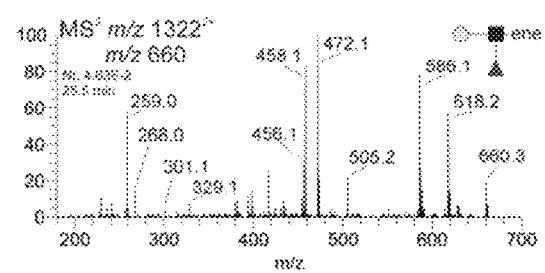
Figure 9C:
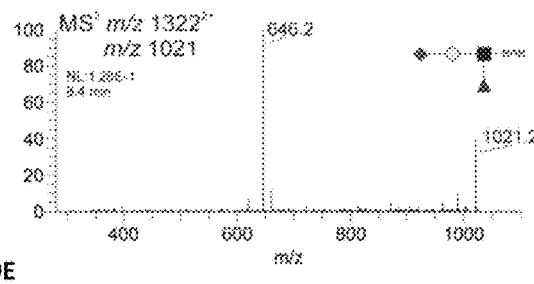
Figure 9D:
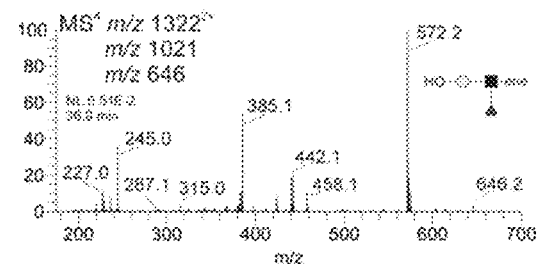
Figure 9E:
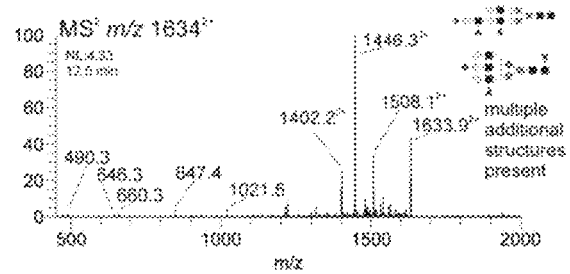
Figure 9F:
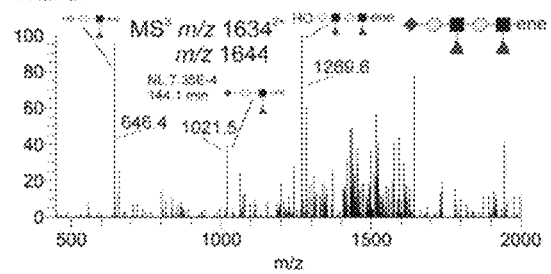
Figure 10A:
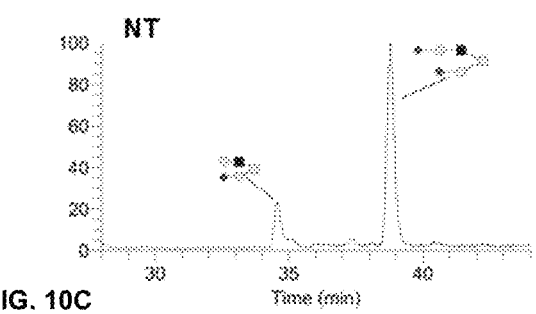
FIG. 10A to FIG. 10G shows selected overlaid extracted-ion chromatograms of the indicated structures. Reduced and permethylated O-glycan samples were separated by reversed-phase LC-MS. Intact mass was used to identify compositions; detailed structures were obtained by direct infusion MS$^n$. Peak areas of the relevant structures were used for relative quantitation.
Figure 10B:
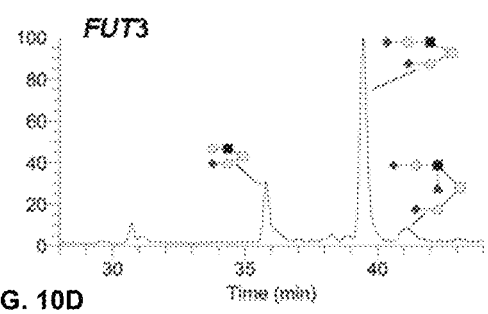
Figure 10C:
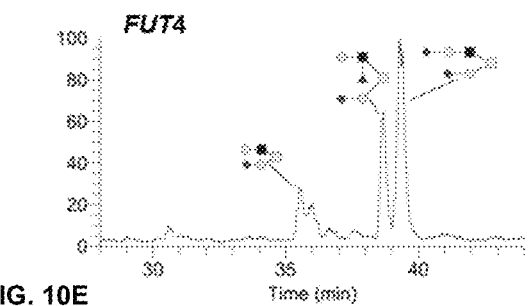
Figure 10D:
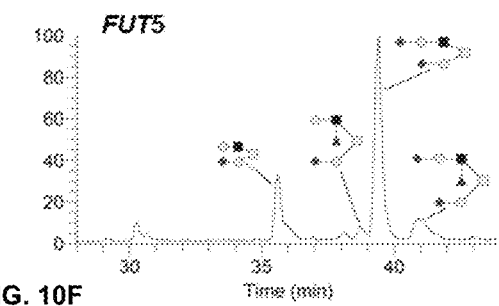
Figure 10E:
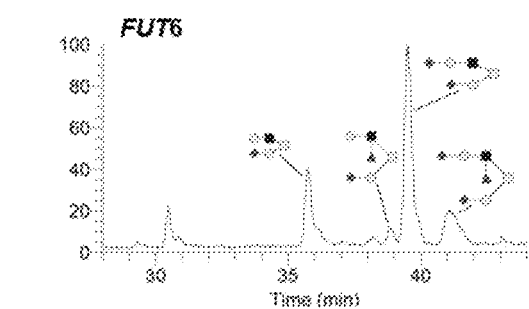
Figure 10F:
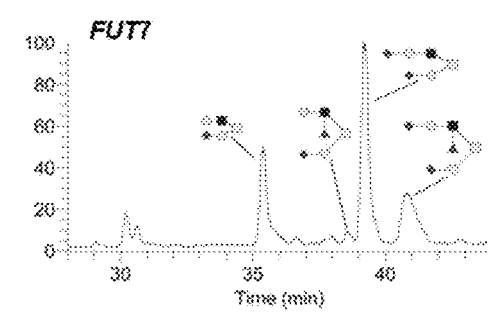
Figure 10G:
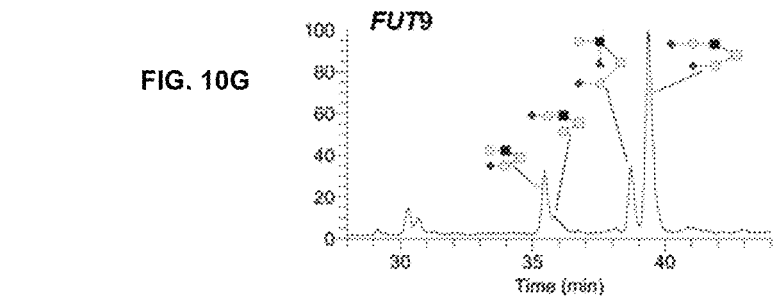
Figure 11A:
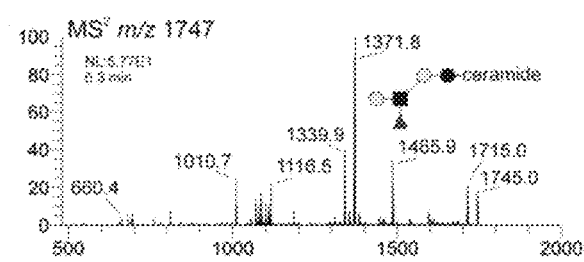
FIG. 11A to FIG. 11E shows a partial MS$^n$ data set for the GSL fraction of one replicate of a FUT6 transfected sample.
Figure 11B:
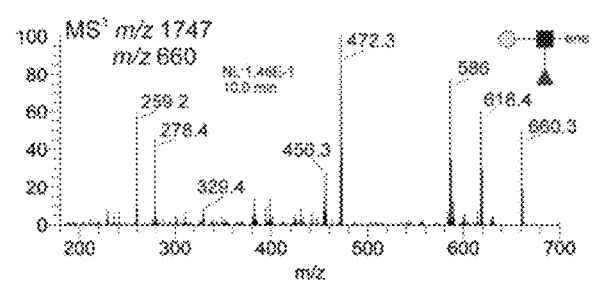
Figure 11C:
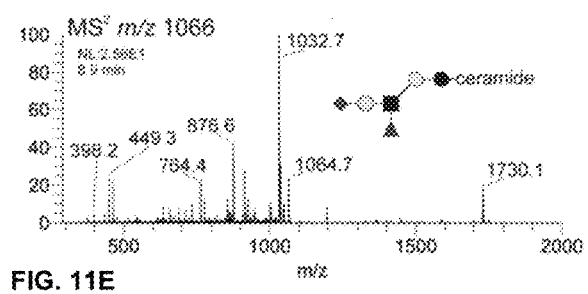
Figure 11D:
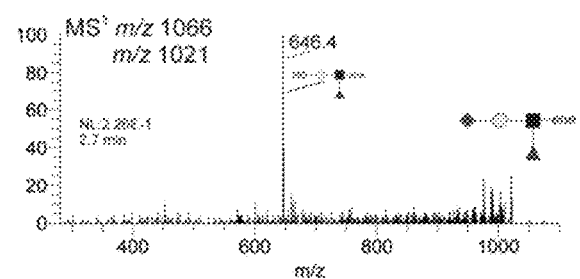
Figure 11E:
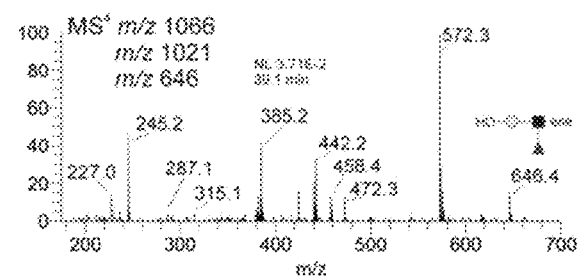
Figure 12A:
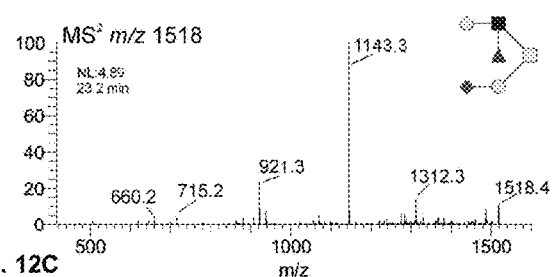
FIG. 12A to FIG. 12E shows a partial MS$^n$ data set for representative O-glycans from a FUT6-transfected hMSC sample.
Figure 12B:
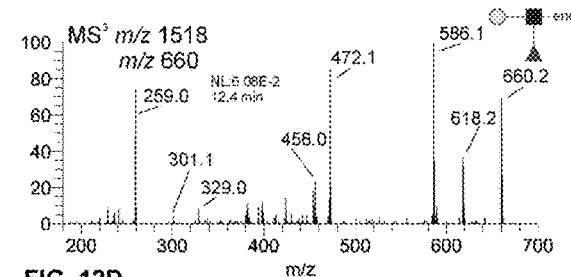
Figure 12C:
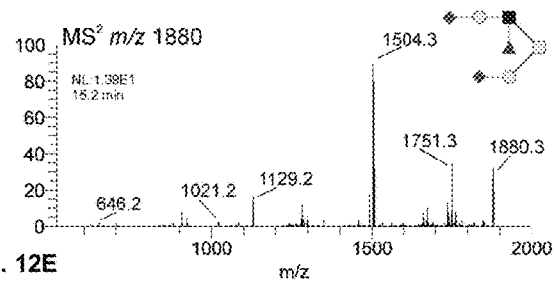
Figure 12D:
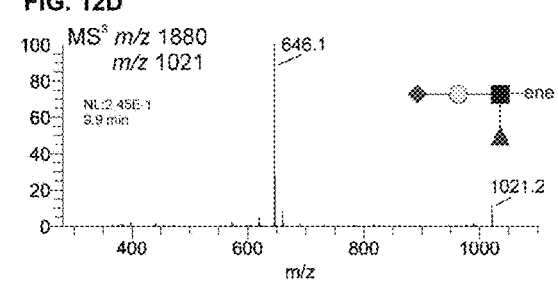
Figure 12E:
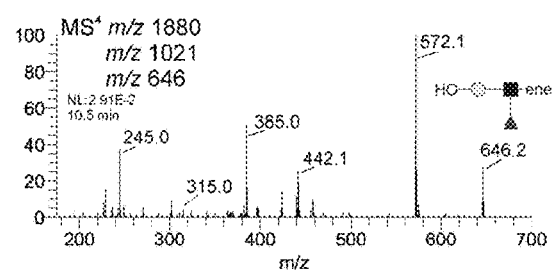

In order to assess the synthesis of Le$^X$/sLe$^X$ formation in N-glycans, detailed interrogation is required due to the presence of multiple isomeric structures for any sialofucosylated composition. We chose to focus on an N-glycan composition found in all samples, a composition with an m/z 1322 that is doubly-charged, and has the composition (NeuAc$_1$Hex$_2$HexNAc$_2$dHex$_1$+Man$_3$GlcNAc$_2$), corresponding to a biantennary, monosialylated, monofucosylated structure (FIG. 9). For this composition, the fucose ("dHex") can be positioned either on the core GlcNAc (i.e. the α(1,6)-fucosylation catalyzed by FT8), on the sialylated LacNAc antenna (i.e. sLe$^X$), or on an unsialylated LacNAc antenna (i.e. Le$^X$ or H type 2 ("H2", the blood group O antigen on a Type 2 lactosamine)) (FIG. 9), and, thus, this structure could contain one or more of the following isomeric possibilities: core fucosylation, the H2 structure, Le$^X$, and sLe$^X$. Using ion-trap MS$^n$ to perform detailed structural analysis, we could identify which of these isomers represent this composition. Specifically, the fucosylated fragment ions of interest include m/z 490 (core GlcNAc fucosylation), m/z 660 (terminal fucosylated LacNAc, i.e., Le$^X$ and/or H2), m/z 1021 (sialylated Le$^X$ tetrasaccharide), and 646 (a desialylated sLe$^X$, generating an Le$^X$ fragment) (FIG. 9). In addition, in an effort to assess for the presence of difucosyl sLe$^X$, we selected the m/z 1634$^{2+}$ ion; this composition is representative of three lactosamine units, and one sialic acid, three mannose, two GlcNAc and two fucose molecules. This composition could be contained within both triantennary and biantennary structures, with the former containing a LacNAc on each antenna and the latter containing one antenna containing a single LacNAc and the other containing two contiguous LacNAc units (a "diLacNAc" motif). By selecting the putative sLe$^X$-Le$^X$ heptasaccharide fragment (difucosyl sLe$^X$) and then obtaining an MS$^3$ spectrum, we could then assess for the presence of this motif (FIG. 9F). The results indicate that core α(1,6)-fucosylation is uniformly detectable in hMSCs, whereas sLe$^X$ is not detectable among native hMSCs and its creation is unique to specific fucosyltransferases (FIG. 8B). By MS analysis, traces of Le$^X$ were observed only on N-glycans of native hMSCs which may reflect the endogenous low-level expression of FUT4$_{short}$ transcripts, and, notably, this modest level of Le$^X$ expression was not detectable by flow cytometry. In contrast, though VIM-2 determinants were readily identified by flow cytometry in FUT3 and FUT5 transfectants, the MS$^n$ fragmentation profiles representative of this structure could not be definitively detected on any glycoconjugate sample from any transfectant. The incongruity between flow cytometry and MS detection of VIM-2 expression is explained by the fact that MS identification of this structure requires isolation of the hexasaccharide fragment with subsequent dissociation, and the lability of linkages in this structure, coupled with its apparent low abundance and the presence of other isobaric ions in these samples, prevented a confident MS assignment.

Since O-glycan fractions generally have fewer sample components than N-glycans and also are generally small-sized glycans, their greater polarity relative to permethylated N-glycans or glycosphingolipids makes reversed-phase liquid chromatography-mass spectrometry (LC-MS) a useful approach to obtain relative quantitative data. By selecting relevant mass ranges, extracted ion chromatograms can be used to provide data informing both glycan structure and relative quantity. Since VIM-2 and difucosyl sLe$^X$ were not detected on O-glycans by direct infusion MS analysis, using LC-MS we focused on ions corresponding to simple branched O-glycan structures containing Le$^X$ or sLe$^X$, or the corresponding unfucosylated 'acceptor' structures (FIG. 10). By comparing the relative amounts of the product and acceptor, an approximate percent created could be estimated, enabling a semi-quantitative measurement of Le$^X$ and sLe$^X$ creation on O-glycans (FIG. 8B, FIG. 8C). When Le$^X$ and sLe$^X$ creation on O-glycans was thus calculated, and compared to the flow cytometry data measured from the same samples, the data were strikingly similar (FIG. 8C). Besides cross-validating the specificity, sensitivity, and qualitative and quantitative utility of both approaches for detection of Le$^X$ and sLe$^X$, the close correlation between results from flow cytometry and MS analysis of O-glycans indicates that, for each transfectant, there was no preferential skewing of terminal fucosylation away from O-glycan acceptors. However, a major difference is found in expression of difucosyl sLe$^X$, which is clearly measurable by flow cytometry but MS indicates presence solely on N-glycans. Importantly, FT6 and FT7 can each construct difucosyl sLe$^x$ but not VIM-2; thus, for creation of difucosyl sLe$^x$, it is most likely that FTs 3, 5, 6, and 7 first fucosylate the terminal GlcNAc (thereby creating sLe$^x$), followed by fucosylation of the internal GlcNAc, preferentially on N-glycans.

For MS analysis of glycosphingolipids, two clusters of peaks were chosen for detailed analysis: m/z 1747, which would contain the fucosyltetraosylceramides (including Le$^x$), and m/z 1066, which would contain the doubly-charged sialofucosylated tetraosylceramide (including sLe$^x$) (FIG. 11). MS$^n$ was then performed on each of these m/z ranges to identify the specific fucosylated glycans present (if any) for each FUT modRNA transfectant. As summarized in the table in FIG. 8B, Le$^x$ was detected in FUT4-, FUT6-, and FUT9-transfected hMSCs, which corresponds to the three fucosyltransferases that resulted in the highest levels of Le$^x$ by flow cytometry. Notably, despite the ability to produce Le$^x$ and sLe$^x$ on glycoproteins, FUT5-transfectants did not make any detectable Le$^x$ or sLe$^x$ on GSLs, and FUT3-transfectants made only a trace of Le$^x$ on GSLs, suggesting a unique substrate specificity and/or subcellular localization pattern of FT3 and FT5 compared to other FTs. Importantly, sLe$^x$ bearing GSLs were detected prominently only in FUT6-transfected hMSCs, indicating that FT6 is either specialized to create sLe$^x$ on GSLs or has unique accessibility to GSLs inside the Golgi.

Collectively, the MS results indicate that, with exception of trace amounts of Le$^x$ on N-glycans, all other types of terminally-fucosylated LacNAc are not natively expressed on hMSC glycoconjugates. Moreover, both unsialylated and sialylated acceptors are natively distributed among N-glycans, O-glycans and GSLs in hMSCs. Notably, hMSCs exclusively possess type 2 lactosamines (Galβ(1,4)-GlcNAc), as empirical MS$^n$ analysis of LacNAcs showed no evidence of type 1 (Galβ(1,3)-GlcNAc) structures. Moreover, we assessed production of sLe$^a$ among the various the hMSC-FUT transfectants by measuring binding of antibody CA19-9. In sharp contrast to the marked increases observed in HI98-reactivity (Le$^x$) and CSLEX1-reactivity (sLe$^x$), the FUT transfectants (particularly as might be expected from the specificities of FT3 and FT5 for Type 1 lactosamine acceptors) did not yield significant CA-19-9 reactivity (sLe$^a$), thus indicating paucity of type 1 lactosamine acceptors in hMSCs.

Example 3

Discussion

In order to understand cellular glycobiology, it is imperative to elucidate the molecular effectors of glycan biosynthesis, the glycosyltransferases. However, elucidating the authentic drivers programming assembly of a particular glycan moiety of interest is challenging because of the following reasons: (i) In contrast to nucleic acids and proteins, glycan construction is not template-driven, it is directed by the sequential action(s) of glycosyltransferases that modify relevant acceptors in a stereospecific fashion; (ii) Glycosyltransferase isoenzymes typically display functional redundancy (i.e., glycosyltransferases commonly create more than one glycan product, and the same glycan structure may be generated by many glycosyltransferases); and, (iii) Glycosyltransferase expression patterns vary in a species-specific and cell-specific fashion. Thus, to determine whether a certain glycosyltransferase can mediate construction of a given glycan, the relevant enzyme property can be analyzed using ex vivo or in vivo systems. However, because ex vivo studies of glycosyltransferases provide insights only on what these enzymes are capable of producing under the defined reaction conditions utilized, it is imperative to undertake studies in living cells in order to reveal their true biologic activity.

To date, our understanding of the product specificities of human α(1,3)-FTs is largely based on ex vivo studies. Such studies employed purified or recombinant α(1,3)-FTs, or extracts of cells expressing these enzymes, to catalyze fucose addition in cell-free reactions targeting synthetic oligosaccharide substrates presented on artificial reaction surfaces, each present at supraphysiologic concentrations. These studies also typically utilized extremely high levels of manganese (Mn) as a co-factor (i.e., as high as 40 mM, whereas, human physiologic Mn levels are <20 nM), raising fundamental questions about the relevance of these findings to native human cell biology (45). Thus, although such experimental systems can define the catalytic properties of an isolated enzyme, it cannot be assumed that the data derived therefrom can be extrapolated to cell biology. However, prior studies investigating the in vivo glycobiology of human α(1,3)-FTs utilized a wide variety of immortalized mammalian cell lines (predominantly non-human, e.g., CHO, COS, and BHK cells) as hosts for human α(1,3)-FUT transfection(s), and evaluated product profiles by flow cytometry of the cell surface. These diverse cell line-based studies provided broad insights that could not accurately predict the α(1,3)-FT product specificities within human cells. Thus, the non-physiological systems employed in prior in vitro studies and the studies involving a wide range of cell/animal models have raised questions regarding the translatability of these findings to human cell biology, especially in the context of primary human cells.

In this study, we evaluated the impact of FT3, FT4, FT5, FT6, FT7 and FT9 on expression of Le$^x$ and sLe$^x$ moieties, as well as the structurally related VIM-2 and difucosyl sLe$^x$ determinants, on both protein-based and lipid-based glycoconjugates in cultures of hMSCs. Besides these six α(1,3)-FTs, two other α(1,3)-FTs, known as FT10 and FT11, have been identified. These enzymes were not evaluated as they principally modify GlcNAc only within the chitobiose core of N-glycans (46) (a modification not typical of mammalian cells). Though a recent study in FT9-knock-out mice has suggested a possible role for FT10 in creation of Le$^x$ on a uniquely restricted set of N-glycan acceptors found only in mouse neural progenitor cells, a contributory role for FT4 was not formally excluded in that model system as FT4/9 double knock-out mice were not studied (47).

We employed transfection of modRNA encoding the relevant α(1,3)-FT transcripts to enable assessment of the relative 'in-Golgi' capacity of these isoenzymes to program expression of α(1,3)-fucosylated terminal lactosaminyl glycans. FT4 and FT9 in hMSCs are most potent at fucosylating unsialylated Type 2 lactosamines, with FT6 demonstrating moderate capability, FT3 and FT5 showing weak ability, and FT7 having little to no ability. We observed key differences from historical data regarding the capacity of the various α(1,3)-FTs to produce sLe$^x$ and, also, VIM-2 and difucosyl sLe$^x$. Whereas prior studies using the human prostate cancer cell line PC-3 (48) and using Chinese Hamster Ovary (CHO) cell lines (49,50) each indicated that transfection of human FUT4 yields readily detectable levels of sLe$^x$, we observed very limited production of sLe$^x$ by FT4 in hMSCs. In terms of VIM-2 expression, though MS was unable to resolve this structure within the various hMSC transfectants, flow cytometry analysis using anti-VIM-2 mAb clearly indicated that FT3 and FT5 are the only human α(1,3)-FTs that construct this glycan determinant on hMSCs. Again, key differences exist between our results and those of prior cell line-based studies indicating that VIM-2 could be created in CHO cells by FUT4 (24) and by FUT6 (35) transfection, in Jurkat cells (a human lymphoblastic cell line) by FUT4 transfection (51), and in, Namalwa cells (a human lymphoma cell line) following FUT9 transfection (52). Other cell line studies have also indicated that human FT9 can create the VIM-2 determinant on CHO Lec29 cells (53) and HEK293T cells (a human embryonic kidney line) (54), with commensurate induction of E-selectin binding in each (53, 54).

Though FT3 and FT5 were the only enzymes that created VIM-2 in hMSCs, transfection of FUT3, FUT5, FUT6, and FUT7 resulted in cell surface expression of difucosyl sLe$^X$. The finding that difucosyl sLe$^X$ is created in FUT6 and FUT7 transfectants in absence of measurable VIM-2 production suggests that these enzymes modify a sialylated di-LacNAc by first fucosylating the terminal GlcNAc to create an sLe$^X$ structure, then act to convert this structure to difucosyl sLe$^X$ via the addition of a fucose to the penultimate GlcNAc. In other words, these enzymes do not appear to make an intermediate VIM-2 structure, because they have dominant preference for installing a fucose at the terminal GlcNAc. FT3 and FT5 are the only enzymes that can create VIM-2 in hMSCs, and, importantly, appear to have a relatively balanced production of both VIM-2 and sLe$^X$ determinants.

Without being limited by theory, our novel findings can be explained by Golgi dynamics, including factors such as glycosyltransferase localization within specific Golgi microdomains (55) and/or cell-specific variation(s) in Golgi topography that impact glycan formation. Additionally, the accessibility of acceptor glycans within such microdomains, and intra-Golgi dynamics of competing glycosyltransferases and of glycosidases that can modify the same glycan acceptor, could alone and in combination amend the product profile(s) for any given glycosyltransferase within a given cell. In addition to such variations in Golgi dynamics, it is important to consider how phylogenetic disparities impact our understanding of the glycobiology of the α(1,3)-FTs. In this regard, an early study of Fut7 KO mice identified this α(1,3)-FT as key to creation of sLe$^X$ displayed on selectin ligands, emphasizing its role in regulation of leukocyte homing (56). Subsequently, it was determined that FT4 also had a role in this process, since Fut4/Fut7 double knockout mice yielded more severe leukocyte homing deficits (57-59). Importantly, while FT4, FT7 and FT9 are expressed in both rodents and primates, three of the six human α(1,3)-FUTs (FUT3, FUT5 and FUT6) arose from a (relatively) recent gene duplication event in primates and are not present in the rodent genome (60). Our study shows that FT3, FT5, and FT6, the members of the human α(1,3)-FUT gene family without functional homologs in mice, can each produce all three forms of terminally fucosylated lactosamines: Le$^X$, sLe$^X$, and difucosyl sLe$^X$. Among these "primate FTs", the FT3 and FT5 isoenzymes display the broadest product profiles as they can also generate the internally fucosylated VIM-2 epitope. In contrast, FTs 4, 7, and 9 exhibit the most restricted product specificities. Taken together, the stark contrast in α(1,3)-FT repertoire between human and murine systems emphasizes the importance of undertaking studies in human cells using human glycosyltransferases in order to appropriately understand human glycobiology.

Fucosylated terminal lactosaminyl glycans can be displayed on glycoprotein N-glycans or O-glycans or on glycosphingolipids (GSLs). In prior studies of α(1,3)-FT product specificities, the carrier scaffold "preferences" were commonly not analyzed, though it is well-recognized that the scaffolds play important roles in modulating the function of the glycan moiety. For example, E-selectin ligand motifs (i.e., sLe$^X$, VIM-2, and di-fucosyl sLe$^X$) on O-glycans and N-glycans participate in initiating E-selectin-mediated tethering and rolling of human myeloid leukocytes (61), however, when presented on glycolipids, they also contribute measurably to stabilizing this interaction and critically facilitate the slow rolling of leukocytes on the endothelial cells (62). Using MS, we could comprehensively delineate the glycoconjugate repertoire of fucosylated terminal lactosaminyl glycans, distinguishing whether Le$^X$, sLe$^X$, and di-fucosyl sLe$^X$ were displayed on glycoprotein N-glycans, or O-glycans or GSLs for each α(1,3)-FUT transfectant. Our data indicate that, generally, Le$^X$ production by α(1,3)-FTs showed no significant preference(s) for one scaffold versus another, with the exception of FT5, which does not create Le$^X$ on GSLs (FIG. 8B). However, for sLe$^X$, major variations in scaffold preference were observed: FT6 is the only α(1,3)-FT specialized to construct sLe$^X$ on all three types of glycoconjugate scaffolds, and, contrary to a prior report indicating that human FUT4 transfection in CHO cells robustly creates sLe$^X$ preferentially on glycolipids (50), flow cytometry did not detect any significant level of sLe$^X$ expression on hMSC FUT4 transfectants; MS analysis of FT4 products revealed no sLe$^X$ on glycolipids and only trace sLe$^X$ on O- and N-glycans, whereas FT4 generated Le$^X$ robustly on all types of glycoconjugates. Additionally, in hMSCs, difucosyl sLe$^X$ was detected solely on N-glycans of FUT3, FUT5, FUT6, and FUT7 transfectants, but others have reported that this structure resides abundantly on GSLs (63).

Our study presents the first systematic approach not only to operationally define the human α(1,3)-FTs within the context of a cell, but also to elucidate how these various isoenzymes shape lactosaminyl glycan biosynthesis within a given cell type. Importantly, the pattern of glycans and of their associated glycoconjugates produced by each FT was uniformly consistent among the numerous marrow-derived hMSC cultures for that distinct FUT modRNA transfectant, indicating that modRNA transfection yields reproducibly functional glycosyltransferases that operate with high fidelity and, additionally, that hMSCs possess a characteristic and well-defined lactosaminyl glycan "glycosignature." The in-depth characterization of product specificities of the individual human α(1,3)-FTs provided by our work now offers a useful foundation for designing novel strategies for utilizing these glycosyltransferases, individually or in combination, to custom-engineer fucosylated lactosaminyl glycans for further elucidation of the role(s) of these structures in cell biology and for potential therapeutic purposes. In particular, hMSCs have drawn immense attention for clinical applications, as they natively possess considerable immunomodulatory properties, support tissue regeneration, and can themselves differentiate into various cell types essential for normal physiology (e.g., osteoblasts).

Example 4

Exofucosylation Driven Expression of Cell Surface Glycans

Figure 16:
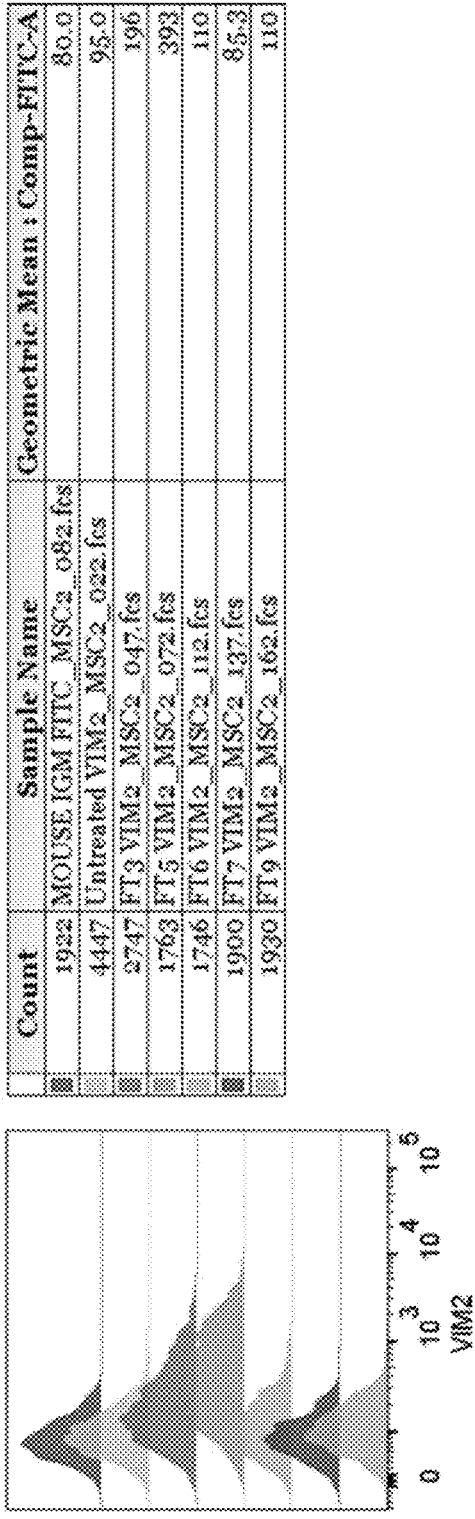
FIG. 16 shows representative flow cytometry histograms of exofucosylated primary hMSCs stained with mAb VIM2 antibody and/or mouse isotype control IgM-FITC. The histograms represent (from top to bottom) mouse IgM-FITC control, untreated cells, FT3 exofucosylated cells, FT5 exofucosylated cells, FT6 exofucosylated cells, FT7 exofucosylated cells, and FT9 exofucosylated cells. Note VIM-2 product in FT3- and FT5-fucosylations.

FIGS. 14 to 16 show examples of flow cytometry data of various cells treated with the indicated fucosyltransferase or untreated controls and stained for the indicated glycan. For exofucosylation, cells were suspended at 1×10$^7$ cells/ml in HBSS, 0.1% human serum albumin (Sigma), 20 mM HEPES (Gibco), 1 mM GDP-fucose (Carbosynth, Compton, UK), and 40 µg/ml purified fucosyltransferase enzyme, and incubated for 1 hour at 37° C. After incubation, cells were washed with PBS and subject to downstream flow cytometry analysis. Cells were stained using mouse or rat IgM FITC secondary antibody alone or incombination with antibodies Le$^x$/CD15-FITC (clone HI98, Biolegend, San Diego, CA), anti sLe$^x$/CD15s-A488 (clone CSLEX1, BD Pharmingen, Billerica, MA), anti CD65s-FITC (clone VIM-2, BioRad) 1 µl mAb FH6 (binding to difucosyl sLe$^x$, Biolegend), and HECA-452 antibody.

As seen in the figures, the exofucosylation of primary blood cell lymphocytes and monocytes, and of MSCs displayed a fucosylated lactosaminyl glycan pattern consistent with the modRNA transferction method. After FT9 exofucosylation of lymphocytes, substantial amounts of Le$^x$ was observed (FIG. 14A), while no significant amounts of sLe$^x$ (FIGS. 14B and C), VIM-2 (FIG. 14. D), and Difucosyl sLe$^x$ (FIG. 14E) was observed. After FT7 exofucosylation of lymphocytes, substantial amounts of sLe$^x$ (FIGS. 14B and C) and Difucosyl sLe$^x$ (FIG. 14E) were observed, while no significant amount of Le$^x$ (FIG. 14A) and VIM-2 (FIG. 14D) was observed. These patterns of fucosylated lactosaminyl glycans via exofucosylation match the patterns observed for MSCs disclosed above.

Similarly, after FT9 exofucosylation of monocytes, substantial amounts of Le$^x$ was observed (FIG. 15A), while no significant amounts of sLe$^x$ (FIGS. 15B and C), VIM-2 (FIG. 15. D), and Difucosyl sLe$^x$ (FIG. 15E) was observed. After FT7 exofucosylation of monocytes, substantial amounts of sLe$^x$ (FIGS. 15B and C) and Difucosyl sLe$^x$ (FIG. 15E) were observed, while no significant amount of Le$^x$ (FIG. 15A) and VIM-2 (FIG. 15D) was observed. These patterns of fucosylated lactosaminyl glycans via exofucosylation also match the patterns observed for MSCs and lymphocytes.

Exofucosylation of MSCs was also performed followed by staining for VIM-2. As shown in FIG. 16, significant amounts of VIM-2 were observed after FT3 and FT5 treatment, while no significant amount of VIM-2 was observed after FT6, FT7, and FT9 treatments. This data confirms that a pattern of VIM-2 may be enforced by exofucosylation consistent with modRNA transfection data disclosed above.

Example 5

Materials and Methods
Isolation and Culture of Human Mesenchymal Stem Cells (hMSCs)

Human cells were obtained and used in accordance with the Declaration of Helsinki and with the procedures approved by Dana Farber/Harvard Cancer Center (DF/HCC) Institutional Review Board (IRB). Bone marrow cells from normal human donors were obtained from discarded bone marrow filter sets by flushing with PBS plus 10 U/ml heparin (Hospira, Lake Forest, IL). The cells were then gradiented using Ficoll-Histopaque 1.077 (Sigma-Aldrich, St. Louis, MO) and the mononuclear fraction was collected. The cells were suspended in MSC media, consisting of DMEM low glucose (1 g/L) supplemented with 10% fetal bovine serum from select lots (Atlanta Biologicals, Atlanta, GA), 100 U/ml penicillin and 100 U/ml streptomycin. Approximately $5 \times 10^8$ cells were seeded into T-175 tissue culture flasks and incubated overnight in a humidified incubator at 37° C., 20% $O_2$, 5% $CO_2$. The next day, all non-adherent cells were removed and the flasks rinsed several times with PBS. The adherent cells were cultured in fresh MSC media, with a full media change twice per week. When the cells approached 80% confluence, cells were harvested with 0.05% trypsin/ 0.5 mM EDTA, washed with PBS for experimental use and/or passaged by diluting 3- to 5-fold in fresh MSC media. Cells were cultured for a maximum of 6 passages before discarding.

Isolation and Culture of Human Peripheral Blood Mononuclear Cells (PBMCs)

A standard protocol was used to obtain PBMCs. Briefly, whole blood diluted in buffer was layered on Ficoll in a conical tube, followed by centrifugation at 400×g for 30-40 minutes at 20 degrees C. The upper plasma layer was aspirated, leaving the PBMC layer undisturbed. The PBMC layer was transferred to a new conical tube, diluted with buffer and centrifuged at 300×g for 10 minutes at 20 degrees C. The supernatant was removed and the pellet resuspended in buffer, followed by centrifugation at 200×g for 10-15 minutes at 20 degrees C. (repeated at least 1×). The supernatant was then removed leaving the PBMC pellet.

Quantitative RT-PCR

Total cellular RNA was purified from bone marrow-derived hMSCs, using RNeasy microkit (QIAGEN, Hilden, Germany) as per the manufacturer's instructions. Total RNA was reverse transcribed to synthesize first strand cDNA using iScript cDNA synthesis kit (Biorad, Hercules, CA) using a heat cycle as follows: 25° C. for 10 min, 42° C. for 60 min and 85° C. for 5 min. For some experiments, SuperScript VILO cDNA conversion kit (Invitrogen, Carlsbad, CA) was used for first strand synthesis using identical thermal cycling conditions. Quantitative real time PCR was performed with specific primers to amplify glycosyltransferase genes (FIG. 13) using SYBR Select master mix (Applied Biosystems, Foster City, CA) and a StepOne Plus PCR detection system (Applied Biosystems). PCR reactions for individual genes were performed in triplicate with each reaction containing 1% (v/v) of the total cDNA obtained. The following cycling condition was employed: Initial activation at 95° C. for 20 sec, followed by 40 cycles of 95° C. for 10 sec and 60° C. for 30 sec. Post amplification, melt curve analysis was performed to ensure primer binding specificity according to the following conditions: 95° C. for 15 sec, 60° C. for 1 min, 3° C. increment every 15 sec to reach 95° C. Gene expression levels were evaluated relative to GAPDH using comparative $C_T$ method. In some cases, agarose gel electrophoresis was performed with the PCR product in order to confirm the size of the amplicon. To this end, PCR products were resolved in a 1.3% agarose gel with 0.2-0.5 µg/ml ethidium bromide. DNA fragments were visualized and imaged using UV illumination (Alphaimager EC imaging system, Alpha-Innotech, San Leandro, CA).

Cloning of FUTs

Full-length human fucosyltransferase cDNAs were purchased from Open Biosystems (GenBank accession numbers for FUTs 3, 4, 5, 6, 7, and 9 cDNAs are BC108675, BC136374, BC140905, BC061700, BC074746, BC036101, respectively) and amplified by PCR using HiFi Hotstart (KAPA Biosystems, Wilmington, MA). PCR products were then subcloned into the pORFIN plasmid (64), which contains the T7 promoter, 5'UTR and 3'UTR required for eventual modified mRNA production, using Quick Ligation Kit (New England Biolabs, Ipswich, MA). The PCR products were first separated using an agarose gel. The products with expected size were gel-purified using QIAquick Gel Extraction Kit (Qiagen) and sequenced to check for mutations before ligation into pORFIN. PCR primer sequences used for cDNA amplification were as follows:

```
FUT3 forward primer:
                                (SEQ ID NO: 1)
AAAAGCGGCCGCCATGGATCCCCTGGGTGCA, reverse primer:
                                (SEQ ID NO: 2)
AAAAAGATCTTCAGGTGAACCAAGCCGCT FUT4 long form forward primer:
                                (SEQ ID NO: 3)
TGAGGCGCTTGTGGGGC, reverse primer:
                                (SEQ ID NO: 4)
AAAAGGATCCTCACCGCTCGAACCAGCTG FUT4 short form forward primer:
                                (SEQ ID NO: 5)
TGGGGGCACCGTGGGGCT, reverse primer:
                                (SEQ ID NO: 6)
AAAAGGATCCTCACCGCTCGAACCAGCTG FUT5 forward primer:
                                (SEQ ID NO: 7)
AAAAGCGGCCGCCATGGATCCCCTGGGCCCA, reverse primer:
                                (SEQ ID NO: 8)
AAAAAGATCTTCAGGTGAACCAAGCCGCTA FUT6 forward primer:
                                (SEQ ID NO: 9)
AAAAGCGGCCGCCATGGATCCCCTGGGCC, reverse primer:
                                (SEQ ID NO: 10)
AAAAAGATCTTCAGGTGAACCAAGCCGCT FUT7 forward primer:
                                (SEQ ID NO: 11)
AAAACGGCCGCATGAATAATGCTGGGCACGGC, reverse primer:
                                (SEQ ID NO: 12)
AAAAGGATCCTCAGGCCTGAAACCAACCCT FUT9 forward primer:
                                (SEQ ID NO: 13)
AAAAGCGGCCGCCATGACATCAACATCCAAAGG, reverse primer:
                                (SEQ ID NO: 14)
AAAAGGATCCTTAATTCCAAAACCATTTCTCTAA
```

Modified mRNA Synthesis

Modified mRNAs (modRNAs) were synthesized as described previously (64). Briefly, human FUT cDNAs cloned in the pORFIN vector were amplified by PCR using HiFi Hotstart (KAPA Biosystems) to generate templates for in vitro transcription. 1.6 µg of the PCR products (including the human FUT open reading frames and 5' and 3' untranslated regions) were then used as templates for modRNA synthesis using the MEGAscript T7 kit (Ambion). 3'-O-Me-m$^7$G(5')ppp(5')G ARCA cap analog (New England Biolabs), adenosine triphosphate, guanosine triphosphate (USB), 5-methylcytidine triphosphate and pseudouridine triphosphate (TriLink Biotechnologies, San Diego, California) were used for in vitro transcription. Synthesized modRNA product was purified using MEGAclear spin columns (Ambion), and aliquots were stored frozen for future use at −80° C.

Modified mRNA Transfection of hMSCs

ModRNAs were transfected into hMSCs using Stemfect (Stemgent, Lexington, MA) as per manufacturer's instructions. Briefly, 1 µg of modRNA and 2 µl of Stemfect reagent were individually diluted into Stemfect buffer, mixed together and incubated for 15 minutes at room temperature. The mixture was then added to $1\times10^6$ recently harvested hMSCs that were suspended in 2 ml of MSC medium, and incubated at 37° C. for 1 hour, inverting the tube at 15-minute intervals. The cells were then diluted in MSC media supplemented with 200 ng/ml of interferon inhibitor (B18R, eBioscience) and cultured in tissue culture flasks for 2 additional days prior to harvest and downstream analysis.

FT Exofucosylation and Surface Sialidase Treatment of hMSCs

Human MSCs were harvested with 0.05% trypsin/0.5 mM EDTA and washed twice with PBS. For sialidase treatment, cells were resuspended at $1\times10^7$ cells/ml in Hank's Balanced Salt Solution (HBSS), 0.1% bovine serum albumin (Sigma) and 0.1 U/ml of either *Arthrobacter ureafaciens* neuraminidase (Sigma), or recombinant *Macrobdella decora* neuraminidase (Calbiochem), and incubated for 45 minutes at 37° C. For exofucosylation, hMSCs were resuspended at $1\times10^7$ cells/ml in HBSS, 0.1% human serum albumin (Sigma), 20 mM HEPES (Gibco), 1 mM GDP-fucose (Carbosynth, Compton, UK), and 60 µg/ml purified FT3, FT5, FT6, FT7, or FT9 enzyme (38), and incubated for 1 hour at 37° C. After incubation, cells were washed with PBS and subject to downstream analysis.

Flow Cytometry

Individual wells of 96-well plates were pre-loaded with 3 µl anti Le$^x$/CD15-FITC (clone HI98, Biolegend, San Diego, CA), 3 µl anti sLe$^x$/CD15s-A488 (clone CSLEX1, BD Pharmingen, Billerica, MA), 20 µl anti CD65s-FITC (clone VIM-2, BioRad) 1 µl mAb FH6 (binding to difucosyl sLe$^x$, Biolegend), 0.1 µl ECA-FITC (*Erythrina Cristagalli* Lectin, binding to unsialylated type 2 lactosamine, Vector Labs, Burlingame, CA), 0.1 µl SNA-FITC (*Sambucus Nigra* lectin, binding to α(2,6)-linked sialic acid, Vector Labs), or 0.1 µl MALII-biotin (*Maackia Amurensis* Lectin II, binding to α(2,3)-linked sialic acid, Vector Labs). hMSCs were harvested, washed, and resuspended in PBS plus 0.1% bovine serum albumin (BSA) at $1\times10^6$ cells/ml. 50 µl of cell suspension was added to each well and incubated at 4° C. for 30 minutes. The plate was washed with 200 µl PBS+BSA per well. Cell pellets were resuspended in PBS+BSA (for directly conjugated antibodies), or secondary antibodies as follows: For FH6, 1 µl FITC conjugated goat anti-mouse Ig (Southern Biotech, Birmingham, AL); for MALII, 1 µl streptavidin-FITC (Biolegend). After incubation for 20 minutes, the plate was washed again with 200 µl/well PBS+BSA and resuspended in 200 µl PBS. Fluorescence intensity was determined using a Cytomics FC 500 MPL flow cytometer (Beckman Coulter, Brea, CA).

Glycan Release and Processing hMSCs were washed with PBS and cell pellets were frozen until use. Cell pellets were thawed, dried and transferred to 13×100 mm glass test tubes. Lipids and glycosphingolipids were extracted with 2:1 HPLC-grade chloroform/methanol. The lipid extracts were dried down and purified and fractionated by silica solid phase extraction (Grace Alltech), as described (65). The dried protein pellet was digested with trypsin and chymotrypsin (Sigma), as described (66). Following heat-inactivation, N-glycans were released with N-glycanase (Prozyme, Hayward, CA) at 37° C. for 48 hours. Released N-glycans were separated from peptides and O-glycopeptides via C18 solid phase extraction (Sep-Pak, Waters, Milford, MA), as described (67). Purified, released N-glycans were reduced via borane-ammonia reduction, as described (68). The reduced N-glycan pool was further purified via graphitized carbon solid phase extraction (Envi-Carb, Supelco, Bellefonte, PA). O-glycans were released from the dried peptide/O-glycopeptide fraction via reductive-elimination, as described (69). Released O-glycans were purified via cation exchange and porous graphitized carbon solid phase extraction. Intact glycosphingolipid fractions, N-glycan fractions, and O-glycans were permethylated via spin column permethylation (Harvard Apparatus, Holliston, MA), as described (70). Permethylated glycans were purified via liquid-liquid extraction with dichloromethane (EMD)/0.5 M aqueous sodium chloride (Fisher). Extracted permethylated glycoprotein glycans were dried and reconstituted in 50:50 HPLC-grade methanol/water for mass spectrometry analysis. Intact permethylated glycosphingolipids were dried and reconstituted with 2:1 HPLC-grade methanol/water for mass spectrometry analysis.

Mass Spectrometry

Direct infusion mass spectrometry experiments were performed using an LTQ (Thermo; ion-trap instrument) equipped with a Nanomate (Advion, Ithaca, NY). Each derived fraction (GSL, O-glycan, and N-glycan) was infused separately and analyzed independently. Normalized collision energy was set to 35% for the LTQ, with activation q set to 0.250 and activation time set to 30 ms. Peak selection for sequential disassembly was made manually; isolation widths were generally set to 2.0 m/z, and isolation was centered at m/z values approximately 0.5-1.0 units higher than the monoisotopic peak in order to capture the entire isotopic envelope. All ions are sodium adducts, unless otherwise noted. Interpretation of mass spectral data sets was made manually. Where relevant and possible, and when standard materials and mass spectra were available, unknown substructure spectra were compared to standard spectra, as described (71,72). For each spectrum, normalization level (NL) and signal average time are indicated. Liquid chromatography-mass spectrometry analysis of O-glycans was performed using a reversed-phase (C18) column (Thermo BDS Hypersil, 1×150 mm) with a 0.1% formic acid/acetonitrile gradient to elute the reduced and permethylated O-glycans. A Surveyor MS pump and Surveyor autosampler were employed in conjunction with a VelosPro mass spectrometer (all from Thermo). Peak areas of molecular ions were used for relative quantitation. Detailed structure analysis and confirmation were made by direct infusion $MS^n$.

Although illustrative embodiments of the present invention have been described herein, it should be understood that the invention is not limited to those described, and that various other changes or modifications may be made by one skilled in the art without departing from the scope or spirit of the invention. The disclosures of all patent and scientific literature cited herein are expressly incorporated in their entirety by reference.

REFERENCES

1. Sackstein, R. (2009) Glycosyltransferase-programmed stereosubstitution (GPS) to create HCELL: engineering a roadmap for cell migration. *Immunol Rev* 230, 51-74
2. Gooi, H. C., Feizi, T., Kapadia, A., Knowles, B. B., Solter, D., and Evans, M. J. (1981) Stage-specific embryonic antigen involves alpha 1 goes to 3 fucosylated type 2 blood group chains. *Nature* 292, 156-158
3. Solter, D., and Knowles, B. B. (1978) Monoclonal antibody defining a stage-specific mouse embryonic antigen (SSEA-1). *Proc Natl Acad Sci USA* 75, 5565-5569
4. Fenderson, B. A., Zehavi, U., and Hakomori, S. (1984) A multivalent lacto-N-fucopentaose III-lysyllysine conjugate decompacts preimplantation mouse embryos, while the free oligosaccharide is ineffective. *J Exp Med* 160, 1591-1596
5. Capela, A., and Temple, S. (2002) LeX/ssea-1 is expressed by adult mouse CNS stem cells, identifying them as nonependymal. *Neuron* 35, 865-875
6. Klassen, H., Schwartz, M. R., Bailey, A. H., and Young, M. J. (2001) Surface markers expressed by multipotent human and mouse neural progenitor cells include tetraspanins and non-protein epitopes. *Neurosci Lett* 312, 180-182
7. Yanagisawa, M., Taga, T., Nakamura, K., Ariga, T., and Yu, R. K. (2005) Characterization of glycoconjugate antigens in mouse embryonic neural precursor cells. *J Neurochem* 95, 1311-1320
8. Pruszak, J., Ludwig, W., Blak, A., Alavian, K., and Isacson, O. (2009) CD15, CD24, and CD29 Define a Surface Biomarker Code for Neural Lineage Differentiation of Stem Cells. *STEM CELLS* 27, 2928-2940
9. Yagi, H., Saito, T., Yanagisawa, M., Yu, R. K., and Kato, K. (2012) Lewis X-carrying N-glycans regulate the proliferation of mouse embryonic neural stem cells via the Notch signaling pathway. *J Biol Chem* 287, 24356-24364
10. van Gisbergen, K. P., Sanchez-Hernandez, M., Geijtenbeek, T. B., and van Kooyk, Y. (2005) Neutrophils mediate immune modulation of dendritic cells through glycosylation-dependent interactions between Mac-1 and DC-SIGN. *J Exp Med* 201, 1281-1292
11. Gruss, H. J., and Kadin, M. E. (1996) Pathophysiology of Hodgkin's disease: functional and molecular aspects. *Baillieres Clin Haematol* 9, 417-446
12. Read, T. A., Fogarty, M. P., Markant, S. L., McLendon, R. E., Wei, Z., Ellison, D. W., Febbo, P. G., and Wechsler-Reya, R. J. (2009) Identification of CD15 as a marker for tumor-propagating cells in a mouse model of medulloblastoma. *Cancer cell* 15, 135-147
13. Seidmann, L., Anspach, L., and Roth, W. (2016) The embryo-placental CD15-positive "vasculogenic zones" as a source of propranolol-sensitive pediatric vascular tumors. *Placenta* 38, 93-99
14. Foxall, C., Watson, S. R., Dowbenko, D., Fennie, C., Lasky, L. A., Kiso, M., Hasegawa, A., Asa, D., and Brandley, B. K. (1992) The three members of the selectin receptor family recognize a common carbohydrate epitope, the sialyl Lewis(x) oligosaccharide. *J Cell Biol* 117, 895-902
15. Sackstein, R. (2004) The bone marrow is akin to skin: HCELL and the biology of hematopoietic stem cell homing. *The Journal of investigative dermatology* 122, 1061-1069
16. Merzaban, J. S., Burdick, M. M., Gadhoum, S. Z., Dagia, N. M., Chu, J. T., Fuhlbrigge, R. C., and Sackstein, R. (2011) Analysis of glycoprotein E-selectin ligands on human and mouse marrow cells enriched for hematopoietic stem/progenitor cells. *Blood* 118, 1774-1783
17. Silva, M., Fung, R. K., Donnelly, C. B., Videira, P. A., and Sackstein, R. (2017) Cell-Specific Variation in E-Selectin Ligand Expression among Human Peripheral Blood Mononuclear Cells: Implications for Immunosurveillance and Pathobiology. *J Immunol*
18. Julien, S., Ivetic, A., Grigoriadis, A., QiZe, D., Burford, B., Sproviero, D., Picco, G., Gillett, C., Papp, S. L., Schaffer, L., Tutt, A., Taylor-Papadimitriou, J., Pinder, S. E., and Burchell, J. M. (2011) Selectin ligand sialyl-Lewis x antigen drives metastasis of hormone-dependent breast cancers. *Cancer Res* 71, 7683-7693
19. Liang, J. X., Liang, Y., and Gao, W. (2016) Clinicopathological and prognostic significance of sialyl Lewis X overexpression in patients with cancer: a meta-analysis. *OncoTargets and therapy* 9, 3113-3125
20. St Hill, C. A. (2011) Interactions between endothelial selectins and cancer cells regulate metastasis. *Front Biosci (Landmark Ed)* 16, 3233-3251
21. Handa, K., Stroud, M. R., and Hakomori, S. (1997) Sialosyl-fucosyl Poly-LacNAc without the sialosyl-Le$^x$ epitope as the physiological myeloid cell ligand in E-selectin-dependent adhesion: studies under static and dynamic flow conditions. *Biochemistry* 36, 12412-12420
22. Tiemeyer, M., Swiedler, S. J., Ishihara, M., Moreland, M., Schweingruber, H., Hirtzer, P., and Brandley, B. K. (1991) Carbohydrate ligands for endothelial-leukocyte adhesion molecule 1. *Proc Natl Acad Sci USA* 88, 1138-1142
23. Kukowska-Latallo, J. F., Larsen, R. D., Nair, R. P., and Lowe, J. B. (1990) A cloned human cDNA determines expression of a mouse stage-specific embryonic antigen and the Lewis blood group alpha(1,3/1,4)fucosyltransferase. *Genes & Development* 4, 1288-1303
24. Lowe, J. B., Kukowska-Latallo, J. F., Nair, R. P., Larsen, R. D., Marks, R. M., Macher, B. A., Kelly, R. J., and Ernst, L. K. (1991) Molecular cloning of a human fucosyltransferase gene that determines expression of the Lewis x and VIM-2 epitopes but not ELAM-1-dependent cell adhesion. *Journal of Biological Chemistry* 266, 17467-17477
25. Goelz, S. E., Hession, C., Goff, D., Griffiths, B., Tizard, R., Newman, B., Chi-Rosso, G., and Lobb, R. (1990) ELFT: A gene that directs the expression of an ELAM-1 ligand. *Cell* 63, 1349-1356
26. Weston, B. W., Nair, R. P., Larsen, R. D., and Lowe, J. B. (1992) Isolation of a novel human alpha (1,3) fucosyltransferase gene and molecular comparison to the human Lewis blood group alpha (1,3/1,4)fucosyltransferase gene. Syntenic, homologous, nonallelic genes encoding enzymes with distinct acceptor substrate specificities. *J Biol Chem* 267, 4152-4160
27. Weston, B. W., Smith, P. L., Kelly, R. J., and Lowe, J. B. (1992) Molecular cloning of a fourth member of a human alpha (1,3)fucosyltransferase gene family. Multiple homologous sequences that determine expression of the Lewis x, sialyl Lewis x, and difucosyl sialyl Lewis x epitopes. *J Biol Chem* 267, 24575-24584
28. Natsuka, S., Gersten, K. M., Zenita, K., Kannagi, R., and Lowe, J. B. (1994) Molecular cloning of a cDNA encoding a novel human leukocyte alpha-1,3-fucosyltransferase capable of synthesizing the sialyl Lewis x determinant. *J Biol Chem* 269, 16789-16794
29. Kaneko, M., Kudo, T., Iwasaki, H., Ikehara, Y., Nishihara, S., Nakagawa, S., Sasaki, K., Shiina, T., Inoko, H., and Saitou, N. (1999) Alpha1,3-fucosyltransferase IX (Fuc-TIX) is very highly conserved between human and mouse; molecular cloning, characterization and tissue distribution of human Fuc-TIX. *FEBS Lett* 452
30. Sasaki, K., Kurata, K., Funayama, K., Nagata, M., Watanabe, E., Ohta, S., Hanai, N., and Nishi, T. (1994) Expression cloning of a novel alpha 1,3-fucosyltransferase that is involved in biosynthesis of the sialyl Lewis x carbohydrate determinants in leukocytes. *J Biol Chem* 269, 14730-14737
31. Kimura, H., Shinya, N., Nishihara, S., Kaneko, M., Irimura, T., and Narimatsu, H. (1997) Distinct substrate specificities of five human alpha-1,3-fucosyltransferases for in vivo synthesis of the sialyl Lewis x and Lewis x epitopes. *Biochem Biophys Res Commun* 237, 131-137
32. Cailleau-Thomas, A., Coullin, P., Candelier, J. J., Balanzino, L., Mennesson, B., Oriol, R., and Mollicone, R. (2000) FUT4 and FUT9 genes are expressed early in human embryogenesis. *Glycobiology* 10, 789-802
33. Niemelä, R., Natunen, J., Majuri, M.-L., Maaheimo, H., Helin, J., Lowe, J. B., Renkonen, O., and Renkonen, R. (1998) Complementary Acceptor and Site Specificities of Fuc-TIV and Fuc-TVII Allow Effective Biosynthesis of Sialyl-TriLex and Related Polylactosamines Present on Glycoprotein Counterreceptors of Selectins. *Journal of Biological Chemistry* 273, 4021-4026
34. Nishihara, S., Iwasaki, H., Kaneko, M., Tawada, A., Ito, M., and Narimatsu, H. (1999) α1,3-Fucosyltransferase 9 (FUT9; Fuc-TIX) preferentially fucosylates the distal GlcNAc residue of polylactosamine chain while the other four α1,3FUT members preferentially fucosylate the inner GlcNAc residue. *FEBS Letters* 462, 289-294
35. Shetterly, S., Jost, F., Watson, S. R., Knegtel, R., Macher, B. A., and Holmes, E. H. (2007) Site-specific fucosylation of sialylated polylactosamines by alpha1,3/4-fucosyltransferases-V and -VI Is defined by amino acids near the N terminus of the catalytic domain. *J Biol Chem* 282, 24882-24892
36. Basu, M., Hawes, J. W., Li, Z., Ghosh, S., Khan, F. A., Zhang, B. J., and Basu, S. (1991) Biosynthesis in vitro of SA-Lex and SA-diLex by alpha 1-3 fucosyltransferases from colon carcinoma cells and embryonic brain tissues. *Glycobiology* 1, 527-535
37. Becker, D. J., and Lowe, J. B. (2003) Fucose: biosynthesis and biological function in mammals. *Glycobiology* 13, 41R-53R
38. Dykstra, B., Lee, J., Mortensen, L. J., Yu, H., Wu, Z. L., Lin, C. P., Rossi, D. J., and Sackstein, R. (2016) Glycoengineering of E-Selectin Ligands by Intracellular versus Extracellular Fucosylation Differentially Affects Osteotropism of Human Mesenchymal Stem Cells. *Stem Cells* 34, 2501-2511
39. Madeira, C., Mendes, R. D., Ribeiro, S. C., Boura, J. S., Aires-Barros, M. R., da Silva, C. L., and Cabral, J. M. (2010) Nonviral gene delivery to mesenchymal stem cells using cationic liposomes for gene and cell therapy. *J Biomed Biotechnol* 2010, 735349
40. Sackstein, R., Merzaban, J. S., Cain, D. W., Dagia, N. M., Spencer, J. A., Lin, C. P., and Wohlgemuth, R. (2008) Ex vivo glycan engineering of CD44 programs human multipotent mesenchymal stromal cell trafficking to bone. *Nat Med* 14, 181-187
41. Geisler, C., and Jarvis, D. L. (2011) Letter to the Glyco-Forum: Effective glycoanalysis with *Maackia amurensis* lectins requires a clear understanding of their binding specificities. *Glycobiology* 21, 988-993
42. Bai, X., Brown, J. R., Varki, A., and Esko, J. D. (2001) Enhanced 3-O-sulfation of galactose in Asn-linked glycans and *Maackia* amurenesis lectin binding in a new Chinese hamster ovary cell line. *Glycobiology* 11, 621-632

43. Chou, M.-Y., Li, S.-C., and Li, Y.-T. (1996) Cloning and Expression of Sialidase L, a NeuAcα2→3Gal-specific Sialidase from the Leech, *Macrobdella decora*. *Journal of Biological Chemistry* 271, 19219-19224
44. Kumar, R., Potvin, B., Muller, W. A., and Stanley, P. (1991) Cloning of a human alpha(1,3)-fucosyltransferase gene that encodes ELFT but does not confer ELAM-1 recognition on Chinese hamster ovary cell transfectants. *J Biol Chem* 266, 21777-21783
45. Sackstein, R. (2012) Re: Ex vivo fucosylation improves human cord blood engraftment in NOD-SCID IL-2R null mice. *Experimental Hematology* 40, 518-519
46. Mollicone, R., Moore, S. E. H., Bovin, N., Garcia-Rosasco, M., Candelier, J.-J., Martinez-Duncker, I., and Oriol, R. (2009) Activity, Splice Variants, Conserved Peptide Motifs, and Phylogeny of Two New α1,3-Fucosyltransferase Families (FUT10 and FUT11). *Journal of Biological Chemistry* 284, 4723-4738
47. Kumar, A., Torii, T., Ishino, Y., Muraoka, D., Yoshimura, T., Togayachi, A., Narimatsu, H., Ikenaka, K., and Hitoshi, S. (2013) The Lewis X-related α1,3-Fucosyltransferase, Fut10, Is Required for the Maintenance of Stem Cell Populations. *Journal of Biological Chemistry* 288, 28859-28868
48. Barthel, S. R., Wiese, G. K., Cho, J., Opperman, M. J., Hays, D. L., Siddiqui, J., Pienta, K. J., Furie, B., and Dimitroff, C. J. (2009) Alpha 1,3 fucosyltransferases are master regulators of prostate cancer cell trafficking. *Proceedings of the National Academy of Sciences* 106, 19491-19496
49. Zollner, O., and Vestweber, D. (1996) The E-selectin ligand-1 is selectively activated in Chinese hamster ovary cells by the alpha(1,3)-fucosyltransferases IV and VII. *J Biol Chem* 271, 33002-33008
50. Huang, M. C., Laskowska, A., Vestweber, D., and Wild, M. K. (2002) The alpha (1,3)-fucosyltransferase Fuc-TIV, but not Fuc-TVII, generates sialyl Lewis X-like epitopes preferentially on glycolipids. *J Biol Chem* 277, 47786-47795
51. Knibbs, R. N., Craig, R. A., Natsuka, S., Chang, A., Cameron, M., Lowe, J. B., and Stoolman, L. M. (1996) The fucosyltransferase FucT-VII regulates E-selectin ligand synthesis in human T cells. *J Cell Biol* 133, 911-920
52. Nakayama, F., Nishihara, S., Iwasaki, H., Kudo, T., Okubo, R., Kaneko, M., Nakamura, M., Karube, M., Sasaki, K., and Narimatsu, H. (2001) CD15 Expression in Mature Granulocytes Is Determined by α1,3-Fucosyltransferase IX, but in Promyelocytes and Monocytes by α1,3-Fucosyltransferase IV. *Journal of Biological Chemistry* 276, 16100-16106
53. Patnaik, S. K., Potvin, B., and Stanley, P. (2004) LEC12 and LEC29 Gain-of-Function Chinese Hamster Ovary Mutants Reveal Mechanisms for Regulating VIM-2 Antigen Synthesis and E-selectin Binding. *Journal of Biological Chemistry* 279, 49716-49726
54. Buffone, A., Mondal, N., Gupta, R., McHugh, K. P., Lau, J. T. Y., and Neelamegham, S. (2013) Silencing α1,3-Fucosyltransferases in Human Leukocytes Reveals a Role for FUT9 Enzyme during E-selectin-mediated Cell Adhesion. *Journal of Biological Chemistry* 288, 1620-1633
55. Tu, L., and Banfield, D. K. (2010) Localization of Golgi-resident glycosyltransferases. *Cellular and Molecular Life Sciences* 67, 29-41
56. Maly, P., Thall, A., Petryniak, B., Rogers, C. E., Smith, P. L., Marks, R. M., Kelly, R. J., Gersten, K. M., Cheng, G., Saunders, T. L., Camper, S. A., Camphausen, R. T., Sullivan, F. X., Isogai, Y., Hindsgaul, O., von Andrian, U. H., and Lowe, J. B. (1996) The alpha(1,3)fucosyltransferase Fuc-TVII controls leukocyte trafficking through an essential role in L-, E-, and P-selectin ligand biosynthesis. *Cell* 86, 643-653
57. Homeister, J. W., Daugherty, A., and Lowe, J. B. (2004) Alpha(1,3)fucosyltransferases FucT-IV and FucT-VII control susceptibility to atherosclerosis in apolipoprotein E−/− mice. *Arterioscler Thromb Vasc Biol* 24, 1897-1903
58. Smithson, G., Rogers, C. E., Smith, P. L., Scheidegger, E. P., Petryniak, B., Myers, J. T., Kim, D. S., Homeister, J. W., and Lowe, J. B. (2001) Fuc-TVII is required for T helper 1 and T cytotoxic 1 lymphocyte selectin ligand expression and recruitment in inflammation, and together with Fuc-TIV regulates naive T cell trafficking to lymph nodes. *J Exp Med* 194, 601-614
59. Homeister, J. W., Thall, A. D., Petryniak, B., Maly, P., Rogers, C. E., Smith, P. L., Kelly, R. J., Gersten, K. M., Askari, S. W., and Cheng, G. (2001) The alpha(1,3) fucosyltransferases FucT-IV and FucT-VII exert collaborative control over selectin-dependent leukocyte recruitment and lymphocyte homing. *Immunity* 15
60. Gersten, K. M., Natsuka, S., Trinchera, M., Petryniak, B., Kelly, R. J., Hiraiwa, N., Jenkins, N. A., Gilbert, D. J., Copeland, N. G., and Lowe, J. B. (1995) Molecular Cloning, Expression, Chromosomal Assignment, and Tissue-specific Expression of a Murine α-(1,3)-Fucosyltransferase Locus Corresponding to the Human ELAM-1 Ligand Fucosyl Transferase. *Journal of Biological Chemistry* 270, 25047-25056
61. Stolfa, G., Mondal, N., Zhu, Y., Yu, X., Buffone, A., Jr., and Neelamegham, S. (2016) Using CRISPR-Cas9 to quantify the contributions of O-glycans, N-glycans and Glycosphingolipids to human leukocyte-endothelium adhesion. *Scientific reports* 6, 30392
62. Mondal, N., Stolfa, G., Antonopoulos, A., Zhu, Y., Wang, S. S., Buffone, A., Jr., Atilla-Gokcumen, G. E., Haslam, S. M., Dell, A., and Neelamegham, S. (2016) Glycosphingolipids on Human Myeloid Cells Stabilize E-Selectin-Dependent Rolling in the Multistep Leukocyte Adhesion Cascade. *Arterioscler Thromb Vasc Biol* 36, 718-727
63. Fukushi, Y., Nudelman, E., Levery, S. B., Hakomori, S., and Rauvala, H. (1984) Novel fucolipids accumulating in human adenocarcinoma. III. A hybridoma antibody (FH6) defining a human cancer-associated difucoganglioside (VI3NeuAcV3III3Fuc2nLc6). *J Biol Chem* 259, 10511-10517
64. Mandal, P. K., and Rossi, D. J. (2013) Reprogramming human fibroblasts to pluripotency using modified mRNA. *Nat Protoc* 8, 568-582
65. Garner, B., Priestman, D. A., Stocker, R., Harvey, D. J., Butters, T. D., and Platt, F. M. (2002) Increased glycosphingolipid levels in serum and aortae of apolipoprotein E gene knockout mice. *J Lipid Res* 43, 205-214
66. Aoki, K., Perlman, M., Lim, J. M., Cantu, R., Wells, L., and Tiemeyer, M. (2007) Dynamic developmental elaboration of N-linked glycan complexity in the *Drosophila melanogaster* embryo. *J Biol Chem* 282, 9127-9142

67. Canis, K., McKinnon, T. A., Nowak, A., Panico, M., Morris, H. R., Laffan, M., and Dell, A. (2010) The plasma von Willebrand factor O-glycome comprises a surprising variety of structures including ABH antigens and disialosyl motifs. *J Thromb Haemost* 8, 137-145
68. Alley, W. R., Jr., Madera, M., Mechref, Y., and Novotny, M. V. (2010) Chip-based reversed-phase liquid chromatography-mass spectrometry of permethylated N-linked glycans: a potential methodology for cancer-biomarker discovery. *Anal Chem* 82, 5095-5106
69. Carlson, D. M. (1966) Oligosaccharides isolated from pig submaxillary mucin. *J Biol Chem* 241, 2984-2986
70. Kang, P., Mechref, Y., Klouckova, I., and Novotny, M. V. (2005) Solid-phase permethylation of glycans for mass spectrometric analysis. *Rapid Commun Mass Spectrom* 19, 3421-3428
71. Ashline, D. J., Hanneman, A. J., Zhang, H., and Reinhold, V. N. (2014) Structural documentation of glycan epitopes: sequential mass spectrometry and spectral matching. *J Am Soc Mass Spectrom* 25, 444-453
72. Ashline, D. J., Zhang, H., and Reinhold, V. N. (2017) Isomeric complexity of glycosylation documented by MSn. *Anal Bioanal Chem* 409, 439-451
73. Mollicone, R., et al., Molecular basis for Lewis alpha(1,3/1,4)-fucosyltransferase gene deficiency (FUT3) found in Lewis-negative Indonesian pedigrees. *Journal of Biological Chemistry*, 1994. 269(33): p. 20987-20994.
74. Nishihara, S., et al., *Human α-1,3 Fucosyltransferase (FucT-VI) Gene Is Located at Only 13 kb 3' to the Lewis Type Fucosyltransferase (FucT-III) Gene on Chromosome 19*. Biochemical and Biophysical Research Communications, 1993. 190(1): p. 42-46.
75. Cameron, H. S., D. Szczepaniak, and B. W. Weston, Expression of Human Chromosome 19p α(1, 3)-Fucosyltransferase Genes in Normal Tissues: ALTERNATIVE SPLICING, POLYADENYLATION, AND ISOFORMS. *Journal of Biological Chemistry*, 1995. 270(34): p. 20112-20122.
76. de Vries, T., et al., *Acceptor Specificity of Different Length Constructs of Human Recombinant α1,3/4-Fucosyltransferases: REPLACEMENT OF THE STEM REGION AND THE TRANSMEMBRANE DOMAIN OF FUCOSYLTRANSFERASE V BY PROTEIN A RESULTS IN AN ENZYME WITH GDP-FUCOSE HYDROLYZING ACTIVITY*. Journal of Biological Chemistry, 1995. 270(15): p. 8712-8722.
77. De Vries, T., et al., *Acceptor specificity of GDP-Fuc: Galβ1→4GlcNAc-R á3-fucosyltransferase VI (FucT VI) expressed in insect cells as soluble, secreted enzyme*. Glycobiology, 1997. 7(7): p. 921-927.
78. Lowe, J. B., et al., *Molecular cloning of a human fucosyltransferase gene that determines expression of the Lewis x and VIM-2 epitopes but not ELAM-1-dependent cell adhesion*. Journal of Biological Chemistry, 1991. 266(26): p. 17467-17477.
79. Clarke, J. L. and W. M. Watkins, 1,3-L-Fucosyltransferase Expression in Developing Human Myeloid Cells: ANTIGENIC, ENZYMATIC, AND mRNA ANALYSES. *Journal of Biological Chemistry*, 1996. 271(17): p. 10317-10328.
80. Chandrasekaran, E. V., et al., Specificity Analysis of Three Clonal and Five Non-Clonal á1,3-1-Fucosyltransferases with Sulfated, Sialylated, or Fucosylated Synthetic Carbohydrates as Acceptors in Relation to the Assembly of 3'-Sialyl-6'-sulfo Lewis x (the L-Selectin Ligand) and Related Complex Structures. Biochemistry, 1996. 35(27): p. 8925-8933.
81. Nyström, K., et al., Virus-induced transcriptional activation of host FUT genes associated with neo-expression of Ley in cytomegalovirus-infected and sialyl-Lex in varicella-zoster virus-infected diploid human cells. Glycobiology, 2007. 17(4): p. 355-366.
82. Nyström, K., et al., *Induction of sialyl-Lex expression by herpes simplex virus type 1 is dependent on viral immediate early RNA-activated transcription of host fucosyltransferase genes*. Glycobiology, 2009. 19(8): p. 847-859.
83. Koszdin, K. L. and B. R. Bowen, *The cloning and expression of a human α-1,3 fucosyltransferase capable of forming the E-selectin ligand*. Biochemical and Biophysical Research Communications, 1992. 187 (1): p. 152-157.
84. Costache, M., et al., *Evolution of Fucosyltransferase Genes in Vertebrates*. Journal of Biological Chemistry, 1997. 272(47): p. 29721-29728.
85. Borsig, L., et al., *Trafficking and localization studies of recombinant α1,3-fucosyltransferase VI stably expressed in CHO cells*. Glycobiology, 1998. 8(3): p. 259-268.
86. Izawa, M., et al., *Expression of Sialyl 6-Sulfo Lewis X Is Inversely Correlated with Conventional Sialyl Lewis X Expression in Human Colorectal Cancer*. Cancer Research, 2000. 60(5): p. 1410-1416.
87. Wagers, A. J., J. B. Lowe, and G. S. Kansas, *An important role for the alpha 1,3 fucosyltransferase, FucT-VII, in leukocyte adhesion to E-selectin*. Blood, 1996. 88(6): p. 2125-32.
88. Kudo, T., et al., *Expression cloning and characterization of a novel murine alpha1,3-fucosyltransferase, mFuc-TIX, that synthesizes the Lewis x (CD15) epitope in brain and kidney*. J Biol Chem, 1998. 273(41): p. 26729-38.
89. Huang, M.-C., et al., *P-selectin Glycoprotein Ligand-1 and E-selectin Ligand-1 Are Differentially Modified by Fucosyltransferases Fuc-TIV and Fuc-TVII in Mouse Neutrophils*. Journal of Biological Chemistry, 2000. 275(40): p. 31353-31360.
90. R. Sackstein, Curr Opin Hematol 12, 444 (2005)
91. T. Lapidot, A. Dar, O. Kollet, Blood 106, 1901 (2005)
92. T. A. Springer, Cell 76, 301 (1994)
93. A. Peled et al., Science 283, 845 (1999)
94. D. A. Sipkins et al., Nature 435, 969 (2005)
95. R. Sackstein, Immunol. Rev. 230: 140-163 (2009)
96. M. J. Polley et al., Proc Natl Acad Sci USA 88, 6224 (1991)
97. Z. Laszik et al., Blood 88, 3010 (1996)
98. C. J. Dimitroff, J. Y. Lee, S. Rafii, R. C. Fuhlbrigge, R. Sackstein, J Cell Biol 153, 1277 (2001)
99. C. J. Dimitroff, J. Y. Lee, R. C. Fuhlbrigge, R. Sackstein, Proc Natl Acad Sci US A 97, 13841 (2000)
100. Fuhlbrigge et al Blood 107:1421-1426 (2006)
101. R. Sackstein, C. J. Dimitroff, Blood 96, 2765 (2000)
102. C. J. Dimitroff, J. Y. Lee, K. S. Schor, B. M. Sandmaier, R. Sackstein, J Biol Chem 276, 47623 (2001)
103. C. J. Dimitroff, J. Y. Lee, S. Rafii, R. C. Fuhlbrigge, R. Sackstein, J Cell Biol 153, 1277 (2001)
104. N. E. Good, G. D. Winget, W. Winter, T N. Conolly, S. Izawa and R. M. M. Singh, Biochemistry 5, 467 (1966)
105. N. E. Good, S. Izawa, Methods Enzymol. 24, 62 (1972)

106. Bertozzi et al., Annu. Rev. Cell Dev. Biol. 2001, 17:1-23
107. Wu et al., Glycobiology, Vol. 28, Issue 2, 69-79
108. Donnelly C, Dykstra B, Mondal N, Huang J, Kaskow B J, Griffin R, Sackstein R, Baecher-Allan C., *Optimizing human Treg immunotherapy by Treg subset selection and E-selectin ligand expression.*, Sci Rep. 2018 Jan. 11; 8(1):420
109. Lee J, Dykstra B, Spencer J A, Kenney L L, Greiner D L, Shultz L D, Brehm M A, Lin C P, Sackstein R, Rossi D J, *mRNA-mediated glycoengineering ameliorates deficient homing of human stem cell-derived hematopoietic progenitors*, J Clin Invest. 2017 Jun. 1; 127(6):2433-2437
110. Silva M, Fung R K F, Donnelly C B, Videira P A, Sackstein R., *Cell-Specific Variation in E-Selectin Ligand Expression among Human Peripheral Blood Mononuclear Cells: Implications for Immunosurveillance and Pathobiology*, J Immunol. 2017 May 1; 198(9):3576-3587
111. Pachón-Peña G, Donnelly C, Ruiz-Cañada C, Katz A, Fernández-Veledo S, Vendrell J, Sackstein R., *A Glycovariant of Human CD44 is Characteristically Expressed on Human Mesenchymal Stem Cells*, Stem Cells. 2017 April; 35(4):1080-1092
112. Dykstra B, Lee J, Mortensen L J, Yu H, Wu Z L, Lin C P, Rossi D J, Sackstein R., *Glycoengineering of E-Selectin Ligands by Intracellular versus Extracellular Fucosylation Differentially Affects Osteotropism of Human Mesenchymal Stem Cells*, Stem Cells. 2016 October; 34(10):2501-2511

---

What is claimed is:

1. A process for custom engineering a fucosylated lactosaminyl glycan comprising:
    (a) determining a desired enforced glycosylation pattern for a target human cell, wherein the enforced glycosylation pattern is selected from the group consisting of:
        (i) sLe$^x$ (+)>>Le$^x$(+), with Di-Fuc-sLe$^x$ (+), and VIM-2 (−); and
        (ii) Le$^x$(+), sLe$^x$ (−), VIM-2 (−), and Di-Fuc-sLe$^x$ (−);
    (b) selecting an α(1,3)-fucosyltransferase VI capable of producing the desired glycosylation pattern; and
    (c) contacting the target human cell with the selected α(1,3)-fucosyltransferase VI.

2. The process according to claim 1, wherein contacting the human cell with Fucosyltransferase IV results in the enforced glycosylation pattern of (i).

3. A method for identifying a human cell via its glycosignature comprising the steps of:
    (a) providing a population of human cells;
    (b) contacting the population of human cells with an α(1,3)-fucosyltransferase VI;
    (c) detecting fucosylated lactosaminyl glycans Le$^x$, sLe$^x$, VIM-2, and Di-Fuc-sLe$^x$ on the population of human cells of step (b); and
    (d) identifying the population of human cells detected in step (c) having an enforced fucosylated lactosaminyl glycan pattern selected from the group consisting of:
        (i) sLe$^x$ (+)>>Le$^x$(+), with Di-Fuc-sLe$^x$ (+), and VIM-2 (−); and
        (ii) Le$^x$(+), sLe$^x$ (−), VIM-2 (−), and Di-Fuc-sLe$^x$ (−).

4. The method according to claim 3, wherein contacting the cell with Fucosyltransferase VI results in the enforced glycosylation pattern of (i).

\* \* \* \* \*

UNITED STATES PATENT AND TRADEMARK OFFICE
CERTIFICATE OF CORRECTION

PATENT NO. : 11,939,616 B2
APPLICATION NO. : 17/027794
DATED : March 26, 2024
INVENTOR(S) : Robert Sackstein It is certified that error appears in the above-identified patent and that said Letters Patent is hereby corrected as shown below:

In the Claims

In Claim 2, Column 83, Line 25, "Fucosyltransferase IV" should read --Fucosyltransferase VI--.

Signed and Sealed this
Thirteenth Day of August, 2024

Katherine Kelly Vidal
*Director of the United States Patent and Trademark Office*